United States Patent
Lavi et al.

(10) Patent No.: US 7,717,877 B2
(45) Date of Patent: *May 18, 2010

(54) INJECTING APPARATUS

(75) Inventors: Gilad Lavi, Rishon Letzion (IL); Izrail Tsals, Newtown, PA (US)

(73) Assignee: SID Technologies, LLC, Newtown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/566,333

(22) PCT Filed: Jul. 28, 2004

(86) PCT No.: PCT/IB2004/051318

§ 371 (c)(1),
(2), (4) Date: Jan. 27, 2006

(87) PCT Pub. No.: WO2005/009515

PCT Pub. Date: Feb. 3, 2005

(65) Prior Publication Data

US 2007/0112310 A1    May 17, 2007

Related U.S. Application Data

(60) Provisional application No. 60/518,936, filed on Nov. 12, 2003, provisional application No. 60/491,196, filed on Jul. 31, 2003.

(51) Int. Cl.
*A61M 5/20* (2006.01)
*A61M 5/32* (2006.01)

(52) U.S. Cl. .................. 604/137; 604/135; 604/198

(58) Field of Classification Search ................ 604/131, 604/192–197, 110, 198, 245, 134–137, 167
See application file for complete search history.

(56) References Cited

U.S. PATENT DOCUMENTS

| 2,398,544 A | | 4/1946 | Lockhart |
| 2,701,566 A | * | 2/1955 | Krug .......................... 604/154 |
| 2,752,918 A | | 7/1956 | Uytenbogaart |
| 2,876,770 A | * | 3/1959 | White ........................ 604/198 |

(Continued)

FOREIGN PATENT DOCUMENTS

DE        3715337 A1    11/1988

(Continued)

*Primary Examiner*—Kevin C Sirmons
*Assistant Examiner*—Michael J Anderson
(74) *Attorney, Agent, or Firm*—Caesar, Rivise, Bernstein, Cohen & Pokotilow, Ltd.

(57) ABSTRACT

An injector is automatic in that the needle is inserted into the injection site (e.g., a patient's skin) with user or caregiver assistance, the delivery is automatically initiated upon needle insertion, and the needle is retracted automatically after the end of delivery. Preferably the needle is not seen by the user prior to, during or after injection. Prior to and after injection, the needle is hidden in the device so as to avoid any potential injury or health risk to the user or health care provider. The injector includes a housing and a shield arranged to slide relative to the housing and a driver moving during drug delivery. The housing and shield form a cartridge enclosure. The cartridge is shielded and locked after delivery is completed. A needle-locking mechanism can be used in any number of pen-like injectors or safety needles.

70 Claims, 60 Drawing Sheets

U.S. PATENT DOCUMENTS

| | | | |
|---|---|---|---|
| 3,066,670 A * | 12/1962 | Stauffer | 604/139 |
| 3,182,660 A * | 5/1965 | Weydanz et. al. | 604/139 |
| 3,542,023 A | 11/1970 | Ogle | |
| 3,702,609 A * | 11/1972 | Steiner | 604/139 |
| 3,742,948 A * | 7/1973 | Post et al. | 604/139 |
| 3,811,441 A | 5/1974 | Sarnoff | |
| 3,867,938 A | 2/1975 | Radcliffe | |
| 3,880,163 A * | 4/1975 | Ritterskamp | 604/136 |
| 3,889,673 A | 6/1975 | Dovey et al. | |
| 3,895,633 A | 7/1975 | Bartner et al. | |
| 4,031,890 A | 6/1977 | Homan | |
| 4,031,893 A | 6/1977 | Kaplan et al. | |
| 4,254,768 A | 3/1981 | Ty | |
| 4,316,463 A * | 2/1982 | Schmitz et al. | 604/135 |
| 4,328,802 A | 5/1982 | Curley et al. | |
| 4,378,015 A | 3/1983 | Wardlaw | |
| 4,427,039 A | 1/1984 | Brooks et al. | |
| 4,445,510 A | 5/1984 | Rigby | |
| 4,468,220 A | 8/1984 | Willbanks | |
| 4,553,962 A | 11/1985 | Brunet | |
| 4,624,393 A | 11/1986 | Lopez | |
| 4,645,073 A | 2/1987 | Homan | |
| 4,689,042 A | 8/1987 | Sarnoff et al. | |
| 4,713,061 A | 12/1987 | Tarello et al. | |
| 4,723,937 A * | 2/1988 | Sarnoff et al. | 604/90 |
| 4,738,660 A | 4/1988 | Lucas | |
| 4,747,839 A | 5/1988 | Tarello et al. | |
| 4,755,169 A | 7/1988 | Sarnoff et al. | |
| 4,838,857 A | 6/1989 | Strowe et al. | |
| 4,861,335 A | 8/1989 | Reynolds | |
| 4,886,495 A | 12/1989 | Reynolds | |
| 4,900,307 A | 2/1990 | Kulli | |
| 4,904,242 A | 2/1990 | Kulli | |
| 4,923,447 A | 5/1990 | Morgan | |
| 4,927,414 A | 5/1990 | Kulli | |
| 4,929,241 A | 5/1990 | Kulli | |
| 4,938,742 A | 7/1990 | Smits | |
| 4,941,880 A | 7/1990 | Burns | |
| 4,968,299 A * | 11/1990 | Ahlstrand et al. | 604/90 |
| 4,969,874 A | 11/1990 | Michel et al. | |
| 5,013,303 A | 5/1991 | Tamari et al. | |
| 5,024,656 A | 6/1991 | Gasaway et al. | |
| 5,092,842 A * | 3/1992 | Bechtold et al. | 604/135 |
| 5,106,374 A | 4/1992 | Apperson et al. | |
| 5,114,406 A * | 5/1992 | Gabriel et al. | 604/136 |
| 5,137,511 A | 8/1992 | Reynolds | |
| 5,156,599 A * | 10/1992 | Ranford et al. | 604/198 |
| 5,163,909 A | 11/1992 | Stewart | |
| 5,169,388 A | 12/1992 | McPhee | |
| 5,180,370 A | 1/1993 | Gillespie | |
| 5,188,599 A | 2/1993 | Botich et al. | |
| 5,201,708 A | 4/1993 | Martin | |
| 5,244,465 A | 9/1993 | Michel | |
| 5,267,963 A | 12/1993 | Bachynsky | |
| 5,279,581 A * | 1/1994 | Firth et al. | 604/198 |
| 5,281,198 A | 1/1994 | Haber et al. | |
| 5,295,965 A * | 3/1994 | Wilmot | 604/136 |
| 5,300,030 A * | 4/1994 | Crossman et al. | 604/136 |
| 5,304,128 A | 4/1994 | Haber et al. | |
| 5,318,538 A * | 6/1994 | Martin | 604/110 |
| 5,320,603 A | 6/1994 | Vetter et al. | |
| 5,320,609 A * | 6/1994 | Haber et al. | 604/135 |
| 5,334,162 A | 8/1994 | Harris | |
| 5,342,319 A | 8/1994 | Watson et al. | |
| 5,342,320 A | 8/1994 | Cameron | |
| 5,360,410 A | 11/1994 | Wacks | |
| 5,391,151 A | 2/1995 | Wilmot | |
| 5,407,431 A | 4/1995 | Botich et al. | |
| 5,407,436 A | 4/1995 | Toft et al. | |
| 5,411,489 A | 5/1995 | Pagay et al. | |
| 5,433,704 A | 7/1995 | Ross et al. | |
| 5,454,786 A | 10/1995 | Harris | |
| 5,460,611 A | 10/1995 | Alexander | |
| 5,462,525 A | 10/1995 | Srisathapat et al. | |
| 5,472,430 A | 12/1995 | Vaillincourt et al. | |
| 5,478,316 A * | 12/1995 | Bitdinger et al. | 604/135 |
| 5,480,387 A * | 1/1996 | Gabriel et al. | 604/134 |
| 5,489,266 A | 2/1996 | Grimard | |
| 5,514,097 A * | 5/1996 | Knauer | 604/136 |
| 5,531,683 A | 7/1996 | Kriesel et al. | |
| 5,540,665 A | 7/1996 | Mercado et al. | |
| 5,545,143 A | 8/1996 | Fischell | |
| 5,545,147 A * | 8/1996 | Harris | 604/209 |
| 5,566,729 A | 10/1996 | Grabenkort et al. | |
| 5,591,136 A * | 1/1997 | Gabriel | 604/211 |
| 5,599,309 A * | 2/1997 | Marshall et al. | 604/136 |
| 5,611,779 A | 3/1997 | Saito et al. | |
| 5,637,094 A * | 6/1997 | Stewart et al. | 604/135 |
| 5,643,214 A * | 7/1997 | Marshall et al. | 604/134 |
| 5,658,259 A * | 8/1997 | Pearson et al. | 604/232 |
| 5,681,291 A * | 10/1997 | Galli | 604/192 |
| 5,681,292 A | 10/1997 | Tober et al. | |
| 5,688,251 A * | 11/1997 | Chanoch | 604/208 |
| 5,695,472 A * | 12/1997 | Wyrick | 604/136 |
| 5,709,668 A * | 1/1998 | Wacks | 604/232 |
| 5,713,872 A | 2/1998 | Feuerborn et al. | |
| 5,746,215 A | 5/1998 | Manjarrez | |
| 5,746,714 A | 5/1998 | Salo et al. | |
| 5,779,668 A | 7/1998 | Grabenkort | |
| 5,779,677 A | 7/1998 | Frezza | |
| 5,785,682 A | 7/1998 | Grabenkort | |
| 5,788,677 A | 8/1998 | Botich et al. | |
| 5,882,342 A | 3/1999 | Cooper et al. | |
| 5,910,130 A * | 6/1999 | Caizza et al. | 604/110 |
| 5,928,205 A | 7/1999 | Marshall | |
| 6,099,503 A | 8/2000 | Stradella | |
| 6,099,504 A | 8/2000 | Gross et al. | |
| 6,123,688 A | 9/2000 | Botich et al. | |
| 6,146,361 A * | 11/2000 | DiBiasi et al. | 604/232 |
| 6,149,626 A | 11/2000 | Bachynsky | |
| 6,159,181 A * | 12/2000 | Crossman et al. | 604/157 |
| 6,200,296 B1 * | 3/2001 | Dibiasi et al. | 604/272 |
| 6,210,369 B1 | 4/2001 | Wilmot et al. | |
| 6,221,046 B1 | 4/2001 | Burroughs et al. | |
| 6,228,067 B1 * | 5/2001 | Gabriel | 604/211 |
| 6,280,421 B1 * | 8/2001 | Kirchhofer et al. | 604/218 |
| 6,319,233 B1 * | 11/2001 | Jansen et al. | 604/192 |
| 6,319,234 B1 * | 11/2001 | Restelli et al. | 604/198 |
| 6,387,078 B1 | 5/2002 | Gillespie et al. | |
| 6,419,658 B1 * | 7/2002 | Restelli et al. | 604/110 |
| 6,544,234 B1 * | 4/2003 | Gabriel | 604/207 |
| 6,620,137 B2 | 9/2003 | Kirchhofer et al. | |
| 6,743,203 B1 * | 6/2004 | Pickhard | 604/139 |
| 6,805,686 B1 * | 10/2004 | Fathallah et al. | 604/135 |
| 7,066,907 B2 * | 6/2006 | Crossman et al. | 604/110 |
| 7,097,634 B2 * | 8/2006 | Gilbert | 604/150 |
| 2001/0005781 A1 | 6/2001 | Bergens et al. | |
| 2002/0120235 A1 * | 8/2002 | Enggaard | 604/135 |
| 2002/0156426 A1 * | 10/2002 | Gagnieux et al. | 604/197 |
| 2002/0161337 A1 * | 10/2002 | Shaw et al. | 604/197 |
| 2002/0177819 A1 * | 11/2002 | Barker et al. | 604/232 |
| 2002/0193746 A1 * | 12/2002 | Chevallier | 604/197 |
| 2003/0050606 A1 * | 3/2003 | Brand et al. | 604/197 |
| 2003/0093036 A1 * | 5/2003 | Crossman et al. | 604/197 |
| 2003/0105430 A1 * | 6/2003 | Lavi et al. | 604/136 |
| 2003/0229314 A1 * | 12/2003 | McWethy et al. | 604/197 |
| 2004/0019326 A1 * | 1/2004 | Gilbert et al. | 604/135 |
| 2005/0027255 A1 * | 2/2005 | Lavi et al. | 604/135 |

FOREIGN PATENT DOCUMENTS

| | | |
|---|---|---|
| DE | 4120267 A1 | 12/1992 |
| EP | 0186916 B1 | 12/1988 |
| EP | 0516473 A1 | 12/1992 |

| EP | 0518416 A1 | 12/1992 |
| EP | 0666084 | 8/1995 |
| FR | 986154 | 7/1951 |
| FR | 2506151 | 11/1982 |
| FR | 2616221 | 12/1988 |
| FR | 2770404 | 5/1999 |
| FR | 2778852 | 11/1999 |
| WO | 94/21213 | 9/1994 |
| WO | 94/28964 | 12/1994 |
| WO | 96/19252 | 6/1996 |
| WO | 99/10030 | 3/1999 |
| WO | 99/33504 | 7/1999 |
| WO | 00/09186 | 2/2000 |
| WO | 0050107 | 8/2000 |
| WO | 00/62839 | 10/2000 |
| WO | 00/69494 | 11/2000 |
| WO | 03/015855 | 2/2003 |

* cited by examiner

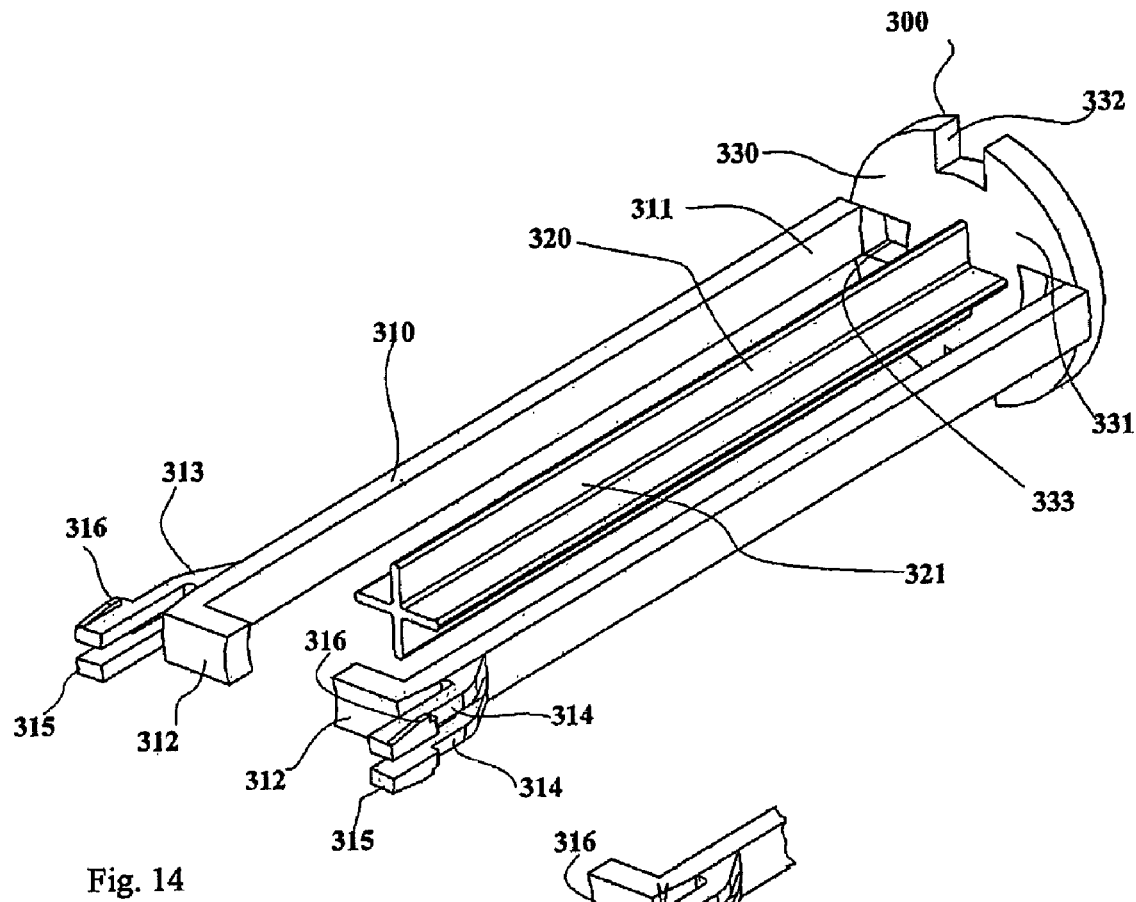
Fig. 14
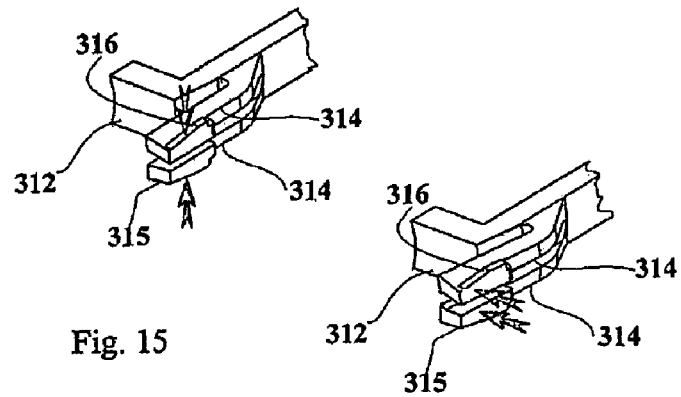
Fig. 15
Fig. 16

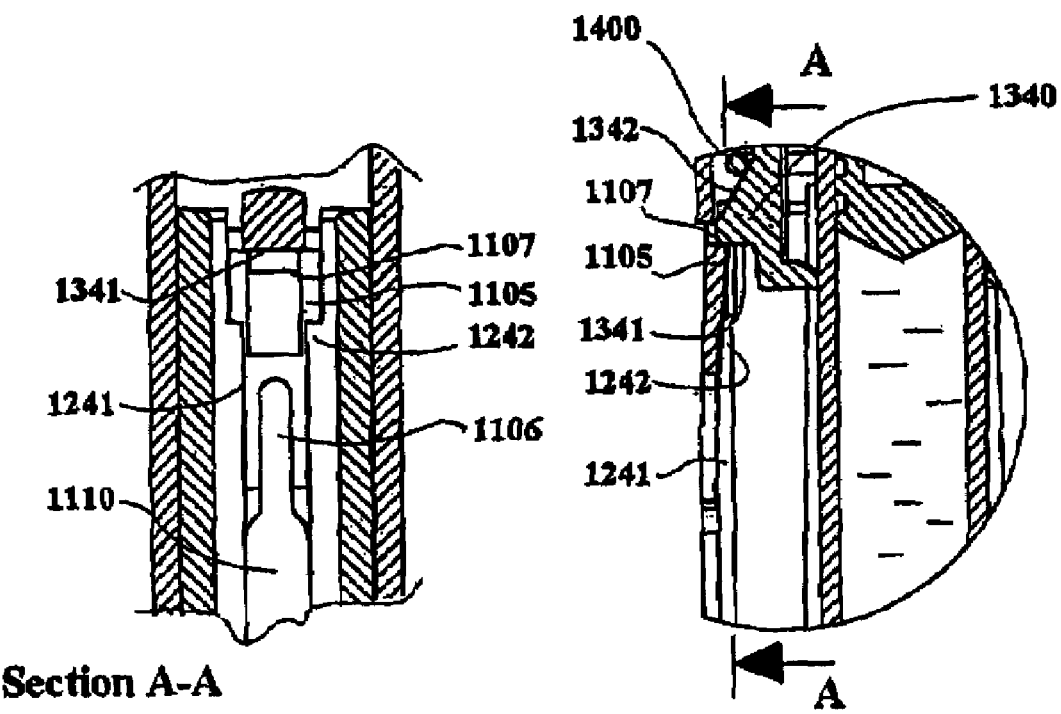
Fig. 72
Section A-A
Fig. 70
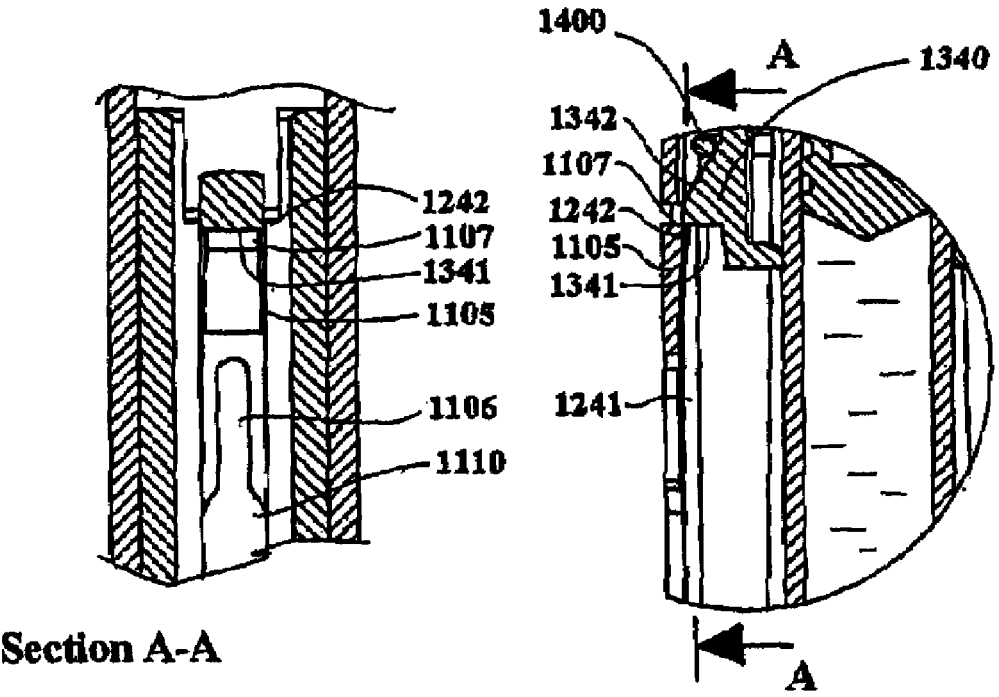
Fig. 73
Section A-A
Fig. 71

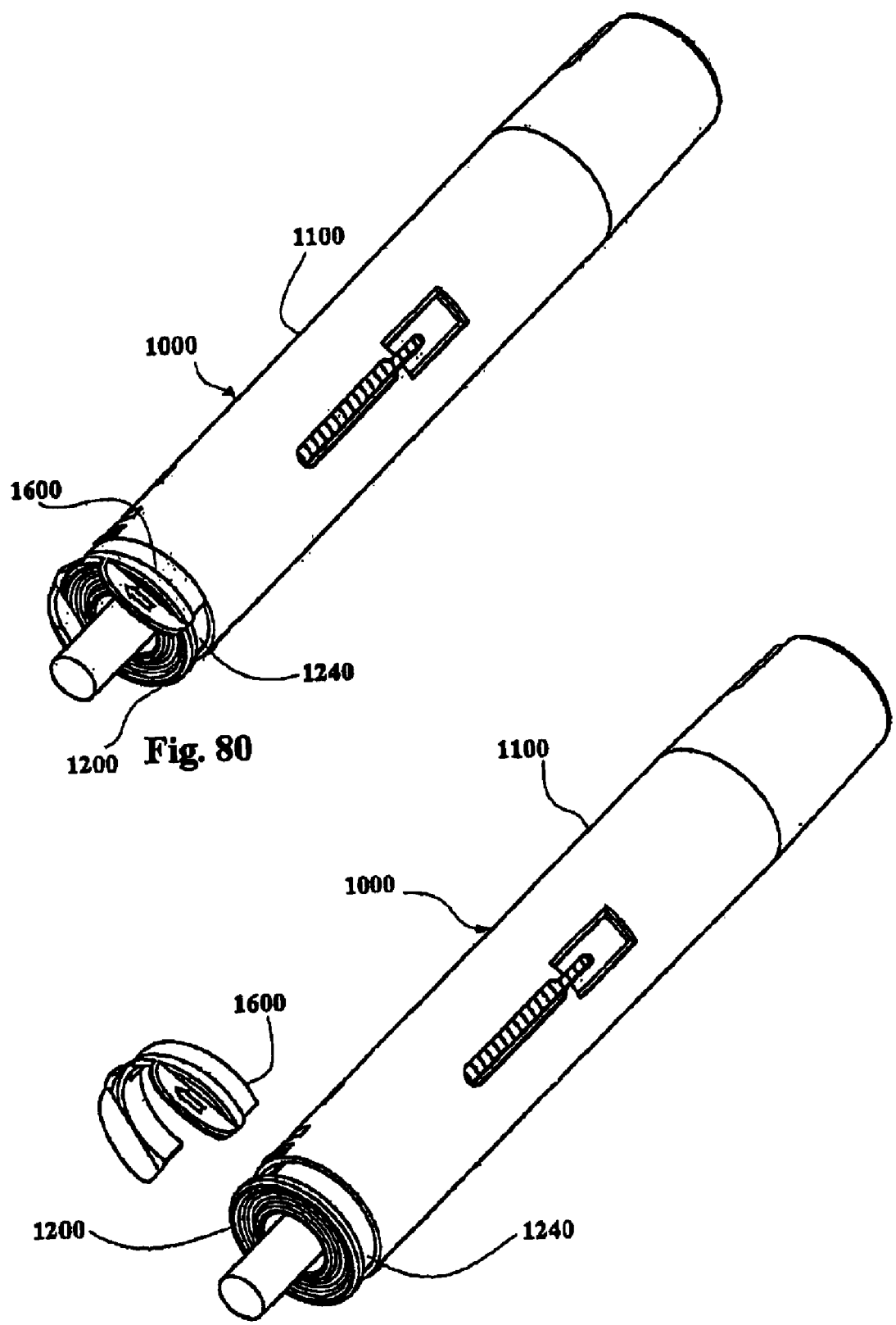

INJECTING APPARATUS

BACKGROUND OF THE INVENTION

1. Field of the Invention

This invention relates to the preparation and administration of a product into a living organism (e.g. the human body), and more particularly to an apparatus for automatically and safely delivering the product.

2. Description of Related Art

Previously, various devices have been developed for the delivery of medications into and through the skin of living organisms. These devices include syringes in which a liquid drug solution is delivered through the skin of a user from a syringe chamber by movement of a syringe plunger to move the drug solution from a syringe chamber through a syringe needle inserted under the skin. The drug solution is generally in liquid form, and can be a mixture of the drug (e.g. powdered, lyophilized, concentrated liquid) and a diluent (e.g. dextrose solution, saline solution, water).

It is well known that many people are apprehensive about receiving an injection from a needle. This problem is even more significant for those who must administer their own medication. It is known that needle phobia can be minimized by hiding the needle before, during and after delivery. It is therefore preferable that the person who receives the drug should not see the needle, which often triggers the fear of needle insertion.

It is also preferable for the needle to be protected before and after delivery of the drug. While a needle can be protected with a removable cap, it is preferable for the needle to be secured within the delivery device before the needle is inserted through the patient's skin and after the needle is shielded. Preferably the needle is enclosed in the device after use and locked into final position after injection.

The needle insertion is assisted by the user or caregiver or is automatic, whilst its shielding is automatic, so that the user does not prematurely expose the needle for injection or have to guess when delivery is completed.

It is also preferable for such a device to provide indications for assisting in the correct use of the automatic injector. Indications could be visual, audible or tactile and are provided at the start or completion of any stage of system use.

A user or patient could be injured if an injection device were activated prematurely. Generally, such a device projects its needle from the end of a barrel and ejects the dose. Such actions can cause injury if the needle pierces another person or is injected into an undesired area of the patient (e.g., an eye). Accordingly, it is advantageous if the needle is in a safe location before and after use to prevent accidental injury or contamination.

It is further desirable to have a simple, reliable system that facilitates safe preparation and delivery of a drug. Dosage amounts may vary from one patient to another. At present, there is no easy way for a patient to self-administer a dosage of drug via an automatic injection system where the dosage amount may be easily changed prior to delivery and easily delivered. Moreover, there is a need to further improve the ability of the user to minimize residual drug in the container or system. Also, there is a need to enable the user to eliminate any air bubbles that may be trapped in the drug container prior to use.

It is also desirable to provide a delivery system where the dosage for delivery is easily viewed by the patient prior and after use. The user's inability to see the dosage form prior to use creates a significant sense of unease in the user in that the user wants to ensure that the proper dosage is in the system and ready for delivery. More importantly, the users inability to see the dosage form prior to use leaves the user concerned that the dosage may be faulty, or, for example, have foreign particles trapped and if present, may result in injury or harm to the user.

The user's inability to view the dosage being delivered and the end of delivery leaves the user with a level of uncertainty as to the amount delivered and the delivery being completed. Thus, it is extremely important to the user's peace of mind to provide an area in which to view the dosage prior to and after delivery. As will be discussed in detail later, the injection device of the present application provides this opportunity.

Further, it is desirable to provide a delivery system that is easy to use at a low cost. Moreover, it is desirable to provide a system that is easy to integrate with the drug container, thereby providing flexibility in meeting the requirements of different drug containers like pre-filled syringes/cartridges. For example, it is important to accommodate standard cartridges with a needle cover including a rigid plastic cover. Moreover, it is desirable to have a system that can accommodate cartridges filled on standard filling lines. It is desirable to provide a system characterized by a small number of components indicating low product costs.

The following are exemplary existing automatic injectors.

U.S. Pat. Nos. 5,114,406 (Gabriel, et al.); and 6,544,234 (Gabriel) disclose a plunger which is telescopically received within a tubular element causing the needle penetration, drug delivery and securing the needle. Beside it being a telescope type mechanism the system is using two springs and the detection of end of delivery is controlled by packaging parts and not by the cartridge only.

U.S. Pat. No. 5,599,309 (Marshall, et al.) discloses an injector having a drive member held in a rearward primed position by a detent provided in the body of the device. When the device is applied to a patients skin and a rear end cap is pressed forwardly, the forward ends of ribs wedge tongues inward (or pivot) until they clear the detents formed by the forward ends of the slots. A coil spring shoots a cylinder forward for injection and delivery. This invention is involving the packaging parts in order to detect end of delivery and is using two springs—one to penetrate and deliver and the second to shield.

U.S. Pat. No. 6,159,181 (Crossman, et al.) and U.S. Patent Publication Nos. 2003/0093036 and 2003/0105430 (Crossman, et al.) are mechanisms to deliver drugs in a parenteral method and to shield the penetrating needle after use. Both mechanisms use double springs and do not use the cartridge to detect the end of delivery. In 2003/0093036 (Crossman, et al.) the user is expected to manually trigger the needle shield and to decide when to do that. The evolution between these two applications is in making the device simpler and more accurate. Nevertheless, the basic principles remain the same.

The following exemplary patents are mentioned as they relate to needle retraction mechanisms. Several disclose axially-aligned spring-driven needle extenders and retractors. These include U.S. Pat. Nos. 5,779,677 (Frezza); 6,210,369 (Wilmot, et al); 5,391,151 (Wilmot); 5,637,094 (Stewart, Jr., et al.) and U.S. Patent Publication No. 2001/0005781 (Bergens et al.). In all of these references, the function is served by a set of axially-positioned springs; in some, two springs are in use and in others, such as Stewart's and Bergens, even three springs are used. None of the references includes a mechanism for cartridge-shape detection.

In U.S. Patent Publication No. 20030105430 (Lavi, et al.), the functions are served by a mechanism of ten parts, including two springs. The mechanism performs a combination of slide and rotate move, the end of delivery is detected by the packaging parts and not by the shape of the cartridge. The design is characterized by high complexity and costs.

U.S. Pat. No. 6,743,203 (Pickhard) discloses a device for automatically injecting liquids and comprises an axially-divided housing wherein the parts can be removably assembled. The design employs a cartridge with a separate needle assembly and three springs resulting in high complexity.

SUMMARY OF THE INVENTION

According to the present invention there is provided an injection device comprising a housing having a proximate end and a distal end, the distal end having an opening therein, a shield slideably coupled to the housing at said distal end thereof, a cartridge barrel within the housing, the cartridge barrel having proximate and distal ends, a needle cannula fixed to the distal end of the cartridge barrel or attachment means for fixing a needle cannula to the distal end, a stopper within the cartridge barrel, a driver coupled to the stopper, a spring coupled between the housing and the driver, a driver trigger for retaining the driver fixed to the housing and in which state the spring is in a compressed state, the trigger being actuable in use to release the driver from the housing thereby allowing the spring to urge the driver through the housing and with it the stopper through the cartridge barrel, and a release mechanism for releasing the spring from the driver at some point on its travel through the housing, whereupon the spring engages the shield and urges the shield away from the housing so as to cover the needle cannula.

In an exemplary embodiment, an automatic injector for delivering a fluid includes only five components: a housing, a cartridge, a shield, a driver and a spring. The housing has a proximal end and a distal end, and includes means arranged to activate the injector. The drug cartridge is positioned within the housing and the shield and includes a barrel, a stopper, and a needle extending toward the distal end of the housing. The barrel is arranged to contain a fluid in communication with the needle. The stopper is slidingly located within the barrel for forcing the fluid through the needle upon activation of the injector. The driver is in communication with the housing and the shield. The driver is arranged to act on the stopper when disengaged from the housing.

This invention implements the triggering of the device by pushing on the injection site, insertion of the needle by advancing the housing and cartridge, automatic delivery using the driving means, automatic end of delivery sensing mechanism using the shape of the cartridge for detection, and automatic needle extraction and shielding using the same driving means. Simplicity in implementing these functions within the discussed invention is a major difference as compared to other known devices.

The injector also includes a mechanism that automatically shields the cartridge with the needle upon the end of delivery. In addition, this exemplary embodiment of an injector may also include a needle-locking device that locks the needle within the housing after use; further, this exemplary embodiment may include a rod arranged for moving the stopper for titration before delivery; this exemplary embodiment may include a window that allows a user to inspect the dosage before delivery and titrate.

The shield mechanism in this exemplary embodiment might require a well defined force to insert the needle into the tissue. This required force is prolonged in time and travel and is designed to assure the user fully inserts the needle into the tissue based on the inertia of human motion.

The completion of the un-shielding and insertion of the needle results in this exemplary embodiment in an automatic triggering of the injection process. The injection is driven by the energy of the driving means. The injection in this exemplary embodiment is continued until the full content of the cartridge is delivered.

The completion of the delivery results an automatic shielding of the cartridge needle. In this exemplary embodiment the spring bypasses the driver and forces the extraction and shielding of the needle. The shield is automatically moved to a locked position shielding the cartridge needle. An excessive force would be required to overpower the shield retention feature after the shield is placed in the locked, discard position.

Further scope of applicability of the present invention will become apparent in the description given hereafter. However, it should be understood that the detailed description and specific examples, while indicating preferred embodiments of the invention, are given by way of illustration only, since the invention will become apparent to those skilled in the art from this detailed description.

It is desireable to provide an injection device which facilitates automatic insertion of the needle cannula into the skin. This may be achieved by providing means for allowing the driver to drive the cartridge barrel through the housing following activation of said driver trigger and prior to movement of the stopper through the cartridge barrel, thereby urging the needle cannula outward relative to the housing and shield.

The shield mechanism in this exemplary embodiment might require a well defined force to trigger activation of the needle and its insertion into the tissue. This force is selected to assure the user will properly activate the device. The completion of the activation results in this exemplary embodiment in a disengagement of the driver from the housing. This leads to an automatic advancement of the cartridge, needle insertion, and the initiation of the injection process. The cartridge advancement, needle insertion and the injection are all driven by the energy of the driving means. The injection in this exemplary embodiment is continued until the full content of the cartridge is delivered.

BRIEF DESCRIPTION OF THE DRAWINGS

FIG. 14 is an isometric view of the driver of the exemplary embodiment with shield on the housing, when engaged with the housing;

FIG. 15 is a partial isometric view of the deformed driver section of the exemplary embodiment with shield on the housing, which latches during disengagement from the housing;

FIG. 16 is a partial isometric view of the deformed driver section shield on the housing, which latches during delivery;

FIG. 40 also illustrates the alternative embodiment of the mechanism for generating the force profile defined in FIG. 7 and FIG. 8 whereby the driver, driving means, and the cartridge are removed;

FIG. 70 is a detail of a cross-section view similar to that of FIG. 53, showing the triggering mechanism in a storage position;

FIG. 71 is a detail of cross-section view similar to that of FIG. 55, showing the triggering mechanism as triggered;

FIG. 72 is a detail of cross-section view as per section line A-A in FIG. 70, showing the triggering mechanism in a storage position;

FIG. 73 is a detail of cross-section view as per section line A-A in FIG. 71, showing the triggering mechanism as triggered;

FIG. 80 is a view of the embodiment having a safety tab; and

FIG. 81 is a view of the embodiment in FIG. 80 showing the injector and the safety tab after the tab removal from the device.

DETAILED DESCRIPTION OF THE INVENTION

The present invention is directed to automatic injectors and needle-locking devices. The injector is automatic in that the needle at a distal end of the injector is unshielded with the user assistance; the needle is inserted into the injection site (e.g., a patient's skin) with the user assistance; delivery is automatically initiated upon insertion of the needle, and the needle is automatically shielded after the end of delivery. The exemplary injectors include a tight relationship between the position of the shield and the force required for its displacement. Moreover, the exemplary injectors include a rod that provides titration as described below.

The term distal refers to the end or direction of the injector that is applied to an injection site for delivery. The term proximal refers to the end of the injector that is opposite the distal end. The exemplary embodiments show each injector having a distal end from which the needle is exposed for delivery, and a proximal end opposite the distal end.

Preferably the needle is not seen by the user prior to, during or after injection. Prior to and after injection, the needle is covered and/or protected by the shield so as to avoid any potential injury or health risk to the user or health care provider.

Without being limited to any particular theory, the needle-shielding mechanism can be used in any number of pen-like injectors or other types of injectors or syringes. The needle-shielding mechanism includes a position-dependent controlled shield force that insures a needle assembly is shielded within an injector before use and is in a shielded and locked position after use. For purposes of illustration, the needle-locking device is shown in combination with a drug cartridge inserted in the injector.

Without being limited to a particular theory, the disclosed exemplary embodiments include: (a) a disposable device having a disposable pre-filled cartridge; (b) a disposable pre-filled injector with drug titration (needle concentric to housing), an automatic injector with the shield sliding on the housing and an automatic injector with the shield sliding inside the housing.

Figure 2:
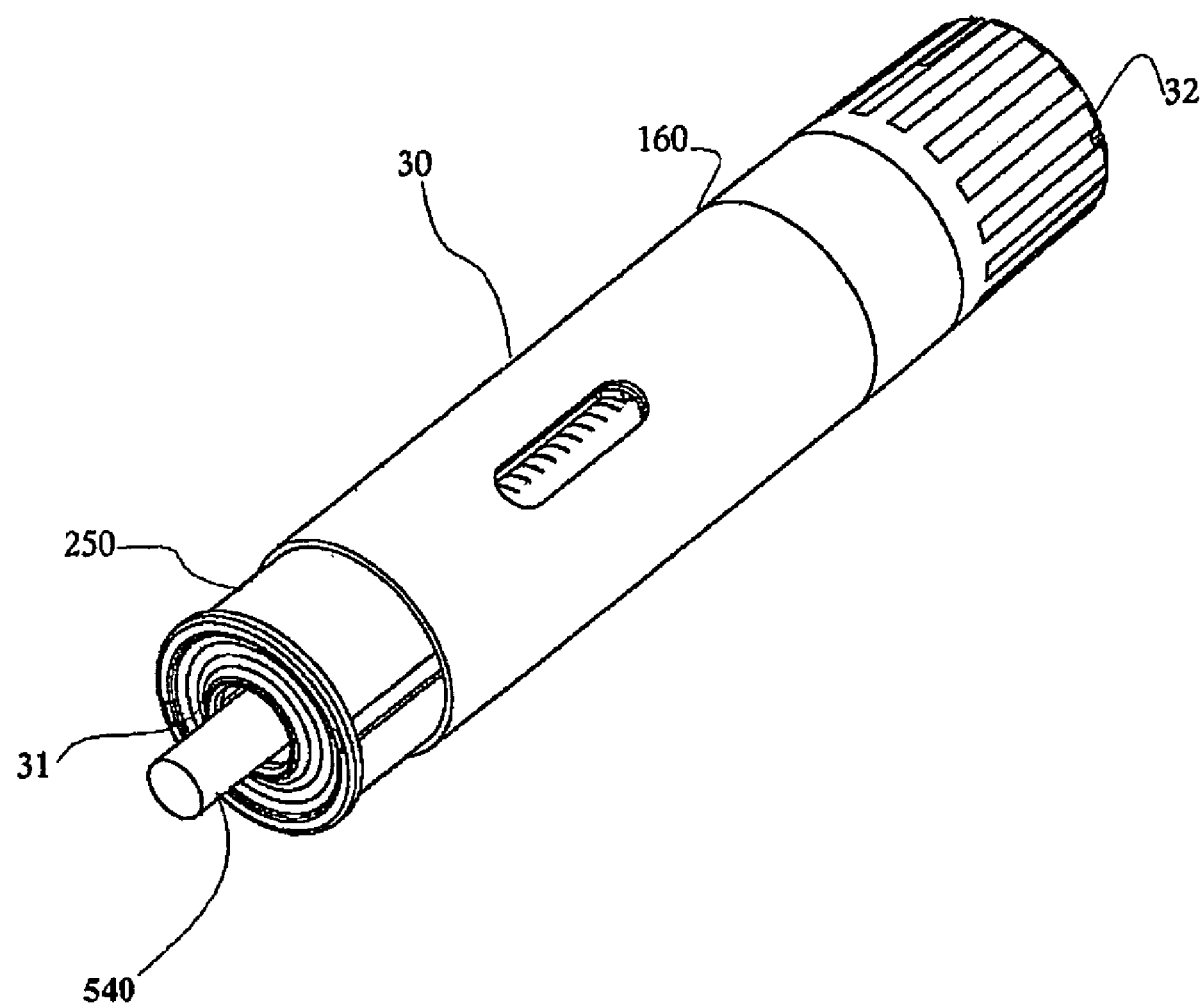
FIG. 2 is an external view showing an injector construed in accordance with another exemplary embodiment of the invention and the shield sliding inside the housing.
Figure 3:
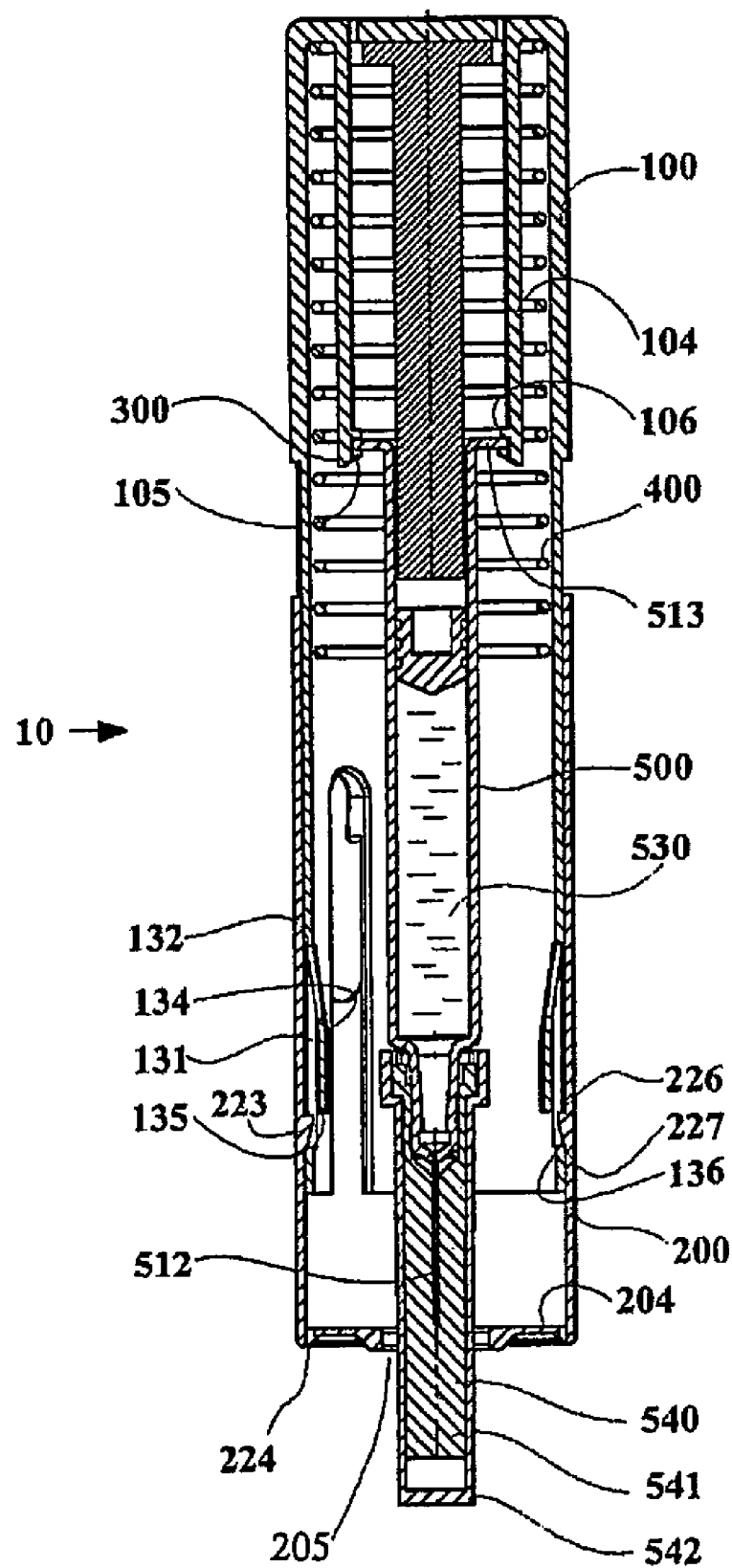
FIG. 3 is a longitudinal section view showing an injector construed in accordance with an exemplary embodiment of the invention, shield on the housing, illustrating the cartridge support by the housing.

Referring to FIGS. 1-50, there is shown at 10 an automatic injector constructed in accordance with an exemplary embodiment of this invention. In particular, the injector 10 includes a housing 100, a shield 200, a driver 300 (FIG. 3), a cartridge 500, and a driving unit 400 (FIG. 3). Preferably, examples of the injector 10 also include a leaf spring 131 (FIG. 3) extending from the housing 100, as will be described in more detail below. In this embodiment, the shield 200 slides on the housing 100.

Referring to FIGS. 1-50, there is shown also at 30 (FIG. 2) an automatic injector constructed in accordance with another exemplary embodiment of this invention whereby the shield 250 slides inside the housing 160. In particular, the injector 30 includes a housing 160, a shield 250, a driver 350, a cartridge 500, and a driving unit 450. Preferably, examples of the injector 30 also include a leaf spring 285 (FIG. 4) extending from the shield 250, as will be described in more detail below.

Figure 1:
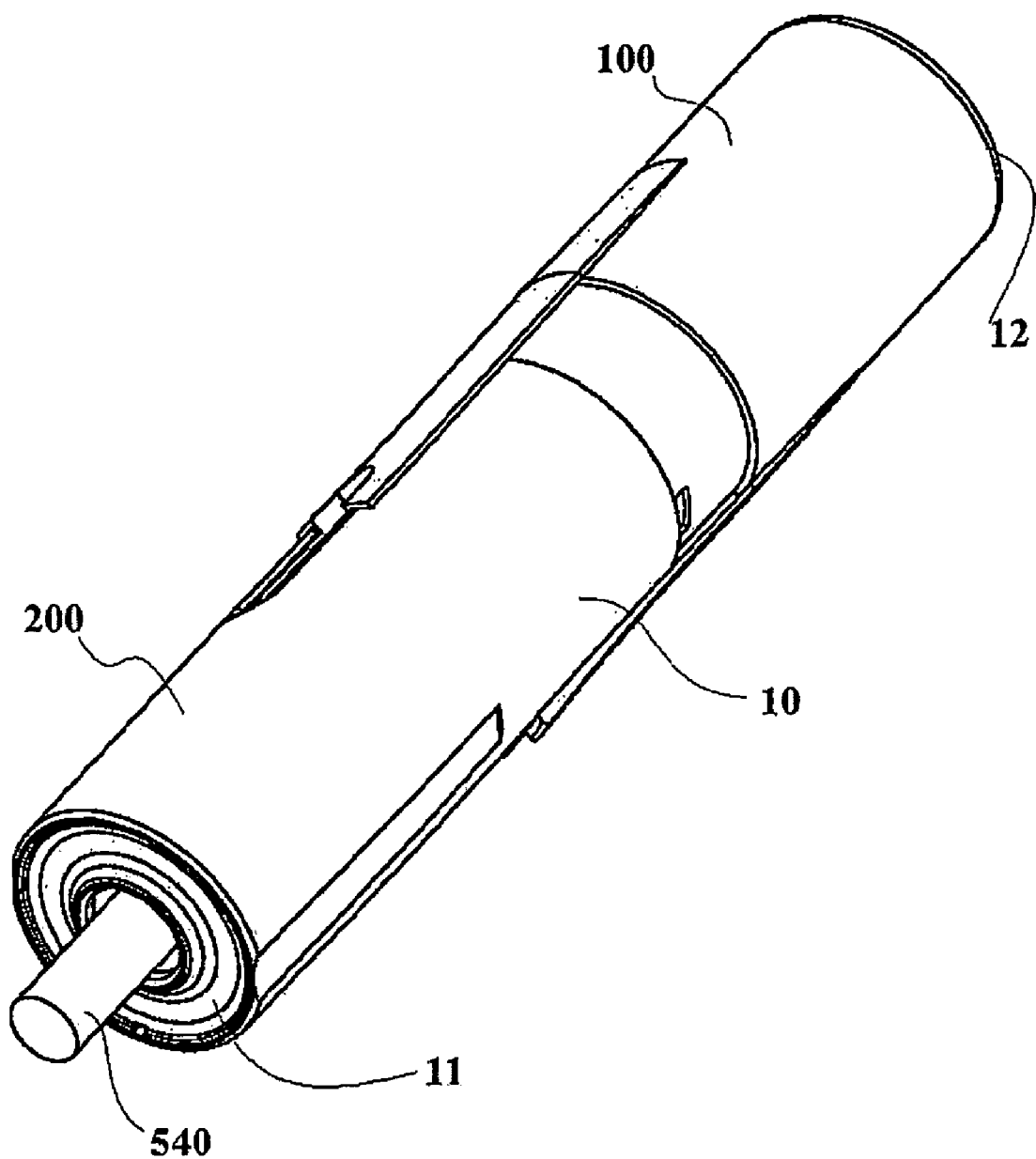
FIG. 1 is an external view showing an injector construed in accordance with an exemplary embodiment of the invention and the shield sliding on the housing.

The housing 100 is interfaced with the shield 200 forming enclosure for the cartridge 500 as is shown in FIG. 3. Externally, the automatic injector 10 represents a pen-like cylindrical structure as is illustrated in FIG. 1. The injector 10 has a distal end 11 from which the needle is exposed for delivery, and a proximal end 12 opposite the distal end 11. Without being limited to a particular theory, the term distal refers to the end or direction of the injector that is applied to the injection site for delivery, and the term proximal refers to the end or direction opposite the distal end or direction.

Figure 4:
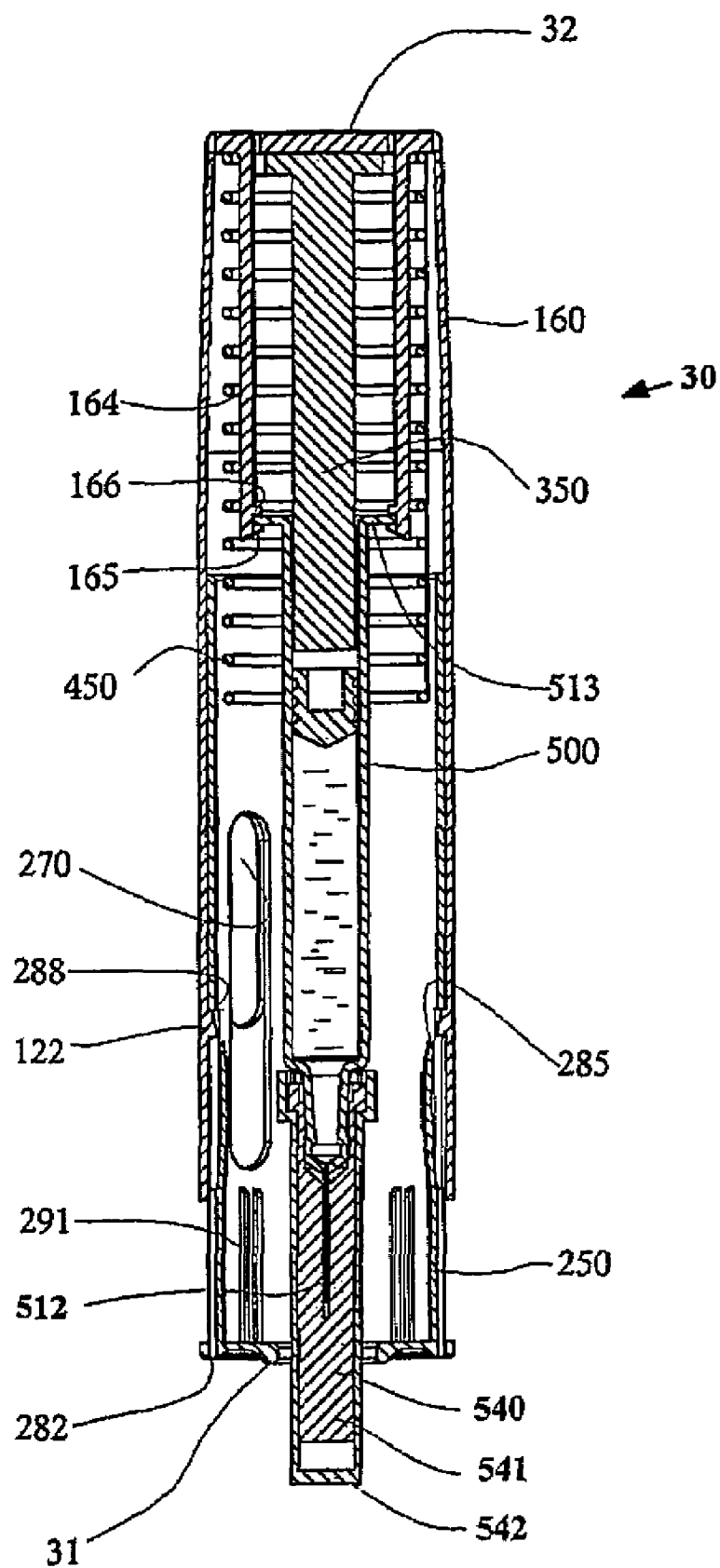
FIG. 4 is a longitudinal section view showing an injector construed in accordance with an exemplary embodiment of the invention, shield inside the housing, illustrating the cartridge support by the housing, and the observation window.

In the exemplary embodiment with the shield 250 sliding in the housing 160, the housing 160 is interfaced with the shield 250 forming enclosure for the cartridge 500, as is shown in FIG. 4. Externally, the automatic injector 30 represents a pen like cylindrical structure as is illustrated in FIG. 2. The injector 30 has a distal end 31 from which the needle is exposed for delivery, and a proximal end 32 opposite the distal end 31. Without being limited to a particular theory, the term distal refers to the end or direction of the injector that is applied to the injection site for delivery, and the term proximal refers to the end or direction opposite the distal end or direction. Both embodiments 10/30, either with the shield sliding on the housing or with the shield sliding inside the housing, retain the basic mechanisms.

Figure 5:
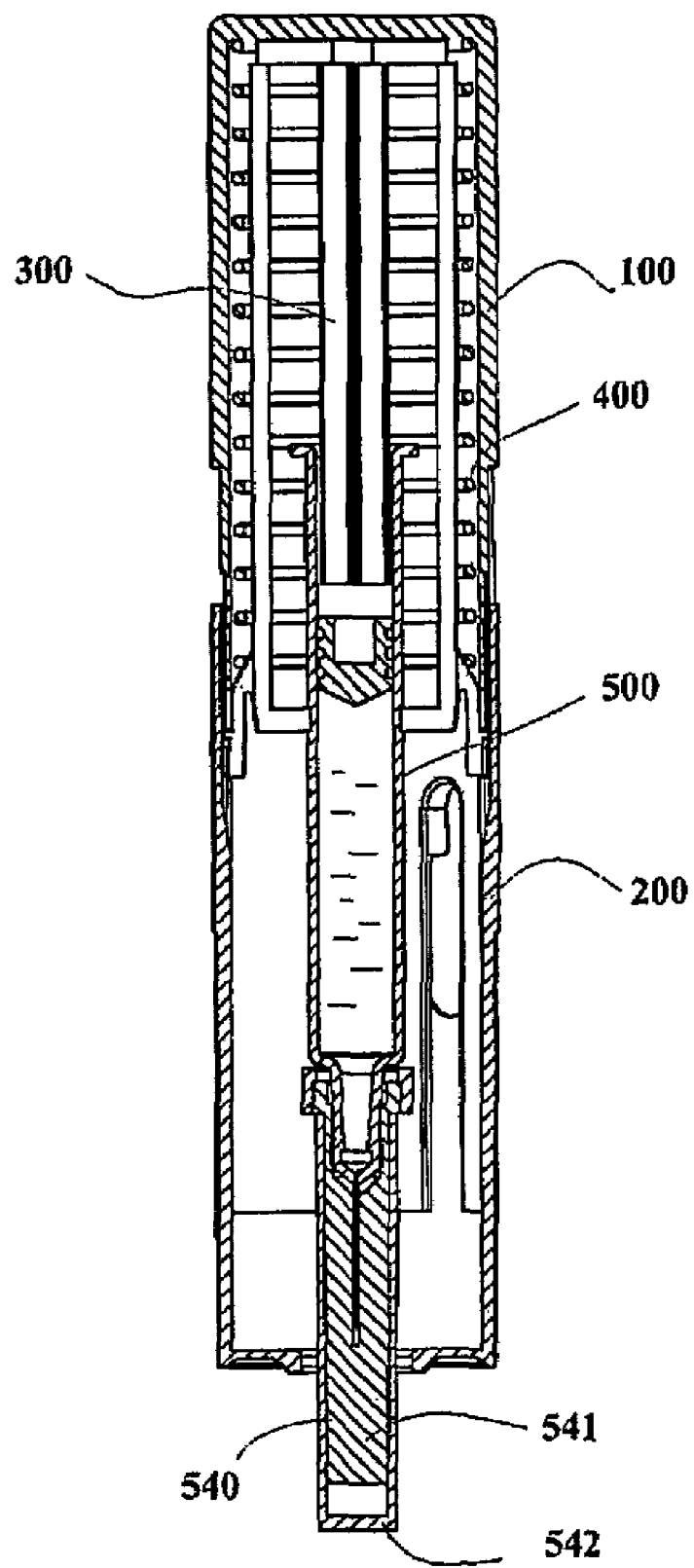
FIG. 5 is a longitudinal section view showing an injector construed in accordance with an exemplary embodiment of the invention, shield on the housing, illustrating the driver.

In the exemplary embodiment 10 with the shield 200 sliding on the housing 100, the housing 100 has a proximal surface equipped with finger like extensions 104 (FIG. 3). These extensions have latches 105 and 106 intended to capture the flanges 513 of the cartridge 500 barrel (see FIG. 3). Furthermore, the housing 100 and the shield 200 form an enclosure that houses the driver 300 and the driving means 400. By way of example only, the driving means may comprise a spring 400, as illustrated in FIG. 3 and FIG. 5. The driver 300 is maintained in its initial position while interlocked with the housing 100. The driver 300 is preloaded by the compressed spring 400.

In the exemplary embodiment 30 with the shield 250 sliding inside the housing 160 the housing 160 has a proximal end surface equipped with finger like extensions 164 (FIG. 4). These extensions have latches 165 and 166 intended to capture the flanges 513 of the cartridge 500 barrel (see FIG. 4). Furthermore, the housing 160 and the shield 250 form an enclosure which is housing the driver 350 and the driving means 450. Preferably, the driving means may comprise a spring 450, as illustrated in FIG. 4. The driver 350 is maintained in its initial position while interlocked with the housing 160. The driver 350 is preloaded by the compressed spring 450.

Figure 6:
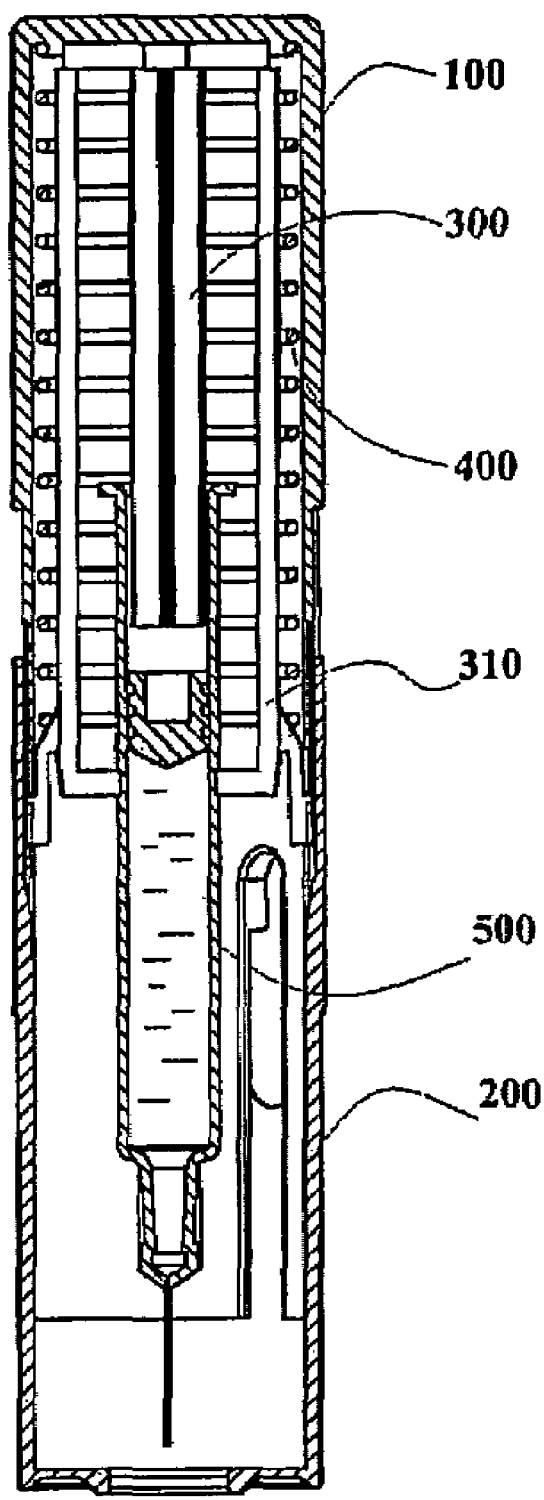
FIG. 6 is a view similar to that of FIG. 5, but showing the injector in a state wherein the protective cap is removed.

The first step in the use of the automatic injector is the removal of the protective cap 540 (needle cover) of the needle 512 illustrated for the shield on housing embodiment. The cap may comprise one component, e.g., an elastomeric protective cap 541. Alternatively, the protective cap 540 may further comprise a second component, e.g., a rigid plastic protective cap 542. The protective cap 540 of the needle 512 protrudes through the distal end of the auto injector (see FIG. 1 and FIG. 2). It is removed from the injector in the first step of use to open the fluid path as illustrated in FIG. 6. The protective cap 540 also protects the shield 200 from accidental impact before use.

The automatic injector of the exemplary embodiments have a minimal number of parts. To achieve the minimal number of components, the initial step of needle deployment (the needle insertion into the tissue) is implemented by the user while pushing the injector toward the injection site. The insertion of the needle automatically triggers the release of the driver and initiates the injection.

Figure 7:
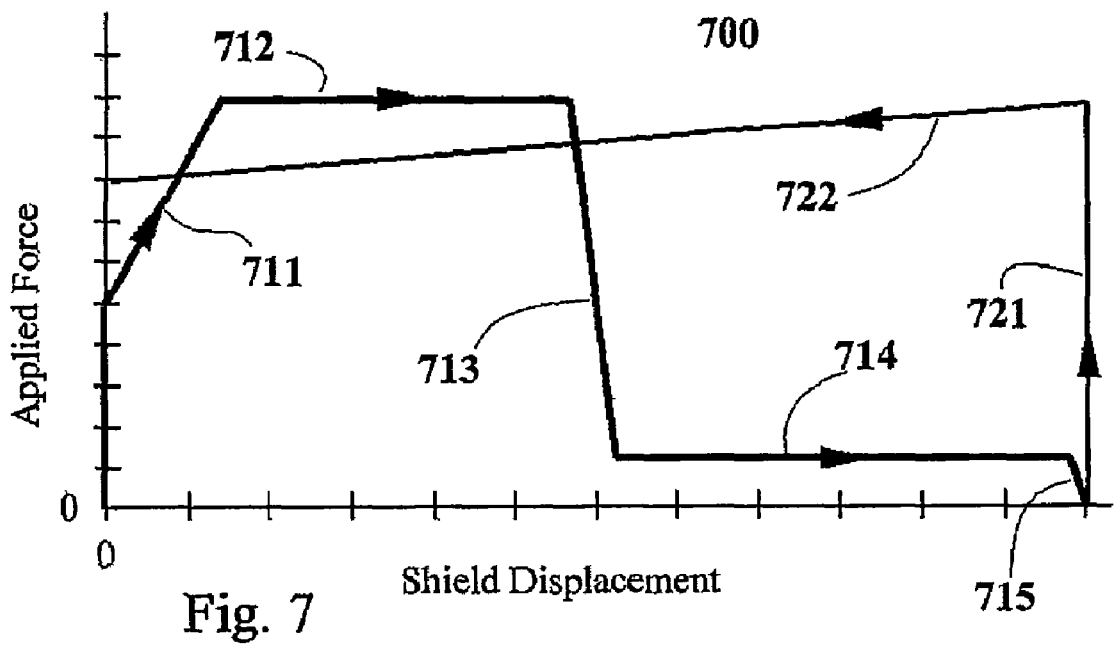
FIG. 7 is a force profile with respect to the shield displacement for an injector construed in accordance with an exemplary embodiments of the invention.

The displacement of the shield while pushing the shield toward the injection site results in the disengagement of the driver from the housing. The displacement of the shield over the initial part of the shield travel requires a substantial force over a short distance as shown in FIG. 7. The force 700 required to displace the shield increases rapidly with the initial displacement 711 of the shield. It remains high during the initial segment of the travel 712 and then rapidly decreases over a short travel distance 713. The shield displacement force remains low over the second part of the travel 714. The force applied by the user to the automatic injector drops to close to zero after the shield is displaced and the needle is fully inserted at 715.

The high initial shield displacement force over a short distance assures that the shield is fully displaced and the needle fully inserted due to the inertia of the human motion. The automatic injector requires from the user about 1 kg of force for the shield displacement over the initial part of the shield travel.

Figure 8:
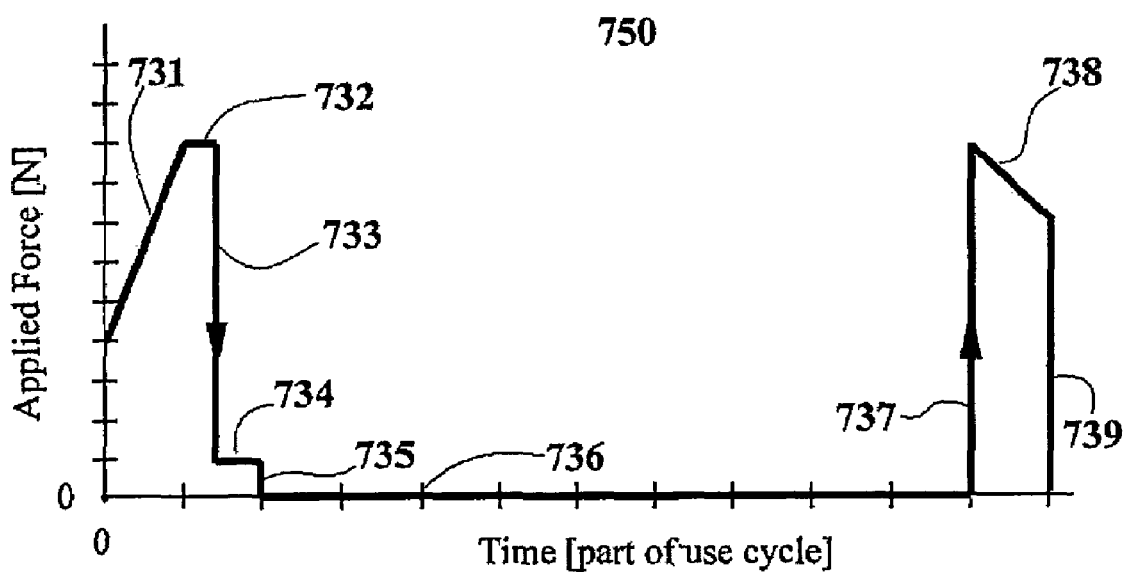
FIG. 8 is a force profile with respect to the injector operation timing for an injector construed in accordance with an exemplary embodiments of the invention.

The profile of the shield displacement force as a function of time 750 is illustrated in FIG. 8. Applied forces of 731, 732, 733, 734 and 735 correspond respectively to displacements 711, 712, 713, 714 and 715.

The driver 300, housing 100 and the shield 200 have a set of features intended to facilitate the disengagement of the driver from the housing at a force defined above. The operation of the automatic injector will become clear from a detailed description of the automatic injector components and component interactions.

Figures 9, 10:
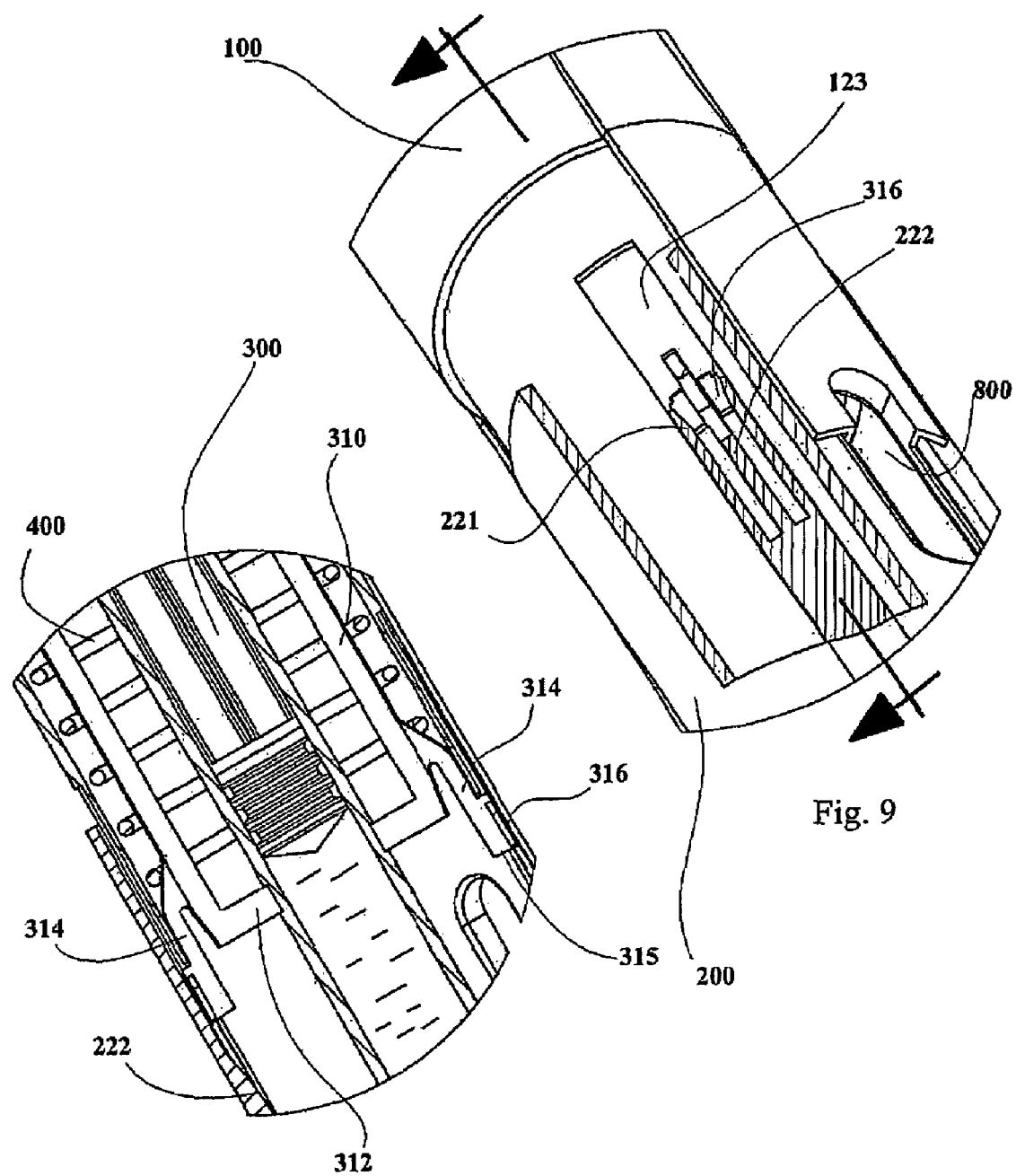
FIG. 9 is a partial external view of the injector, shield on the housing, showing the injector in a state wherein the shield is slightly depressed and a section of the cylindrical part of the shield obscuring the driver is removed.
FIG. 10 is a partial sectional view of the injector as illustrated in FIG. 6, but showing the injector in a state wherein the shield is slightly depressed
Figure 11:
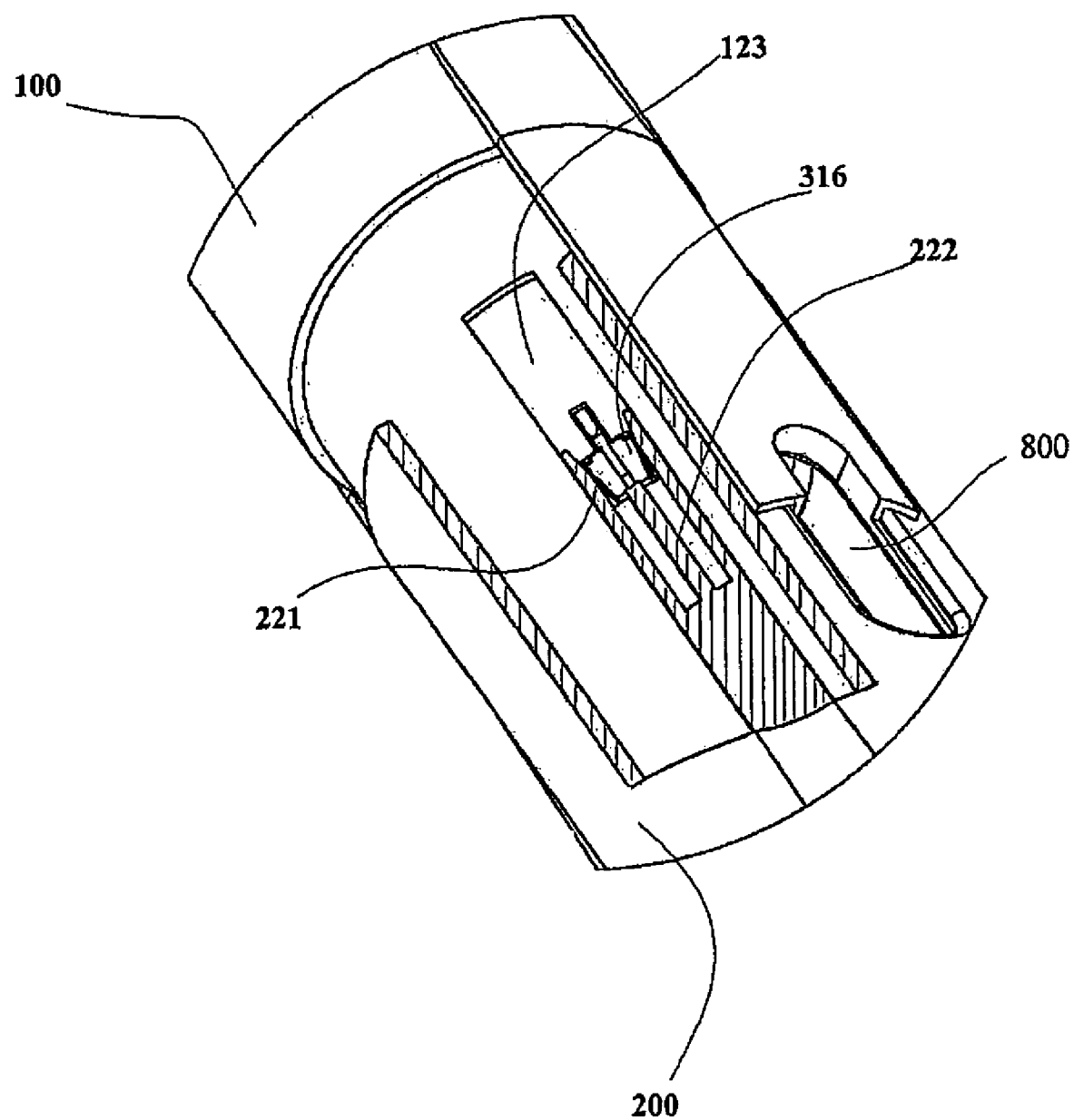
FIG. 11 is a partial external view of the injector showing the injector in a state wherein the shield is further depressed and a section of the cylindrical part of the shield obscuring the driver is removed.

The driver in the exemplary embodiment of the invention with the shield sliding on the housing is initially engaged to the housing as illustrated in FIG. 9 and FIG. 10. The secure engagement prevents an accidental release of the spring due to a potential impact during storage or transportation. The action of shield displacement by the user is preformed in three stages. Initially, the shield rails 221 apply a tangential force to driver fingers pads 316 bringing these together. The direction of the applied force is illustrated in FIG. 15 with arrows. During further motion the shield rail 222 is pushing radially on the latch finger pads 316 (see FIG. 11). The direction of the force is also illustrated in FIG. 16 with arrows. Latch fingers 314 are bent radially eventually disengaging the driver 300 from the housing 100.

Figures 12, 13:
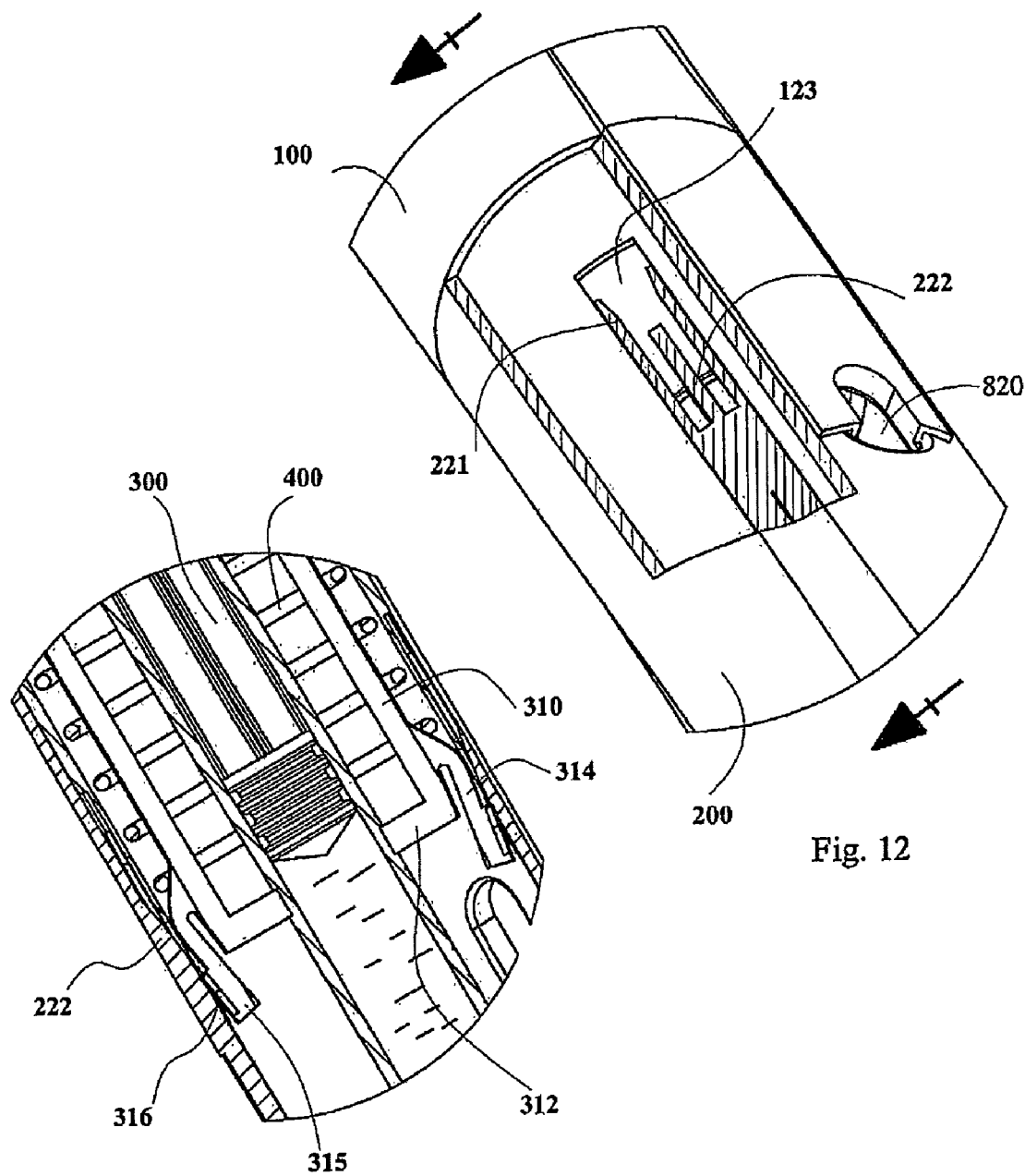
FIG. 12 is a partial external view of the injector showing the injector in a state wherein the shield is fully depressed and a section of the cylindrical part of the shield obscuring the driver is removed.
FIG. 13 is a partial sectional view of the injector as illustrated in FIG. 6, but showing the injector in a state wherein the shield is fully depressed.
Figure 17:
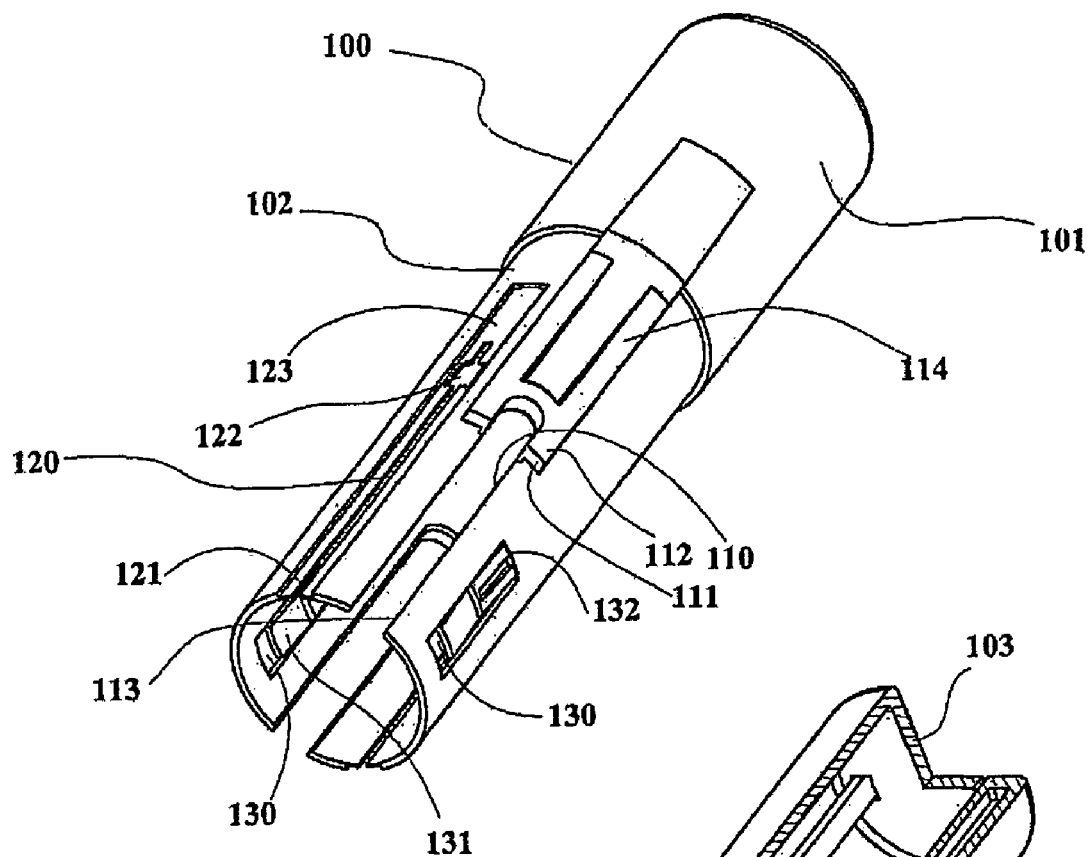
FIG. 17 is an external isometric view of the housing, of the exemplary embodiment with shield on the housing.
Figure 18:
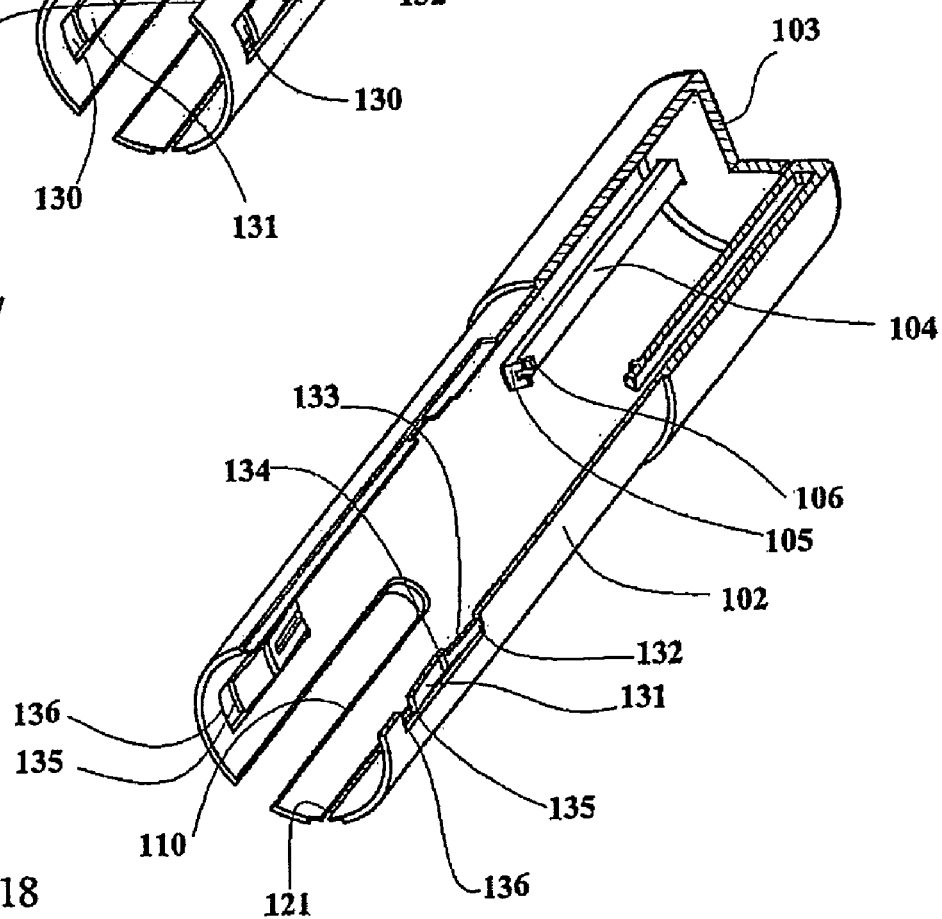
FIG. 18 is an isometric view of the housing with a removed section, of the exemplary embodiment with shield on the housing.
Figures 19, 20:
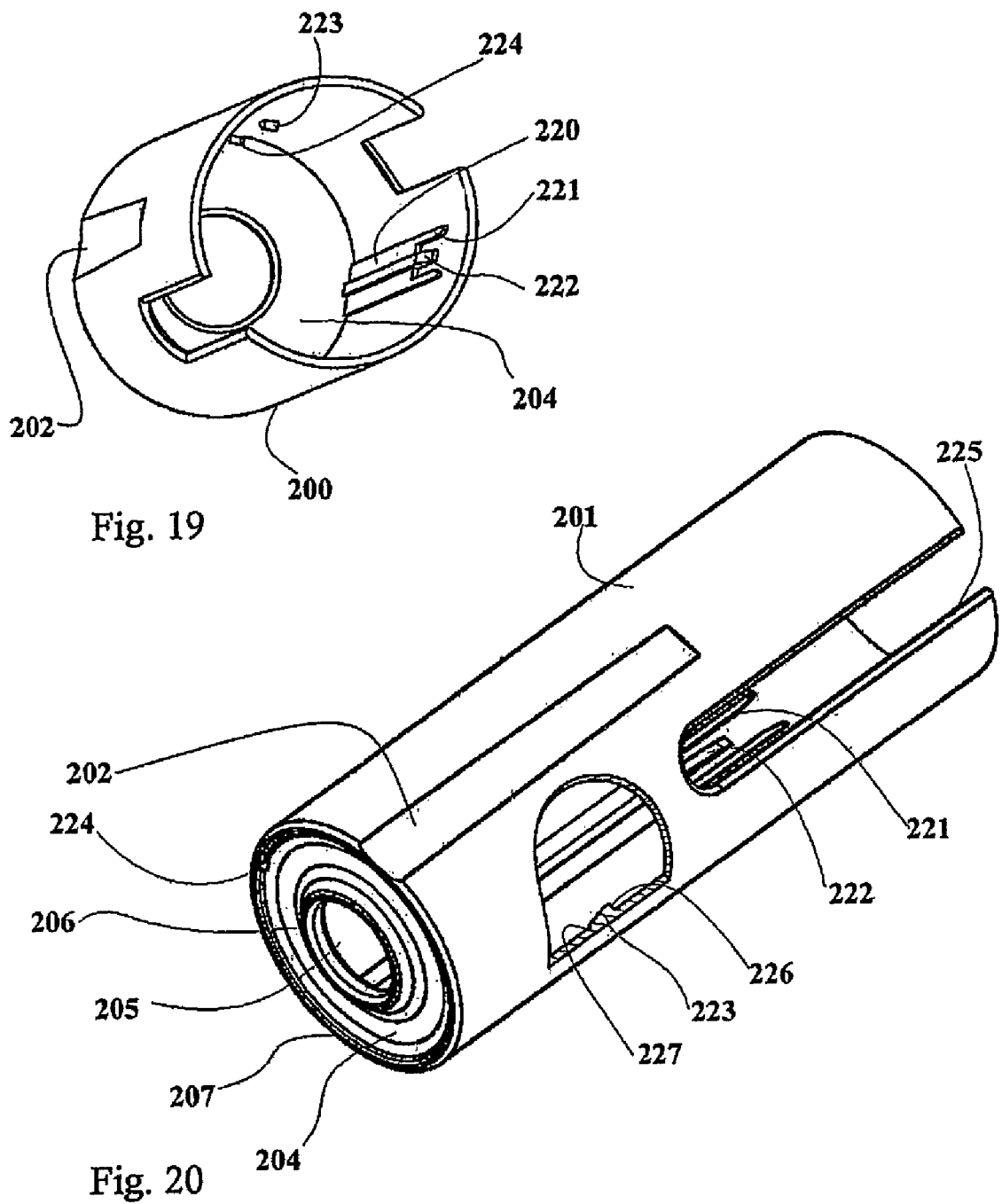
FIG. 19 is an isometric view of the shield from the proximal end, of the exemplary embodiment with shield on the housing.
FIG. 20 is an isometric view of the shield from the distal end, of the exemplary embodiment with the shield on the housing, with a cylindrical section partially removed.
Figure 21:
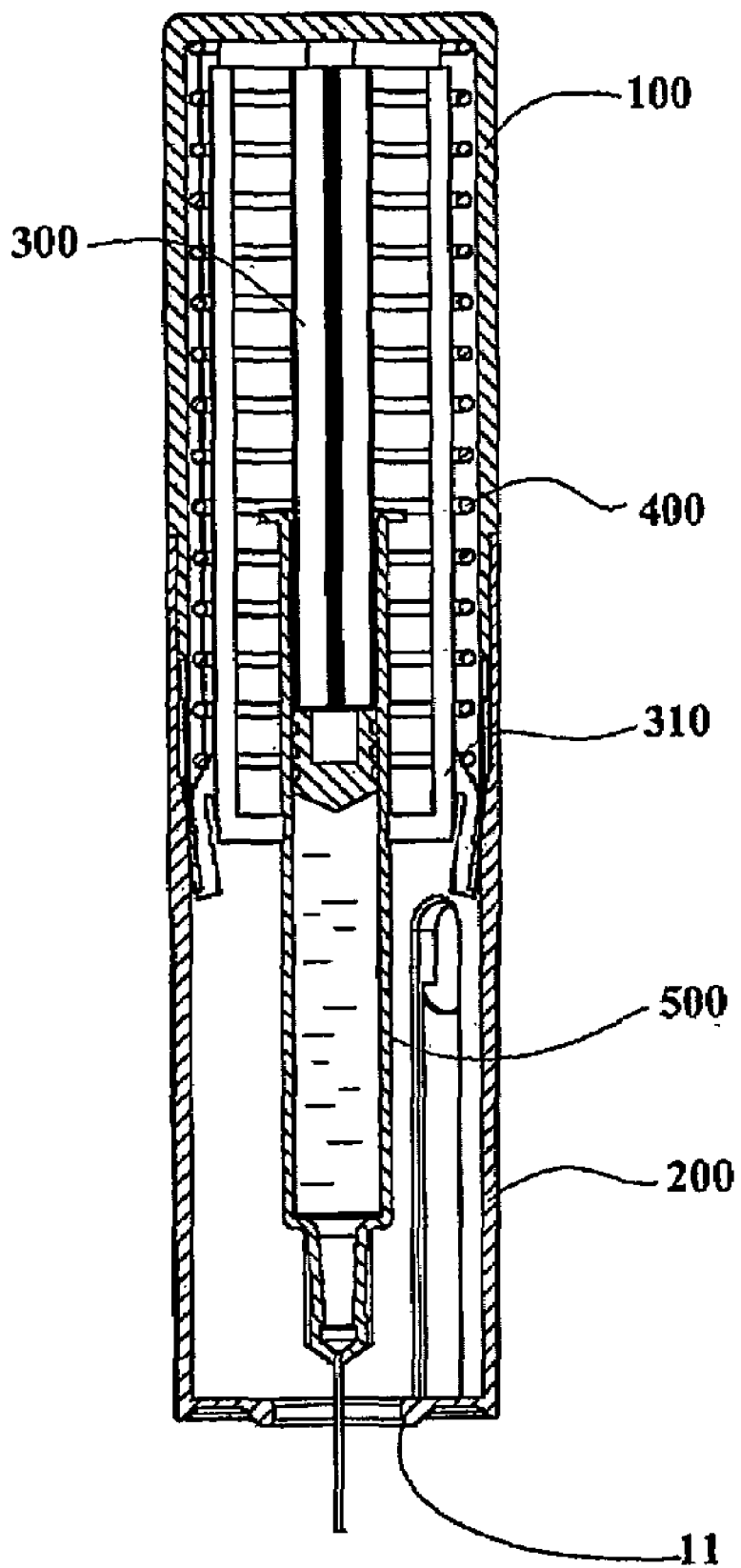
FIG. 21 is a view similar to that of FIG. 6, but showing the injector during the beginning of drug delivery.
Figure 22:
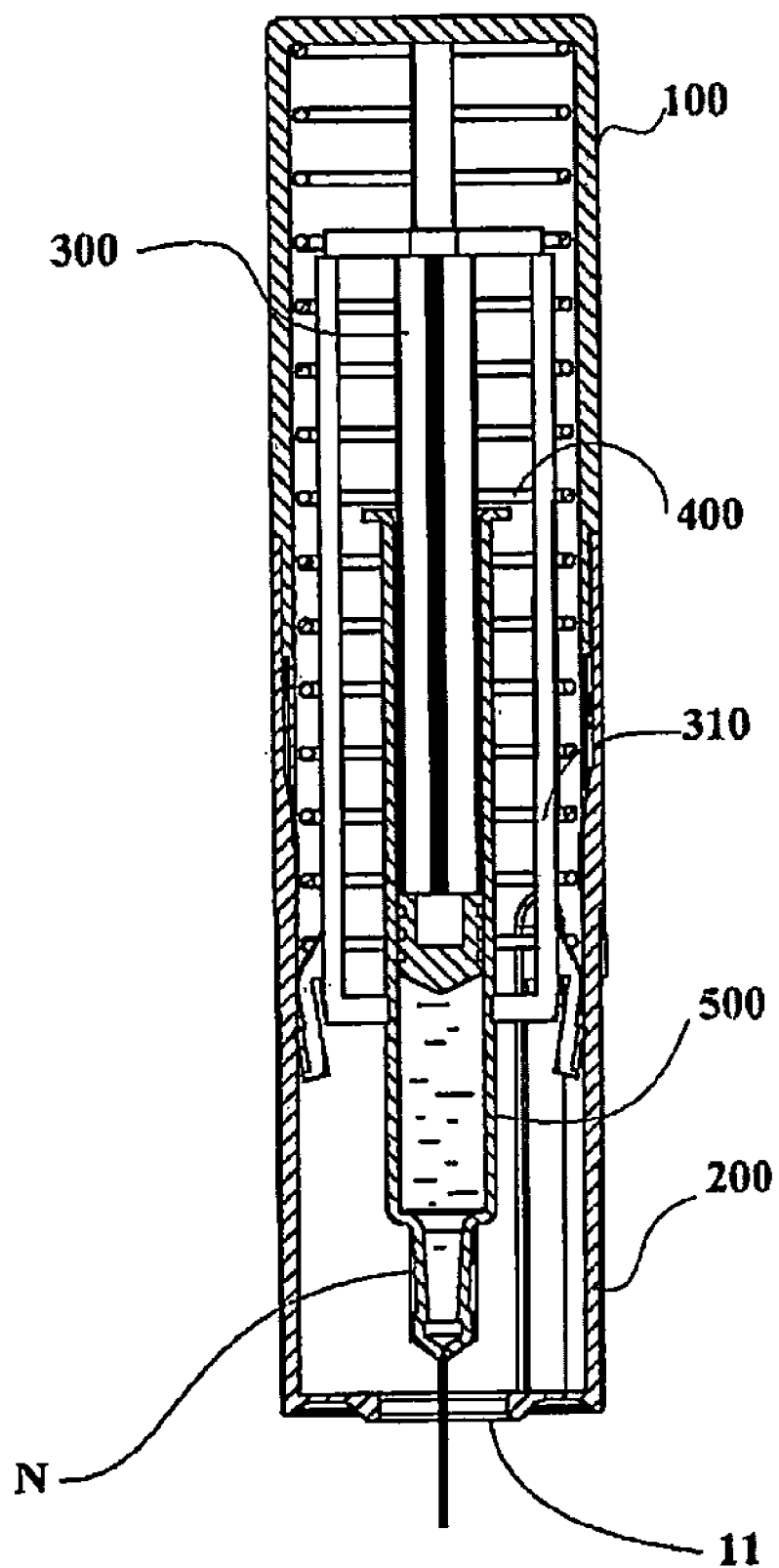
FIG. 22 is a view similar to that of FIG. 6, but showing the injector during the middle of drug delivery.
Figure 23:
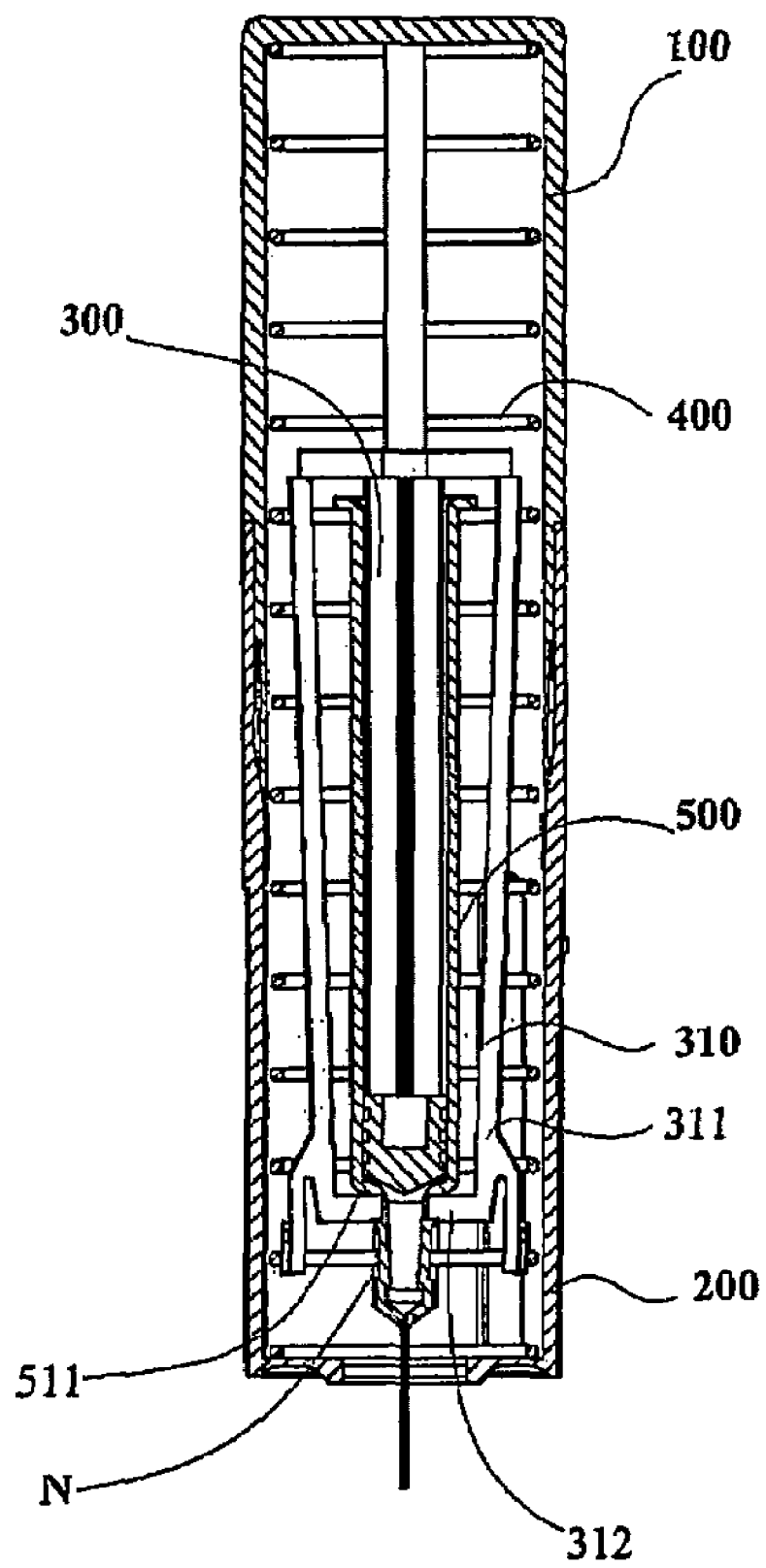
FIG. 23 is a view similar to FIG. 6, but showing the injector at the end of delivery.

The driver movement relative to housing is initiated. The drug delivery starts as illustrated in FIG. 12 and FIG. 13. At this stage the tangential force applied to latch fingers 314 is substantially reduced. The fingers 314 spread to an unloaded position while the bending of the fingers 314 toward the barrel 511 (FIG. 23) persists through delivery time The driver 300 is slidingly located within the housing. When the driver 300 is disengaged from the housing 100, the injector 10 is activated. The driver is biased by the spring 400. The spring 400 causes the driver to slide forward towards the distal end of the automatic injector 11 (FIG. 21). The driver 300 moves the stopper through the barrel 511 forcing the fluid in the barrel through the needle 512 to be delivered into an injection site. An intermediate position of the driver is illustrated in FIG. 22.

The driver 300 (see FIG. 14) of the exemplary embodiment of the invention with the shield sliding on the housing is comprised of a base 330, driver rod 320 and side fingers 310. The side fingers 310 have a core 311 attached to the base 330. On the opposite end fingers 311 have protrusions 312 abating the barrel and latches 313 engaged with the housing. The latches consist of two latch fingers 314 equipped with protruding sections 315. These sections 315 have an overhang section 316.

After the driver is disengaged from the housing the latch fingers are deflected radially as illustrated in FIG. 16. The latch finger 314 deflection allows the driver to slide in the housing.

The housing 100 (see FIG. 17 and FIG. 18) is a cylindrical part with two primary areas: a cylindrical section 101 and a second cylindrical section 102 with a reduced outside circumference matching the internal circumference of the shield 200. The housing 100 also has a base 103. The base 103 has two fingers 104 with latches 105 and 106. The latches 105 and 106 capture and hold the barrel of the cartridge after assembly.

The housing 100 has two symmetrical slits 120 with a long narrow section 121 and a wide opening 122. The wide opening 122 accepts the driver latch fingers 314 to engage the driver and the housing in the assembly. Overhang sections 316 in an unstressed state are wider than the opening 122 additionally securing the driver to the housing.

The housing contains two symmetrical openings 130 with built in leaf springs 131. These leaf springs are attached to the housing 100 at the base 132. The leaf springs serve to secure the shield in a shielded position after completion of delivery as is described below.

The automatic injector has an observation window 800 (see FIG. 9) and a reduced-length observation window 820 (see FIG. 12). This window is located in section 102 of the housing and is formed by the housing slots 113 jointly with the matching slots 225 in the shield 200. The observation window exposes the barrel to the user. The housing area 111 with an increased diameter extends onto and envelops the shield with its extensions 112 to provide an improved holding ability and support for the user during the operation of the injector.

The housing also has two flaftened areas 123. These areas accommodate protrusions on the inner shield surface.

The shield 200 (see FIG. 19 and FIG. 20) is a cylindrical part with a cylindrical section 201. Its internal circumference corresponds to the external circumference of the housing 100 in section 102. The shield 200 has two external flats 202. Furthermore, the shield has a base 204 with an opening 205 to accept the cartridge needle. The base 204 has two elevated ring-like features 206 and 207 to improve interface with the subcutaneous site.

The shield has furthermore two elevated areas 220 on the inner surface. These form outer fingers 221 engaging the overhang sections 316 of the latch fingers of the driver and during operation push the protruding latch fingers 314 together. The elevated section also forms the central finger 222 for disengaging the driver from the housing. Shield latches 223 prevent disassembly of the device and secondary exposure of the needle after shielding of the cartridge.

Figure 24:
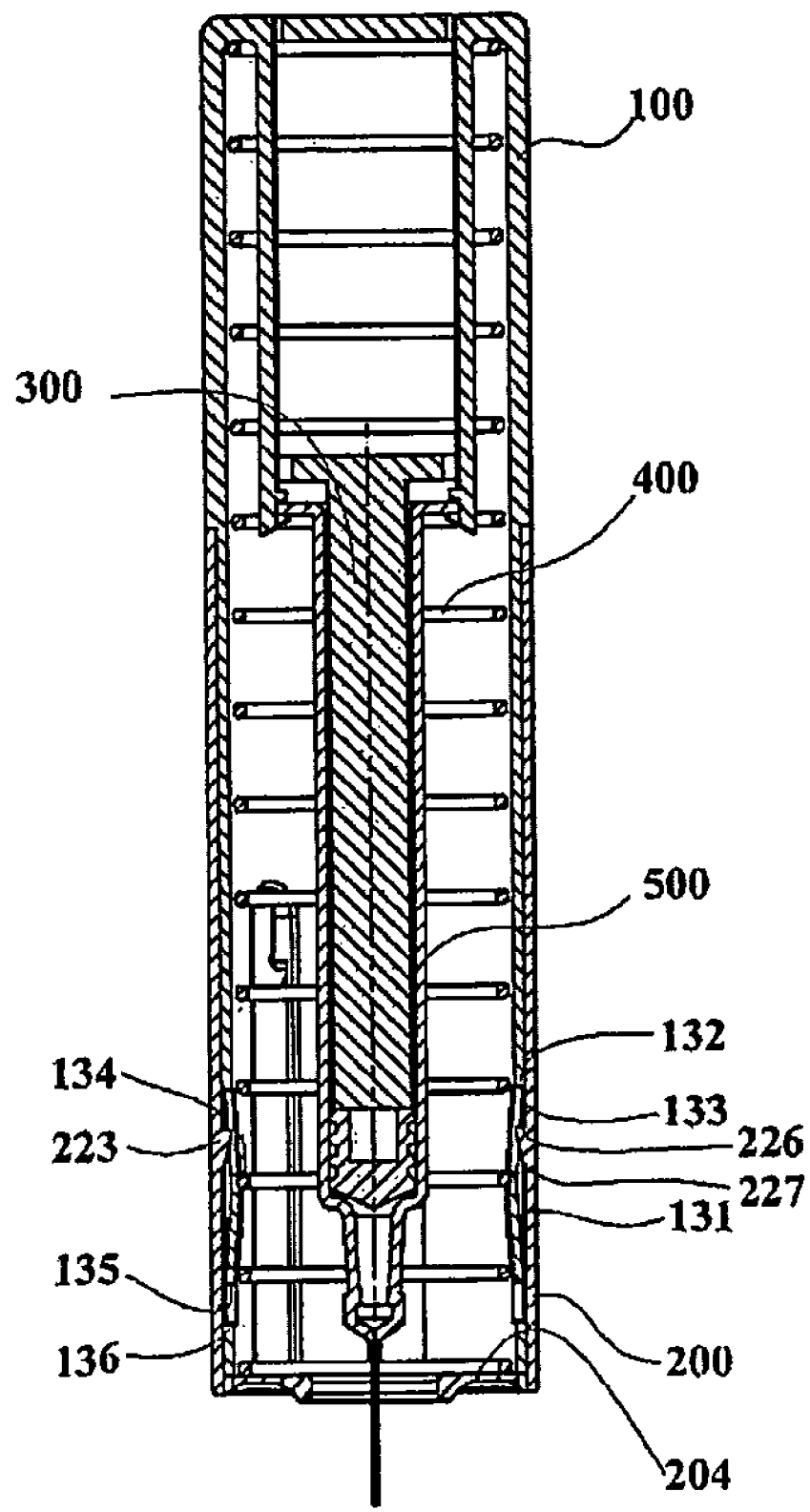
FIG. 24 is a view similar to FIG. 3, but showing the injector at the end of delivery.

Toward the end of injection, protrusions 312 of the driver fingers 311 slide off the barrel 511 allowing the fingers 311 to deflect toward the reduced-diameter neck N of the cartridge 500. This motion allows the spring 400 to slide over the latches 313 and engage the base of the shield 204 as illustrated in FIG. 24. Simultaneously the spring 400 deflects the leaf spring 131 as illustrated in FIG. 24. Thus, these protrusions 312 form a "change of barrel diameter" detector for the driver 300.

Figure 25:
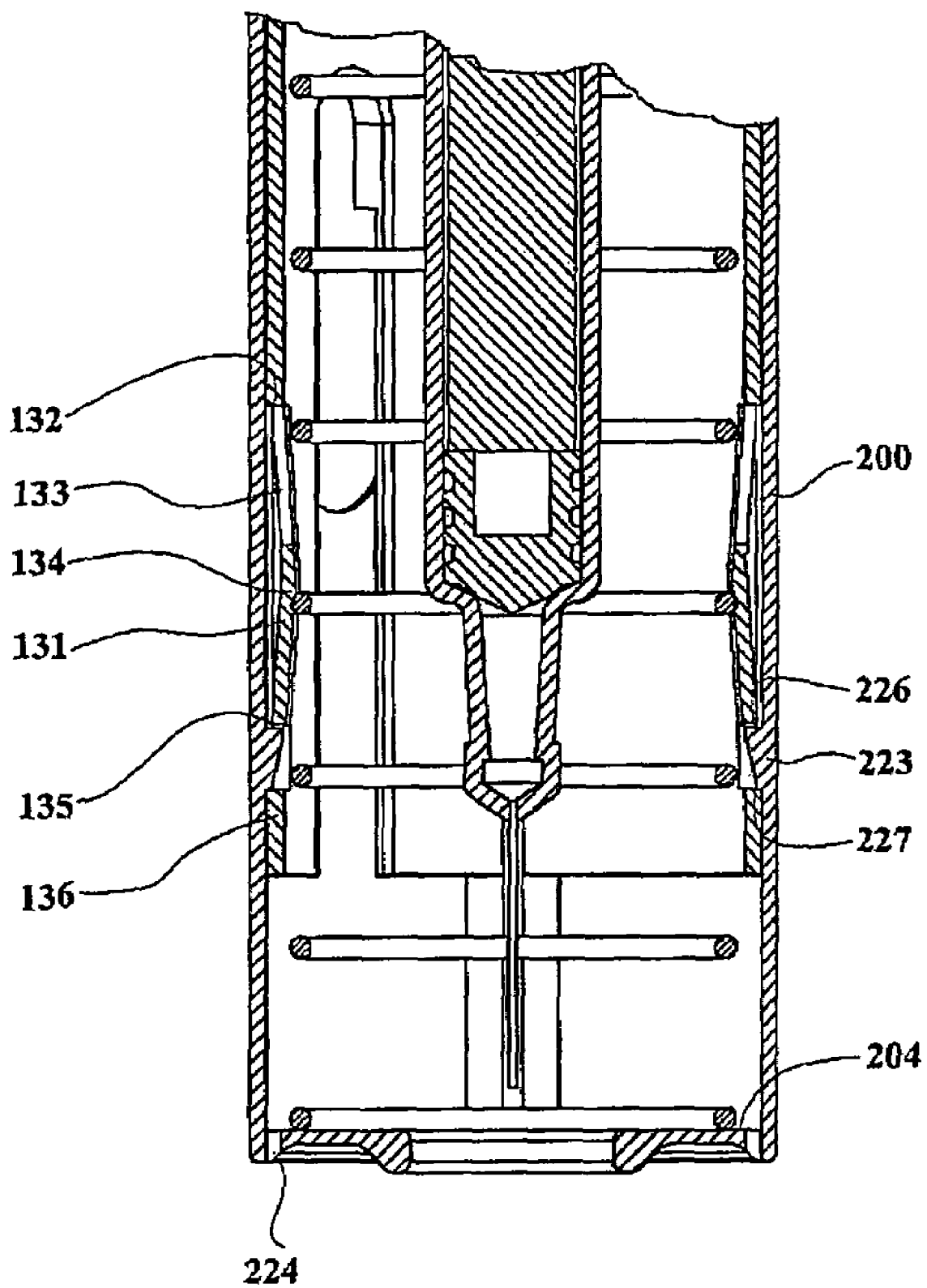
FIG. 25 is a partial sectional view of the injector illustrating the details of the shield locking mechanism of the automatic injector of the exemplary embodiment with the shield on the housing.
Figure 26:
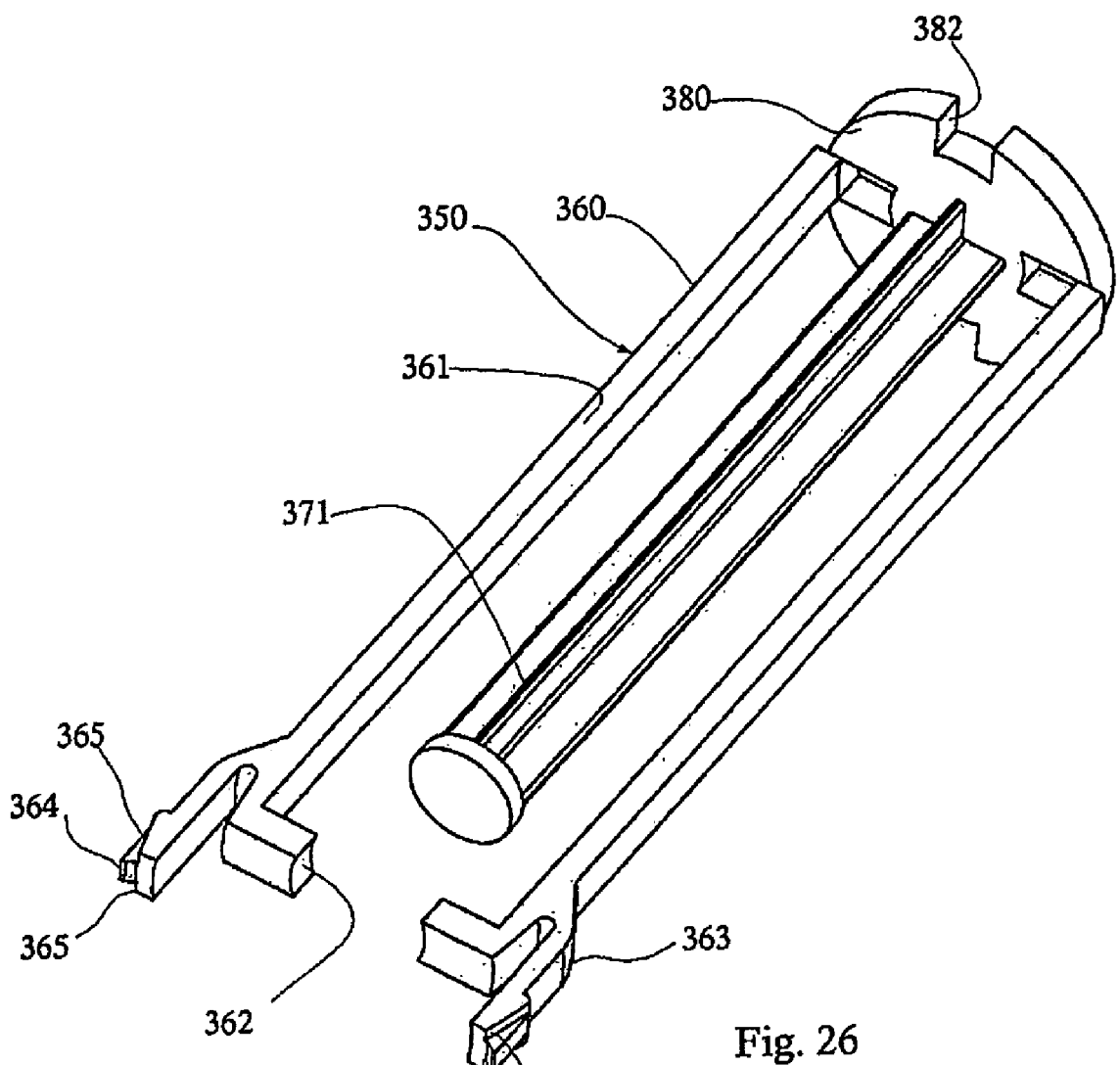
FIG. 26 is an isometric view of the driver, of the exemplary embodiment with the shield inside the housing, when engaged with the housing.
Figure 27:
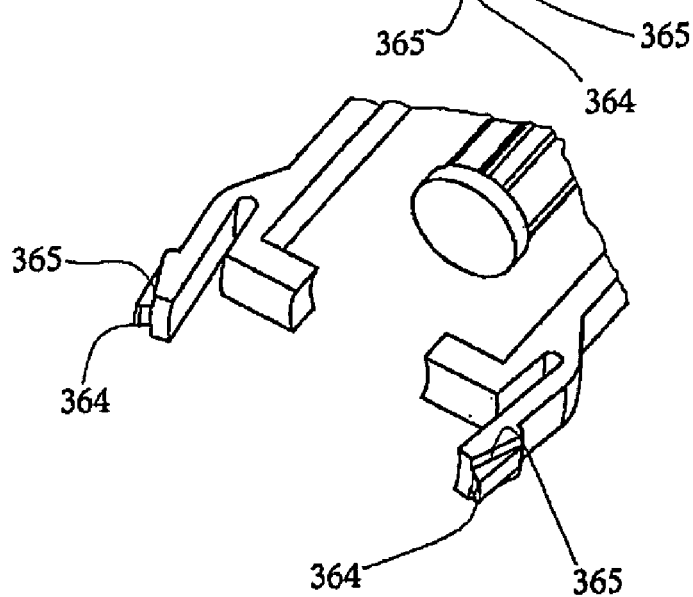
FIG. 27 is a partial isometric view of the driver of the exemplary embodiment with the shield inside the housing, with latches deformed during delivery.
Figure 28:
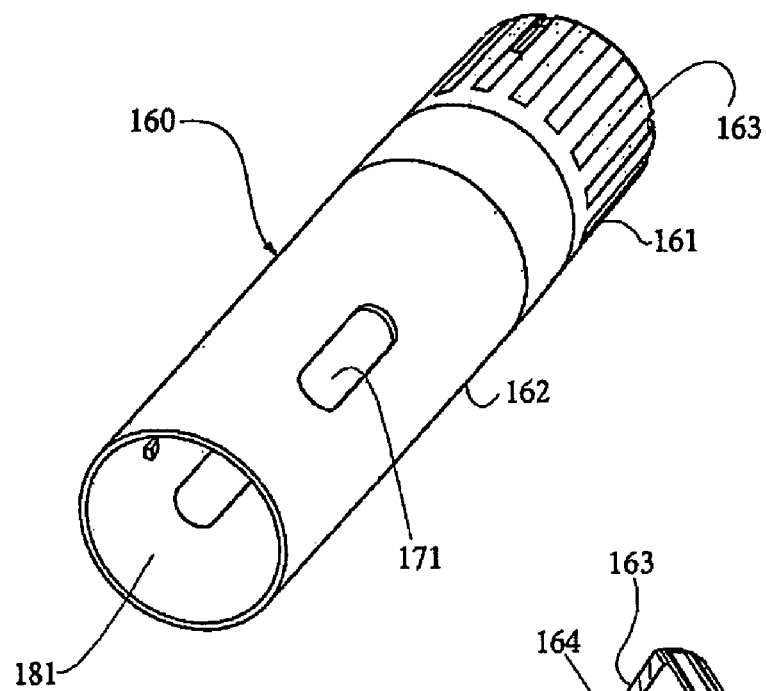
FIG. 28 is an external isometric view of the housing of the exemplary embodiment with shield inside the housing.
Figure 29:
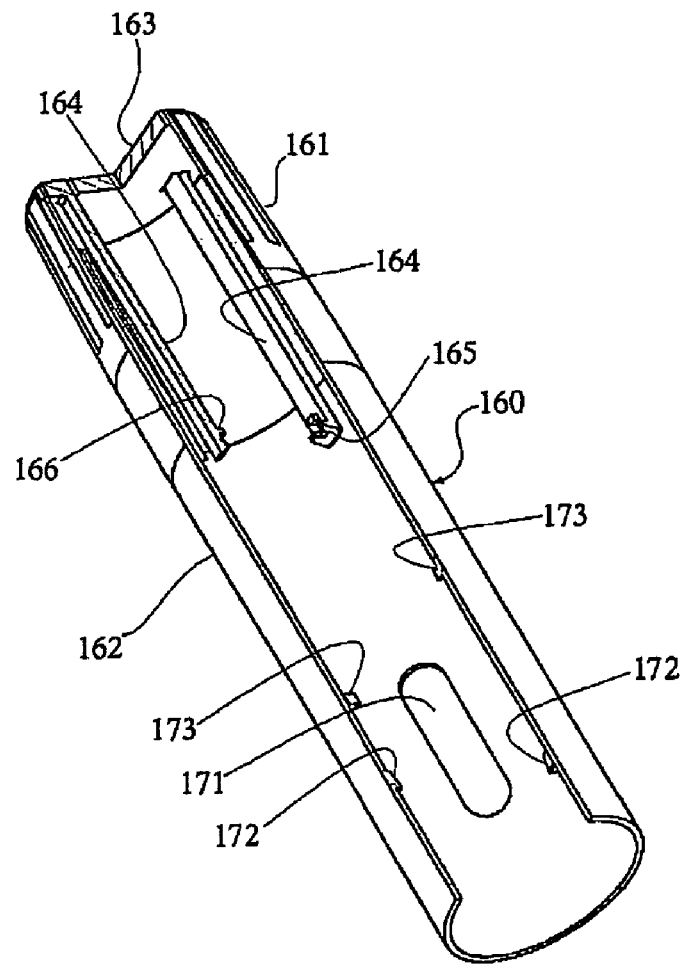
FIG. 29 is an isometric view of the housing with a removed section, of the exemplary embodiment with shield inside the housing.
Figure 30:
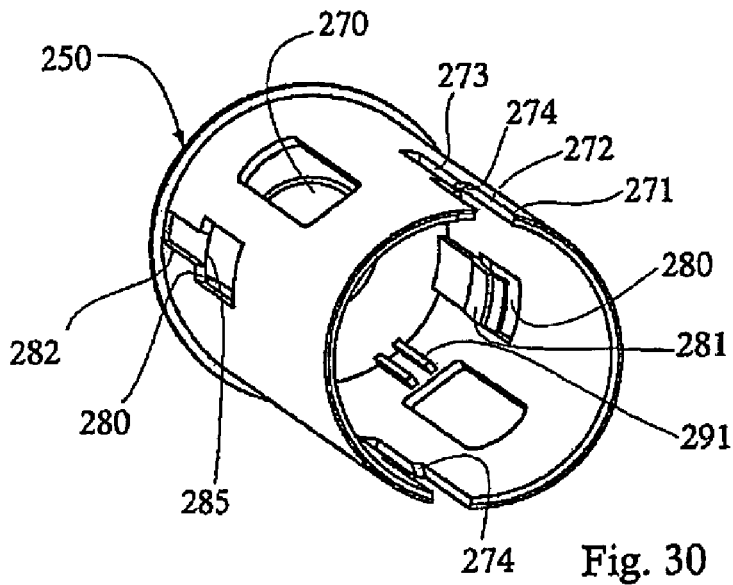
FIG. 30 is an isometric view of the shield from the proximal end, of the exemplary embodiment with shield inside the housing.
Figure 31:
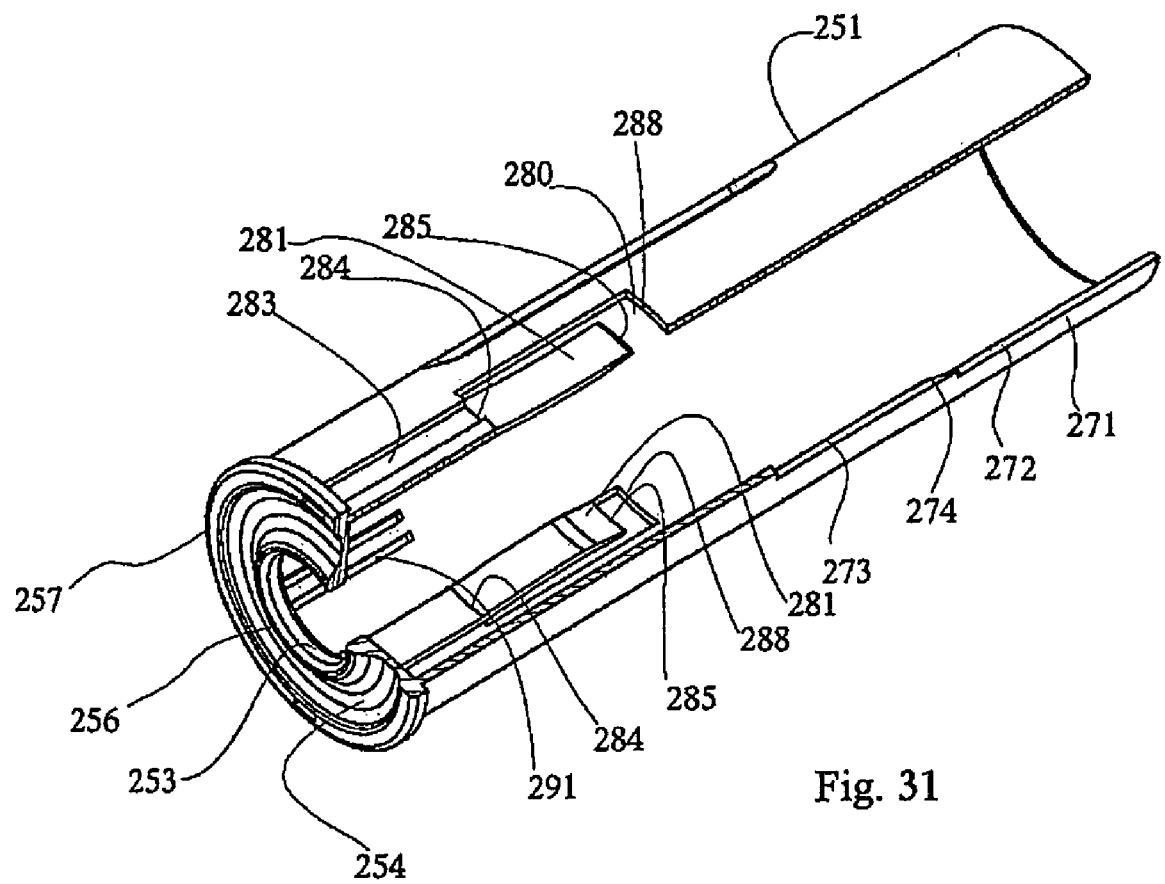
FIG. 31 is an isometric view of the shield from the distal end, of the exemplary embodiment with the shield inside the housing, with a cylindrical section partially removed.

The spring acting on the base of the shield 204 provides a substantial force resulting in an extraction of the cartridge needle from the subcutaneous tissue and the return of the shield to its extended position as illustrated in FIG. 25. Furthermore, the spring impacting the base of the shield provides a clear tactile and audible indication of the end of drug delivery.

The spring 400 forces the leaf springs 131 attached to the housing 100 outward. The latch of the shield 223 interacts with the leaf spring 131, thereby preventing a repeated displacement of the shield 200. The shield 200 of the automatic injector is further prevented from moving off the housing 100 by a ring like feature 136. The automatic injector now has a shielded needle and is ready for disposal.

Another exemplary embodiment with the shield inside the housing is further described in FIG. 26 through FIG. 36. The driver 350 (see FIG. 26) of the exemplary embodiment of the invention with the shield sliding inside the housing is comprised of a base 380, driver rod 371 and side fingers 360. The side fingers 360 have a core 361 attached to the base 380. On the opposite end, fingers 361 have protrusions 362 abutting the barrel 511 and latches 363 engaged with the housing. The latches consist of two latch regions 365 of lower height and an elevated section 364.

The housing/driver disengagement mechanism is different in this exemplary embodiment. The latch 363 deflects only in the radial plane being forced inward by the shield 250 wedged between the housing and the driver as will be described below.

The housing 160 (see FIG. 28 and FIG. 29) is a cylindrical part with two primary areas: a knurled section 161 and a cylindrical section 162. The internal circumference 181 is matched to the external circumference of the shield 250. The housing 160 also has a base 163. The base 163 has two fingers 164 with latches 165 and 166. The latches 165 and 166 capture and hold the barrel of the cartridge after assembly.

The housing 160 has a pair of symmetrical latches 172. These latches interact with the shield after use to lock it in a shielded position. Housing latches 172 prevent disassembly of the device and secondary exposure of the needle after delivery. The other pair of latches 173 releasably attaches the driver 350 to the housing 160.

The housing 160 further has a pair of symmetrical openings 171. These openings together with openings in the shield 250 form observation windows.

The shield 250 (see FIG. 30 and FIG. 31) is a cylindrical part with a cylindrical section 251. Its external circumference matches the internal circumference of the housing 160 in section 162. The shield contains two symmetrical openings 280 with built-in leaf springs 281. These leaf springs are attached to the shield 250 at the base 282. The leaf springs serve to secure the shield in a shielded position after completion of delivery as is discussed below. Furthermore, the shield has a base 254 with an opening 253 to accept the cartridge needle. The base 254 has two elevated ring-like sections 256 and 257 to improve interface with the subcutaneous site.

The shield has furthermore two elongated openings 270. These form an observation window in conjunction with the housing openings 171. The shield furthermore has ribs 291. These ribs support the spring 450.

The shield 250 has symmetrical slits 271. These slits have a wide section 272 followed by a narrower section 273. The front of the narrower section is tapered 274. This taper 274 of the shield disengages the driver from the housing during activation, as illustrated in FIG. 32 through FIG. 35.

Figure 32:
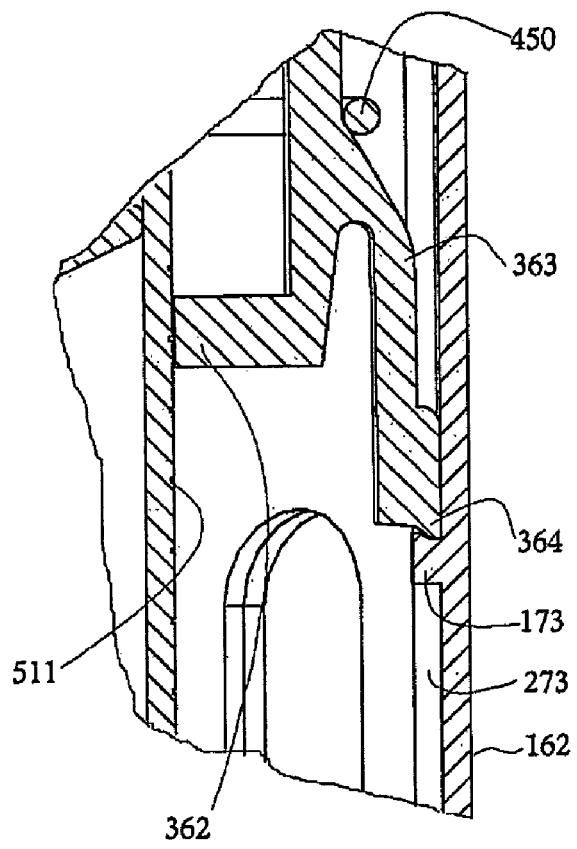
FIG. 32 is a partial sectional view of the injector, shield inside the housing, showing the injector in a state wherein the shield is slightly depressed and the section shown through the middle of the latch.
Figure 33:
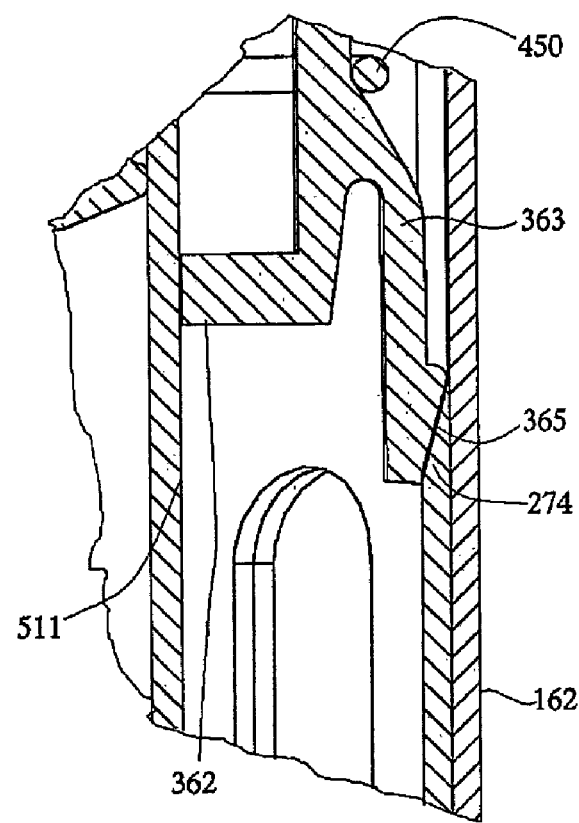
FIG. 33 is a partial sectional view of the injector as illustrated in FIG. 32, but showing the injector section through a side of the driver latch.
Figure 34:
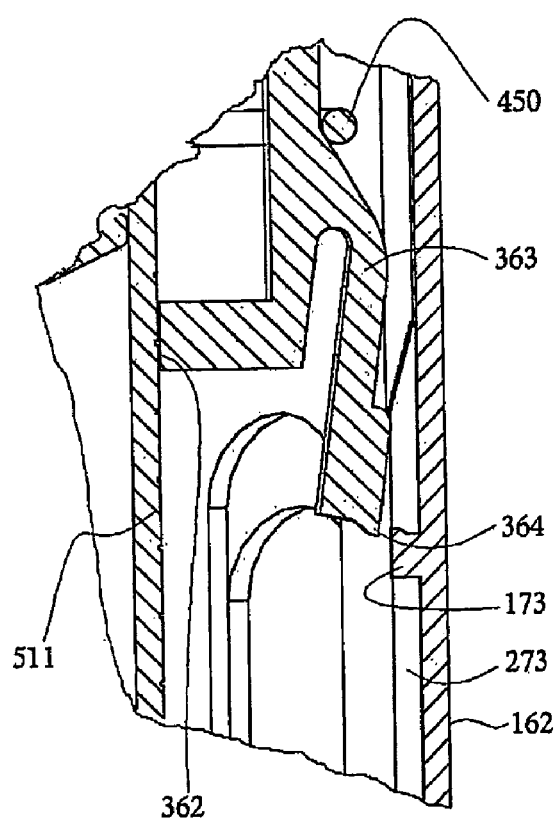
FIG. 34 is a partial sectional view of the injector as illustrated in FIG. 32 but showing the injector in a state wherein the shield is further depressed and the driver is disengaged from the housing.
Figure 35:
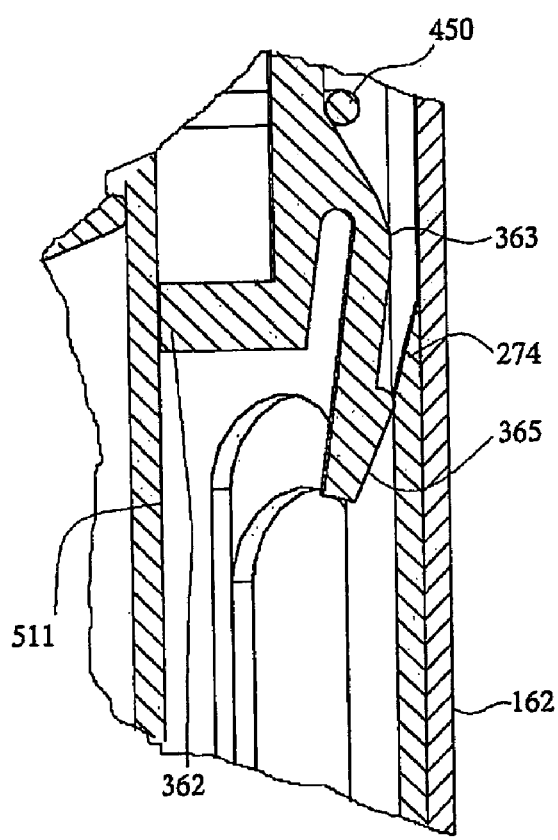
FIG. 35 is a partial sectional view of the injector illustrated in FIG. 33 but showing the injector in a state wherein the shield is further depressed and the driver is disengaged from the housing.

The beginning of the driver 350 and housing 250 disengagement process is illustrated in FIG. 32 and FIG. 33. The driver latch 363 extensions 364 are engaged to the housing pins 173. The shield disengagement taper 274 is pushed between the latch 365 and the housing 160. Eventually, the driver latch 364 is deflected and disengaged from the housing as illustrated in FIG. 34 and FIG. 35.

Figure 36:
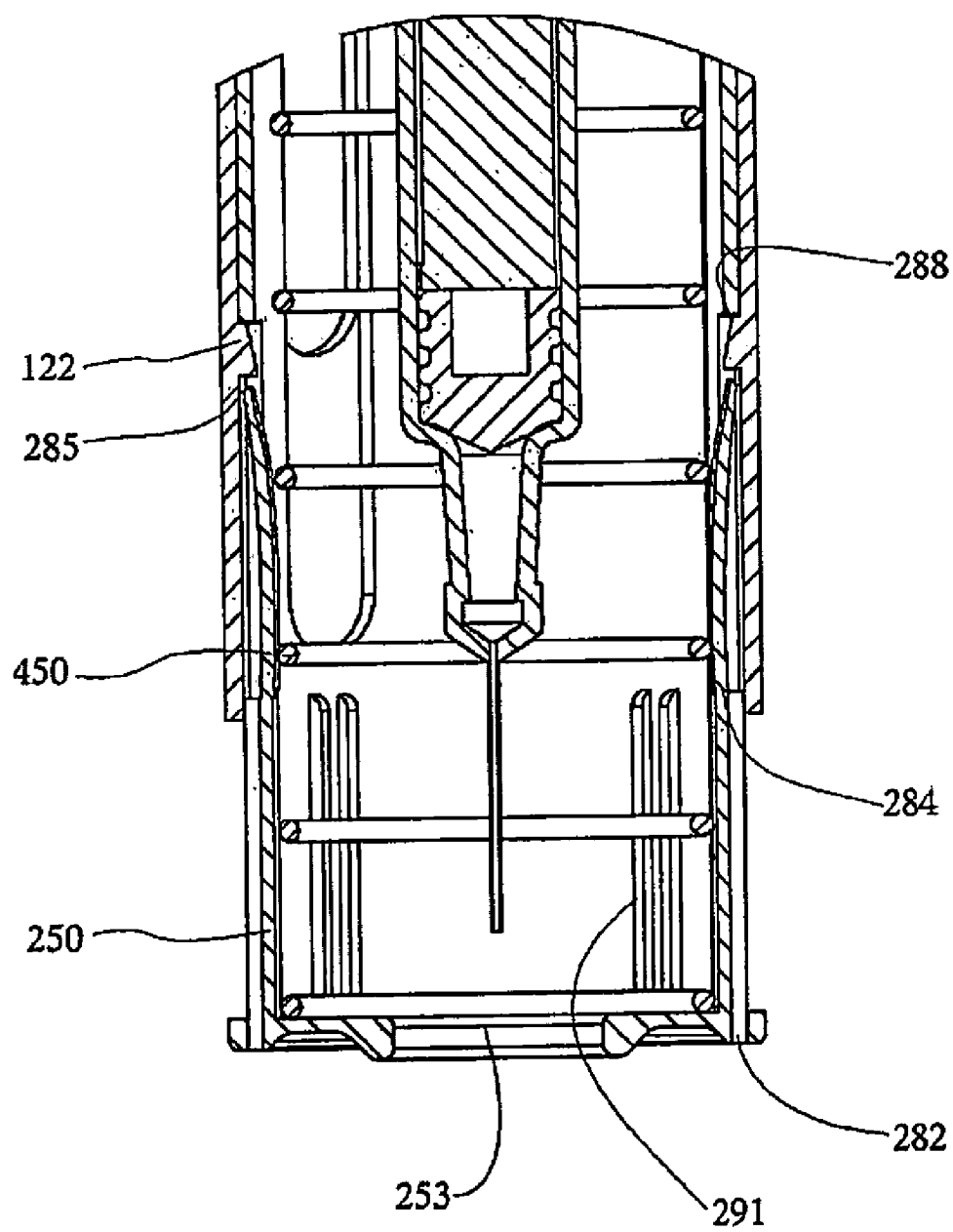
FIG. 36 is a partial sectional view of the injector illustrating the details of the shield locking mechanism of the shielded automatic injector of the exemplary embodiment with the shield inside the housing.

The operation of the automated shielding process of the embodiment with the shield inside the housing is similar to that of the shield on the housing. The spring 450 acting on the base of the shield 254 provides a substantial force resulting in an extraction of the cartridge needle from the subcutaneous tissue and the return of the shield to its extended position as illustrated in FIG. 36.

Figure 37:
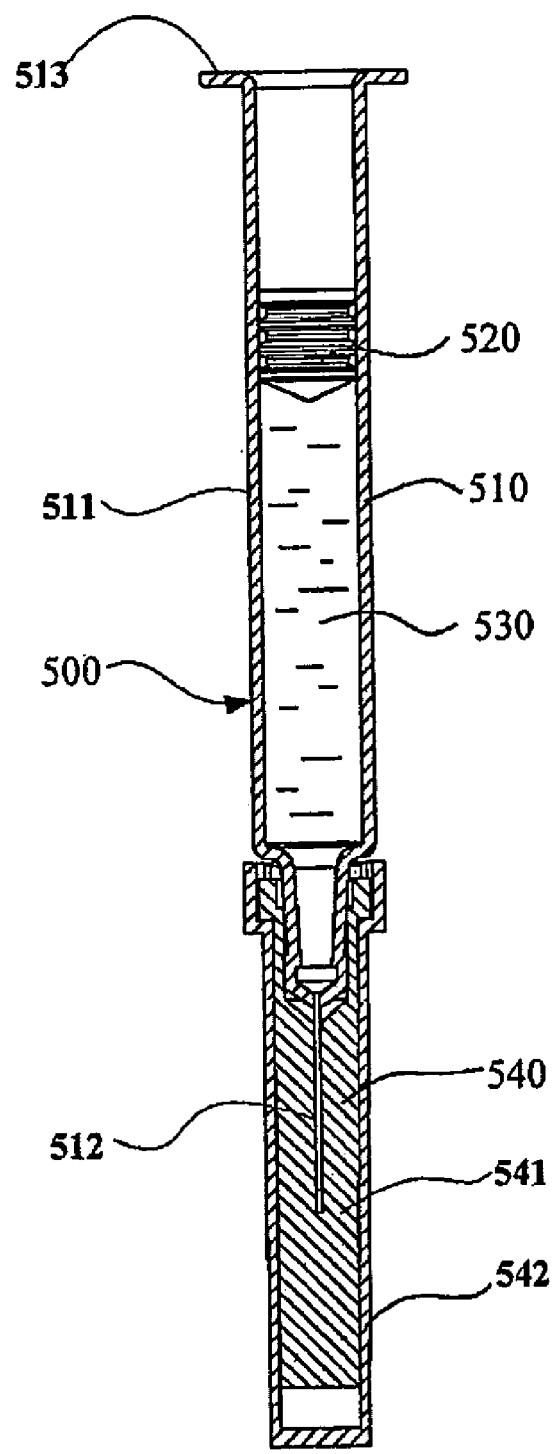
FIG. 37 is illustrating an exemplary embodiment of the filled cartridge of the present invention.
Figure 38:
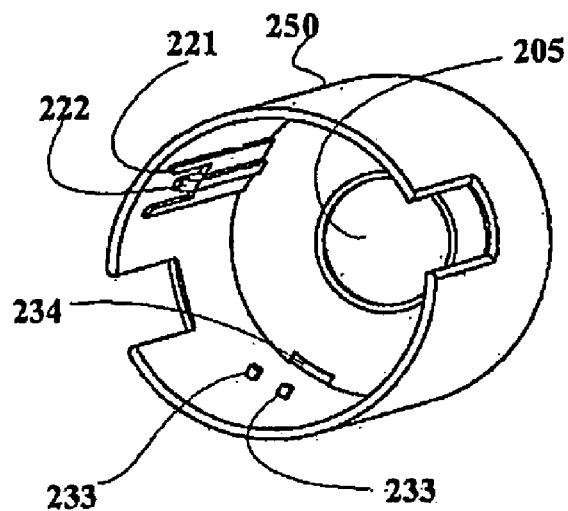
FIG. 38 is an isometric view of the shield from the proximal end illustrating an alternative embodiment of the mechanism for generating the force profile defined in FIG. 7 and FIG. 8.
Figure 39:
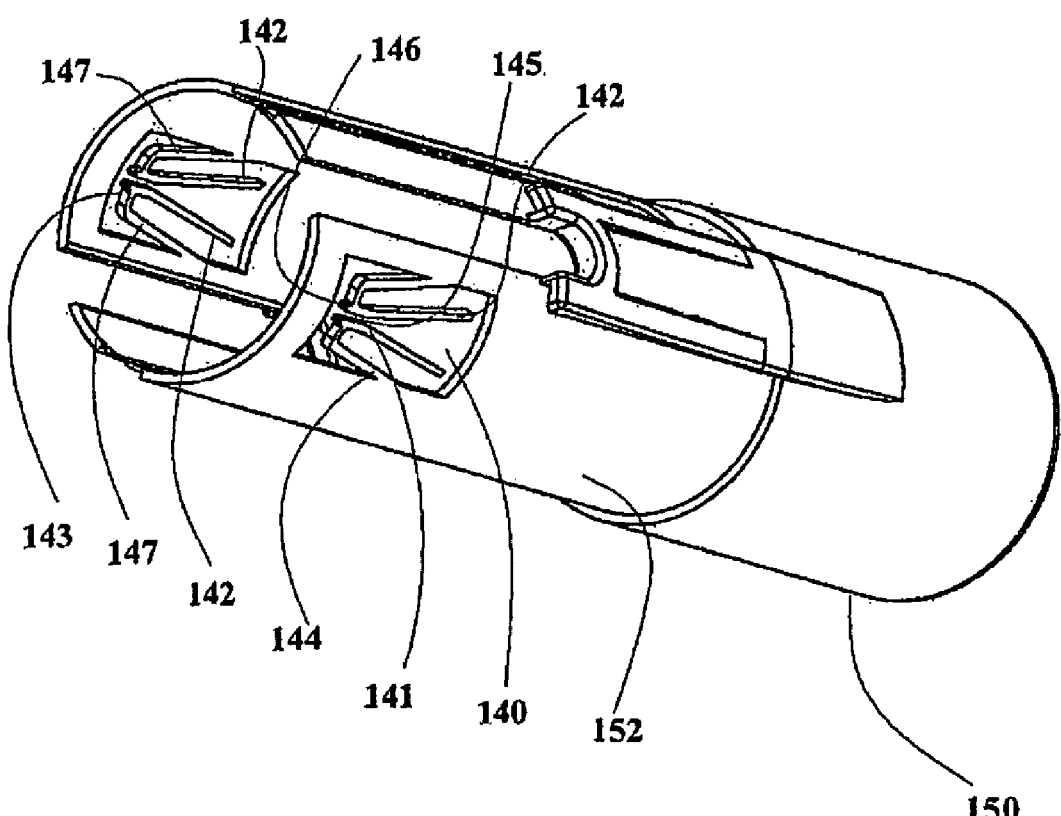
FIG. 39 is an isometric view of the housing illustrating an alternative embodiment of the mechanism for generating the force profile defined in FIG. 7 and FIG. 8 with the shield inside the housing.

The typical Hypak cartridge 500 is illustrated in FIG. 37. It has a barrel 510 consisting of a glass barrel 511 with a staked needle 512. The glass barrel 511 has flanges 513. The barrel is filled with drug 530. The drug is sealed by a stopper 520 which is in a sliding relationship with the barrel. The needle is shielded by a protective cap 540 made from an elastomeric component 541 abutting the needle. The needle protective coyer 540 frequently has a rigid plastic protective cup 542 simplifying the cap removal.

Device with Titration:

The titration is made feasible by the observation window. Only when the cartridge is observed can the user titrate the content of the cartridge and expel the air. Three examples for implementing the titration are detailed in FIG. 41, FIG. 42 and FIG. 43.

Figure 41:
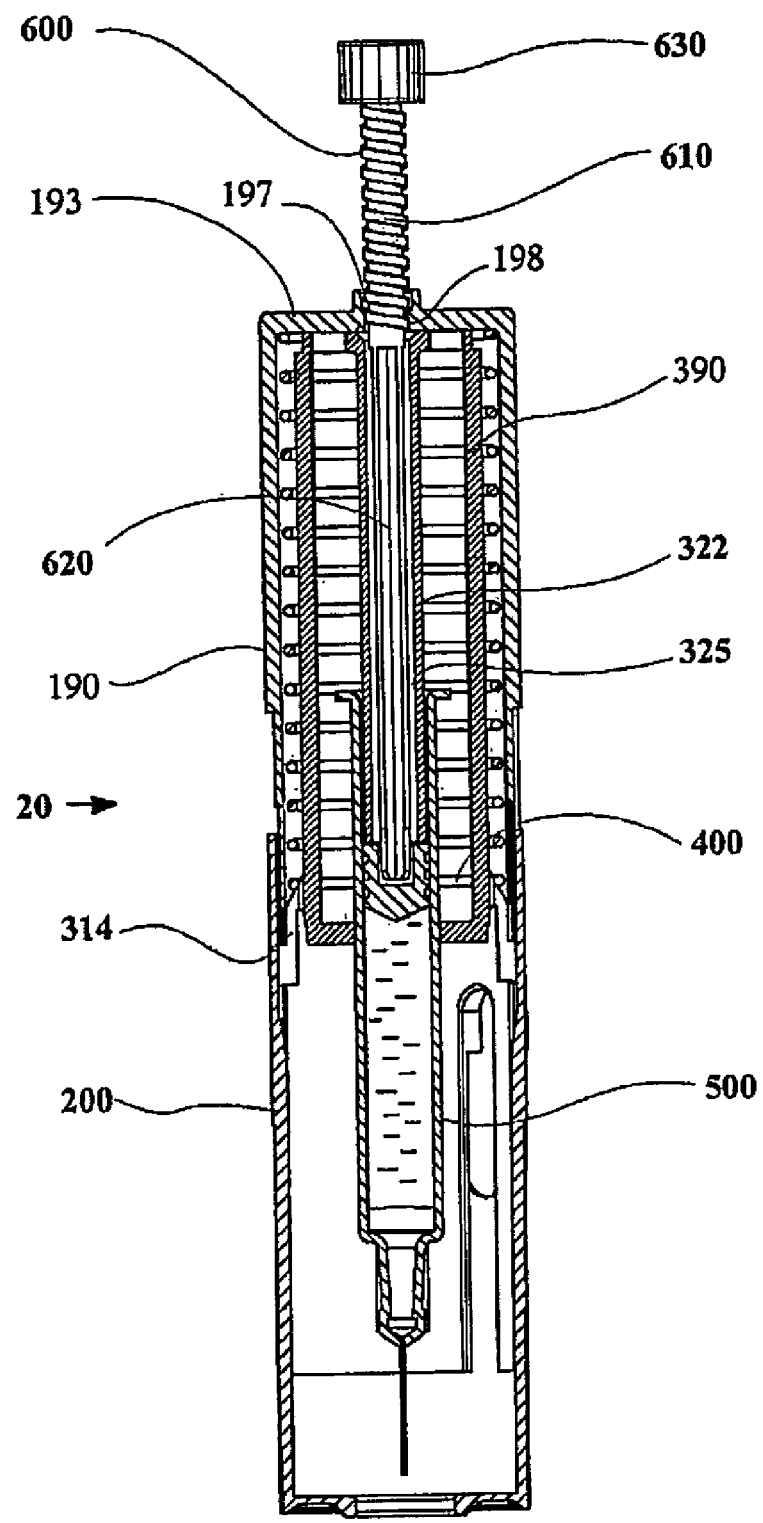
FIG. 41 is a view similar to that of FIG. 6, of an exemplary embodiment of the invention and the shield sliding on the housing but showing the titration mechanism employing a threaded rod.

The injector 20 of the exemplary embodiment of the invention with the shield sliding on the housing includes a rod 600 protruding through the opening 197 in the base of the housing at the proximal end of the injector as illustrated in FIG. 41. The driver 325 has an internal rod passageway 322 to accommodate titration rod 600. The titration rod has a threaded section 610 engaged with the threaded section of housing 198 of the opening in the housing 197. Rod also has an unthreaded section 620 abutting the stopper 520 and a knurled knob 630 for hand operation.

Figure 42:
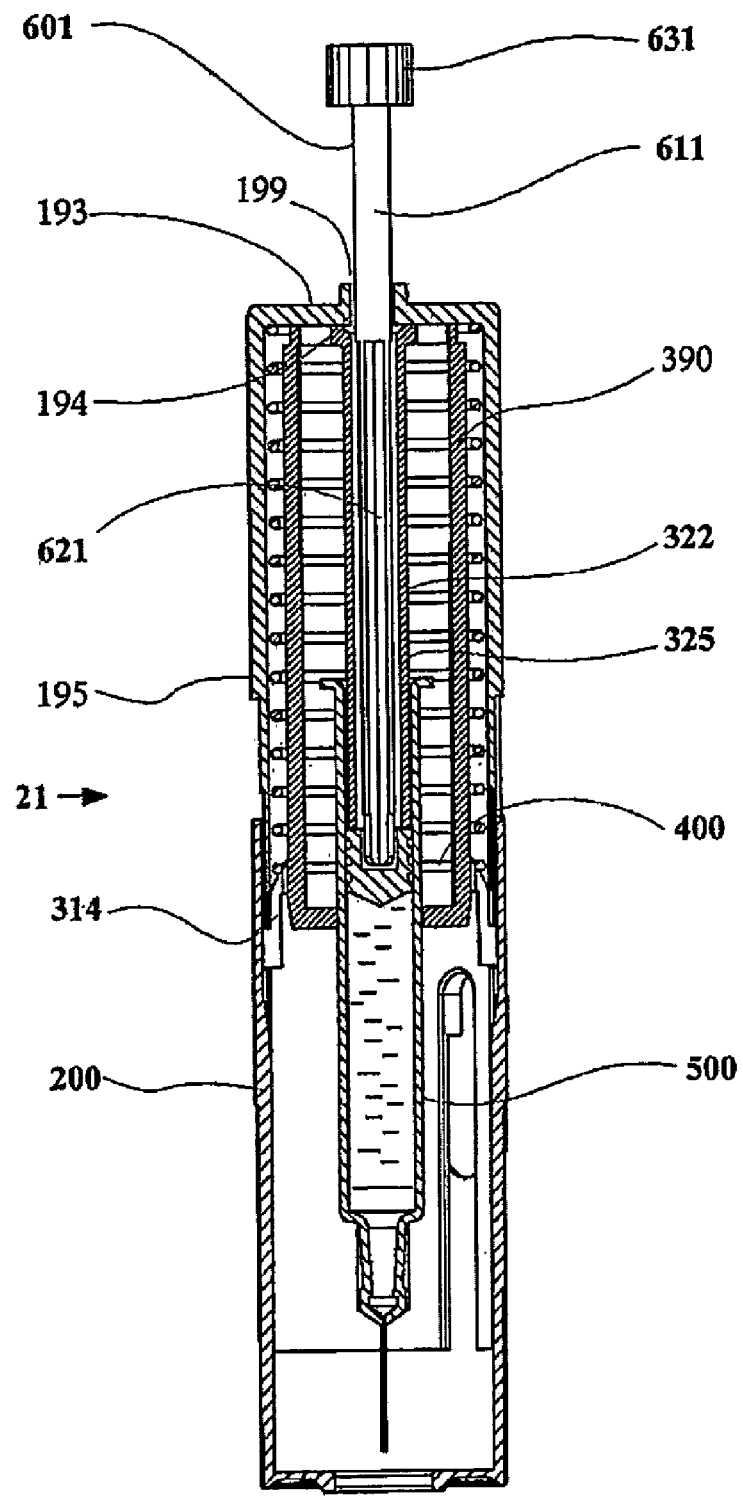
FIG. 42 is a view of an alternative titration mechanism of an exemplary embodiment of the invention and the shield sliding on the housing employing a smooth rod.

Alternative to the threaded titration rod is a rod without a thread in FIG. 42. The rod 601 extends through an opening 199 of a rear wall 193 at the proximal end of the injector 21. The rod 601 has an unthreaded section 621 abutting the stopper 520 for pushing it during titration.

Figure 43:
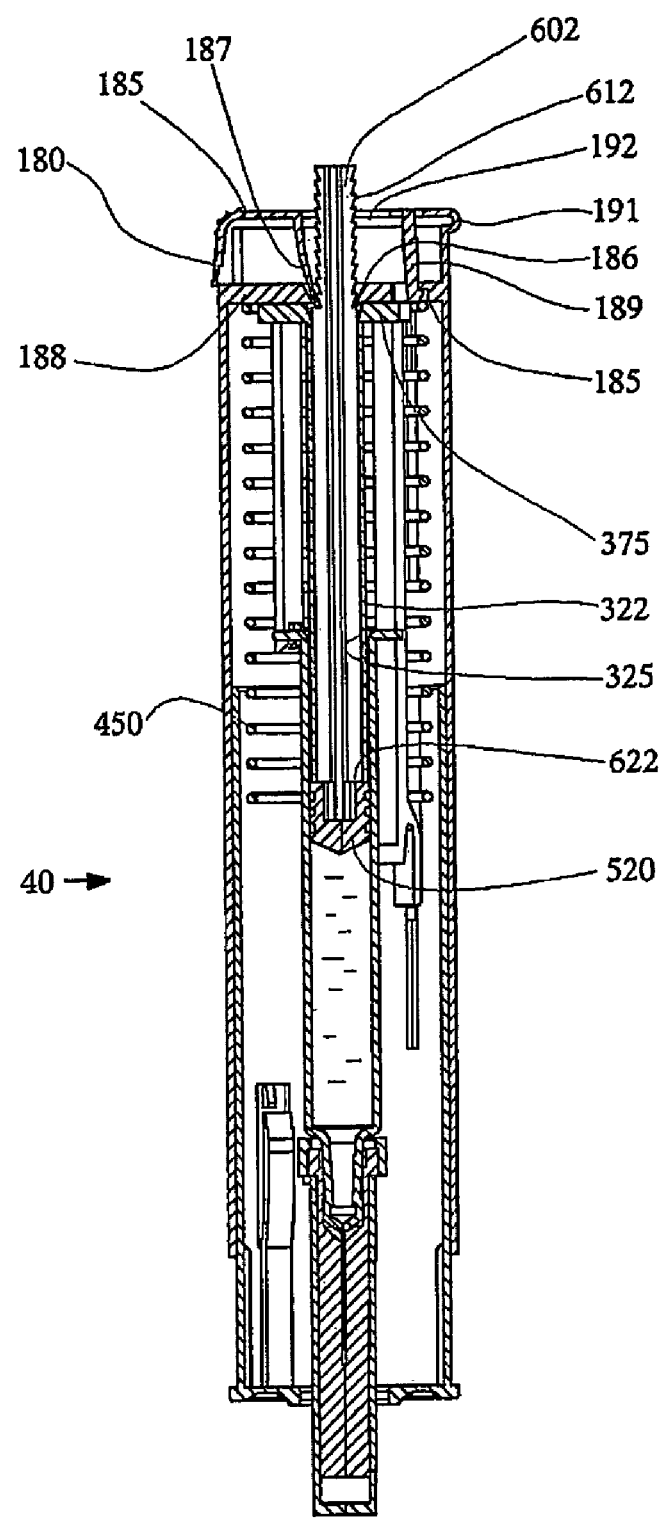
FIG. 43 is a view of an alternative titration mechanism of an exemplary embodiment of the invention with the shield sliding inside the housing but showing the titration employing a ratchet mechanism.

Another alternative is a titration rod with a ratcheted surface. The injector 40 of the exemplary embodiment of the invention with the shield sliding on the housing includes a rod 602 protruding through the opening 192 in the base of the housing at the proximal end of the injector as illustrated in FIG. 43. The driver 375 has a rod 322 hollow internally 325 to accommodate titration rod 602. The titration rod has a toothed section 612 engaged with the ratchet 187 and no-back latch 186 of the housing 185. Rod 602 also has a section without ratchets 622 acting on the stopper 520. The ratcheting mechanism is formed as part of the housing 185. It is fixed at the hinge 191 with the tooth 189 engaging the housing. The travel of the ratchet 187 is limited by a limiter 180. The titration mechanism with a ratchet allows for an incremental propulsion of the rod toward the stopper.

Use of the Device:

As shown in FIG. 6 of the preferred embodiment, the first step in the use of the injector 10 is to remove the safety cap 540. Then the automatic injector 10 is applied to the injection site and depressed by pushing on the housing 100. This action results in the exposure and insertion of the needle 512. It also releases the driver 300 automatically initiating the injection.

During the injection time, the holding force is minimal as illustrated by element 736 in FIG. 8. Upon completion of the injection the spring 400 moves toward the shield 200. The force acting on the shield increases to the level of the spring force as illustrated by 721 and 737, respectively, in FIG. 7 and FIG. 8. This force leads to the extraction of the needle from the tissue and shielding of the needle by the shield 200. The spring force somewhat decays through the motion (see displacement 722 and force 738). At the end of the shielding, the shield is locked. The injector is ready for disposal.

Without being limited to a particular theory, as an example of the balances of forces working in the injector, it generally takes about 1.0 kgf (10 Newtons) to displace the shield 200 by about 5 mm. The initial injection force of the driving unit 400 is, for example, about 1.5 kgf (15 Newtons), and the final pushing force during shielding is about 1 kgf. Dynamic friction takes, for example, 0.2 kgf (2 Newtons), at maximum.

The leaf spring 131 does not affect the operation of the injector 10 before or during delivery. However, during retraction, the spring 400 bypasses the leaf spring 131 and deflects it. The shield 200 is locked between the leaf spring 131 and the latch 223 preventing potential axial movement of the shield and consequential re-exposure of the needle 512. In other words, the shield 200 is locked to the housing 100 and unable to move.

Use of the Device with Titration:

The first step in using this injector 20 (or 21 or 40) is to remove the safety cap 542 out of the opening 205 at the distal end of the injector. Then any residual air in the cartridge 500 could be purged and the amount of liquid in the syringe can be adjusted to the required dosage by titration. The titration is achieved by positioning the injector 10 vertically so that the needle 512 is upright and by moving the titration rod 600 (or 601 or 602) toward the stopper and thus, moving the unwanted air and drug out of the injector through the needle.

Titration solves the problem of removing residual air commonly included in pre-filled syringes, which is a by-product of the filling technology. Titration also releases potential high static friction between the stopper 520 and the barrel 511 caused by non-movement over a long period of time (e.g., storage).

In order to minimize the amount of drug collected inside the injector during titration, the injector could be turned needle down after the residual air is purged as observed through the window.

The housing 100 and the shield 200 of the exemplary embodiment of the invention with the shield sliding on the housing preferably include a window that allows a user to view the contents and amount of dosage in the cartridge 500 before, during and after delivery. This window is also essential for the titration. FIGS. 9 and 12 are isometric views of the injector 10. FIG. 9 corresponds to the injector 10 at the stages before the injection and during titration. It is important to have a full window to observe the barrel contents during preparation to injection. FIG. 12 shows the injector 10 during injection when the size of the observation window is substantially reduced. At this stage the drug is not observed. After delivery, the observation window 800 of the injector 10 is again at the original length with the empty cartridge and spring being visible through the window for inspection.

In summary, a user looking through the window 800 of injector 10 can observe the amount of dosage in the cartridge

500. During storage, the cartridge 500 is filled with the drug solution. During titration, extra solution and air bubbles are pushed out of the barrel 500.

The injector 30 of the exemplary embodiment of the invention with the shield sliding inside the housing has a full size observation window also during injection as illustrated in FIG. 4. The opening 171 in the housing 160 is matched to the length of the active cartridge area. The opening 270 in the shield 250 is substantially longer providing for a consistent cartridge visualization before, during and after injection.

The injectors constructed in accordance with the exemplary embodiments provide a safe and efficient approach to delivering a drug into a patient. The injector would be used as a disposable device and can incorporate various combinations of the features described herein.

Figures 40A, 40B, 40C:
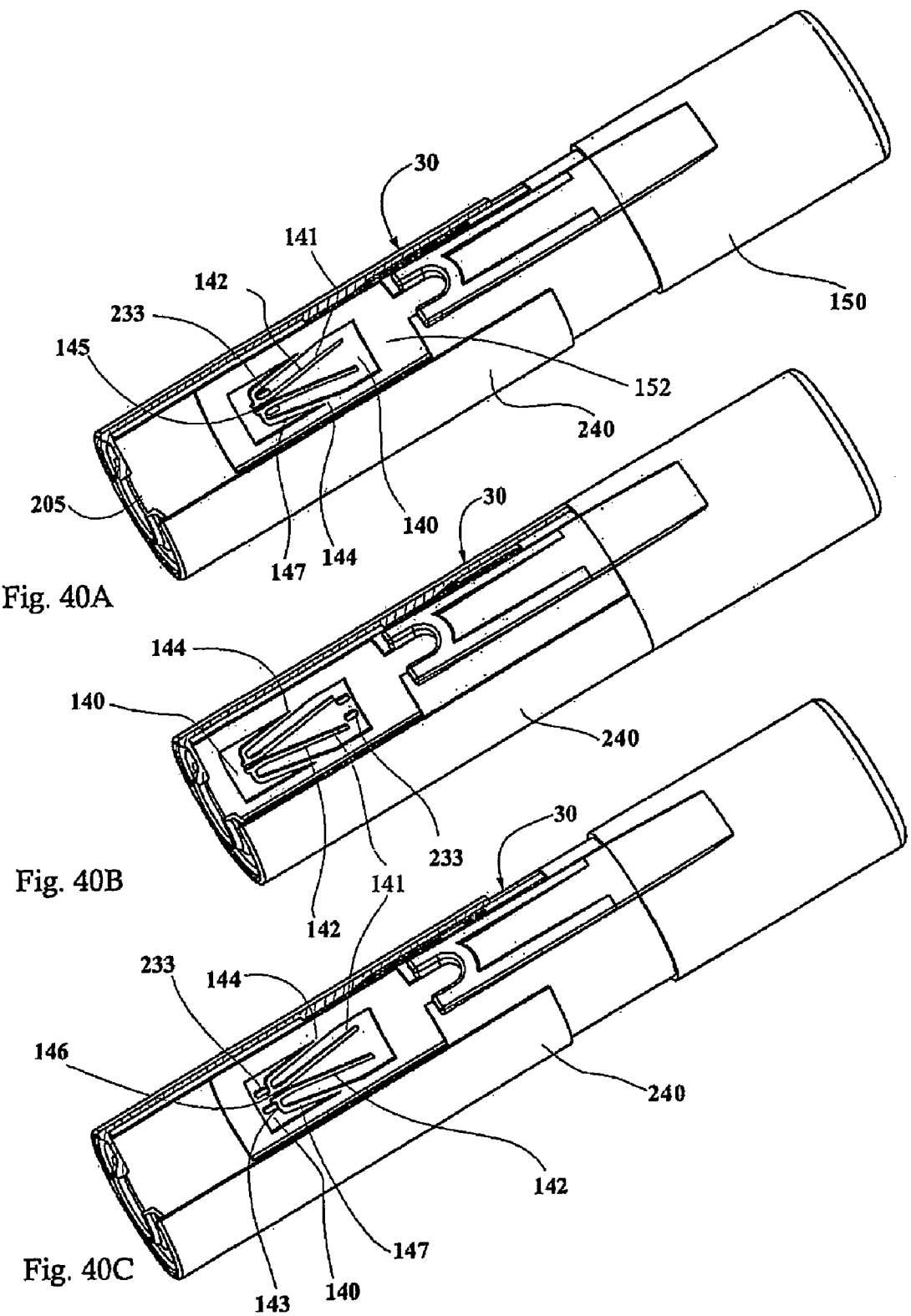
FIG. 40A illustrates the arrangement prior to use.
FIG. 40B illustrates the automatic injector with a deployed shield.
FIG. 40C illustrates shielded discard position.

Alternative Embodiments:

An alternative embodiment of the present invention could have a different latching mechanism as illustrated in FIG. 40A, FIG. 40B and FIG. 40C of the exemplary embodiment of the invention with the shield sliding on the housing. The cutouts of the housing form a pattern providing locking of the shield for disposal and preventing second shield displacement.

The shield 240 has two pins 233 interacting with a slotted housing 150. The housing cutouts are illustrated in FIG. 40A and are defined by numerals 140 through 147. Housing 150 contains two cutouts 140. Cutout 140 creates a shaped latch 141. Latch 141 is attached to housing section 152 at base 144. Latch 141 is formed from two sections 142 and 147 connected by 143. The latches 141 are separated by a gap 145.

FIG. 40A illustrates the operation of this alternative latching mechanism. Only housing 150 and shield 240 are shown for clarity. Furthermore a section of the shield 240 and housing 150 are removed. FIG. 40A illustrates assembly before displacement. FIG. 40B illustrates a displaced shield. FIG. 40C illustrates a discard position. Pressing the shield 240 against injection site causes bending of latches 142 and closing of the air gap 145. At the end of shield 240, displacement latch 142 is released and returns to its original shape as illustrated in FIG. 40B. Once delivery is completed, action of spring 400 forces shield 240 to retract. Pins 233 move into the gap between latches 142 and expand the air gap 145 by a bending latch elements 142 and 147. The pins 233 reach their final position as shown in FIG. 40C. These pins 233 prevent re-exposure of the needle. Protrusion 146 of latches 121 further increase the holding force provided by the housing 150 and shield 240.

In summary, prior to the shield 240 displacement, the pins 233 are located inside the hooks 142 formed by the cutouts in the housing (see FIG. 40A). During shield 240 displacement the hooks deflect and allow the pins 233 to move axially inside the housing cutouts 140 to a position illustrated in FIG. 40B. During the return of the shield 240 the pins 233 deflect the hooks 142 and end up at the base of the hooks. The hook protrusions 146 further assist the locking function of the hook and pins.

Figure 44:
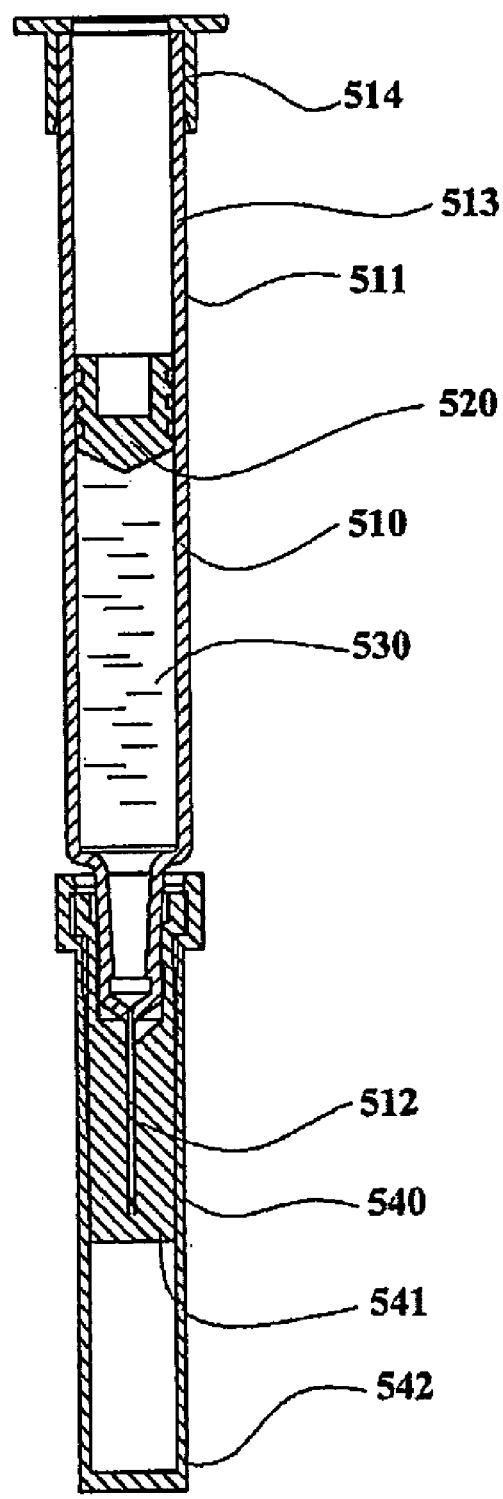
FIG. 44 is a view similar to that of FIG. 37, but showing an alternative approach for creating flanges.

An alternative embodiment of the present invention could have a different cartridge as illustrated in FIG. 44. The barrel 510 of the cartridge is lacking the flange. A flange 514 is added to the cartridge assembly.

Figure 45:
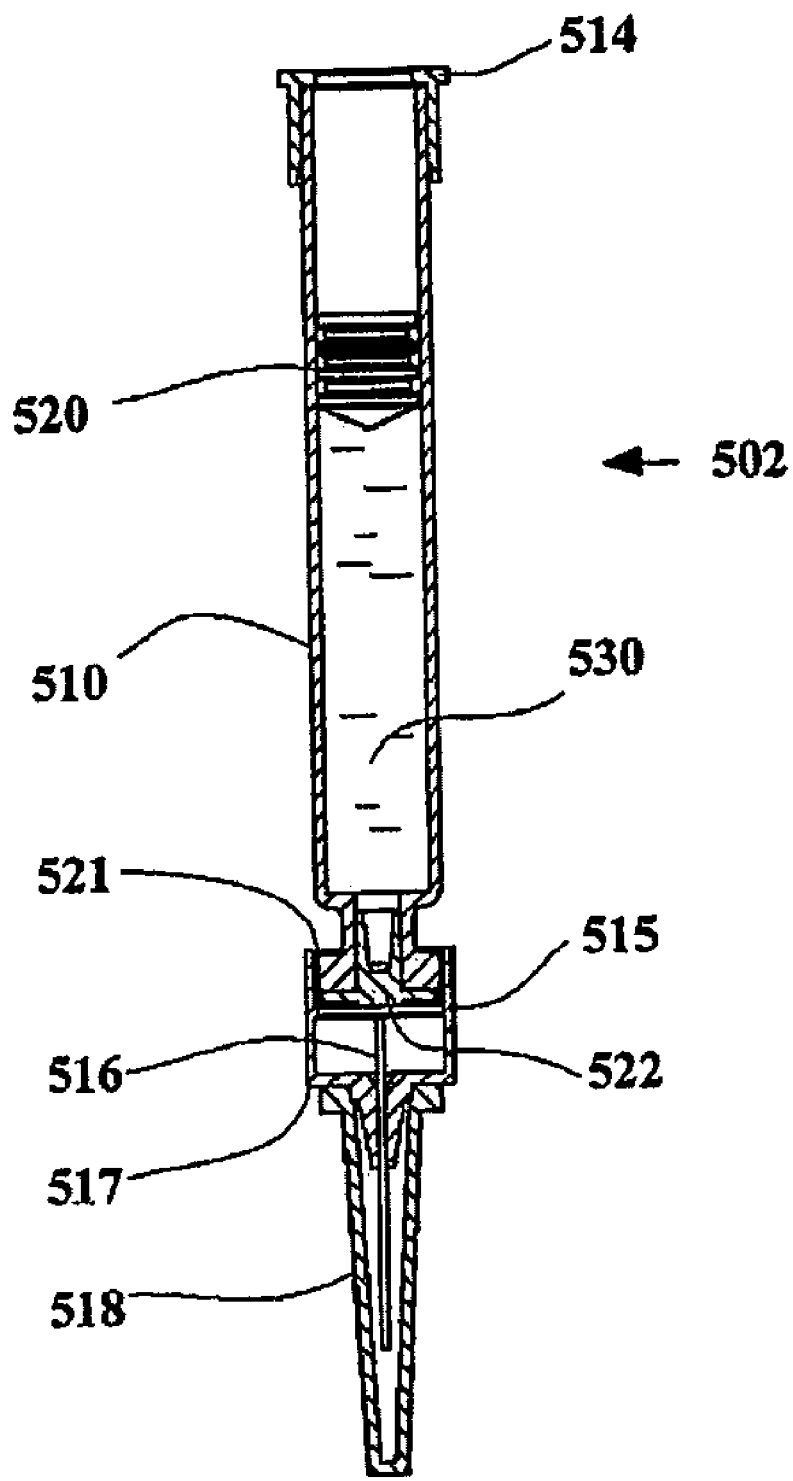
FIG. 45 is a view similar to that of FIG. 37, but showing an alternative cartridge with double sided needle.

Another alternative embodiment of the present invention could have a different cartridge as illustrated in FIG. 45. The barrel 510 of the cartridge is lacking the flange. A flange 514 is added to the cartridge assembly. Furthermore, the needle is activated (pushed to penetrate the stopper 522 for titration and drug delivery).

The exemplary embodiments show each injector having a distal end from which the needle is exposed, and a proximal end opposite the distal end. In the exemplary embodiments, the injector deploys its needle with user assist, delivers the drug in the cartridge and shields the needle. Preferably the injector provides a distinct end of delivery indication (e.g., a "click-type" effect and associated tactile feedback). The injector can be assembled around a cartridge. As a further feature of some exemplary embodiments, the cartridge includes a stopper that can be moved within the syringe barrel for titration by a rod, a threaded back rod, or a ratcheted rod. The rod can be moved in one direction only for titration. It is not connected to the stopper or the driver and allows for unimpeded delivery.

Figure 46:
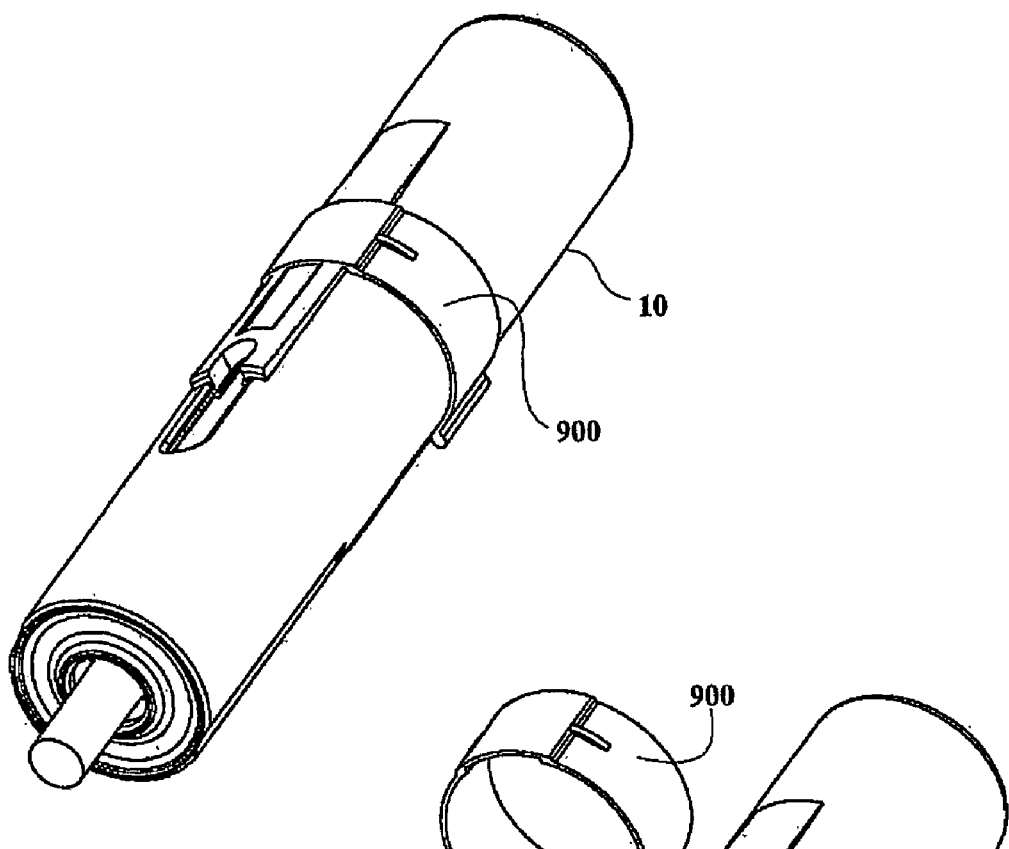
FIG. 46 is a view of the automatic injector of an exemplary embodiment of the invention with the shield sliding on the housing with the safety clip.
Figure 47:
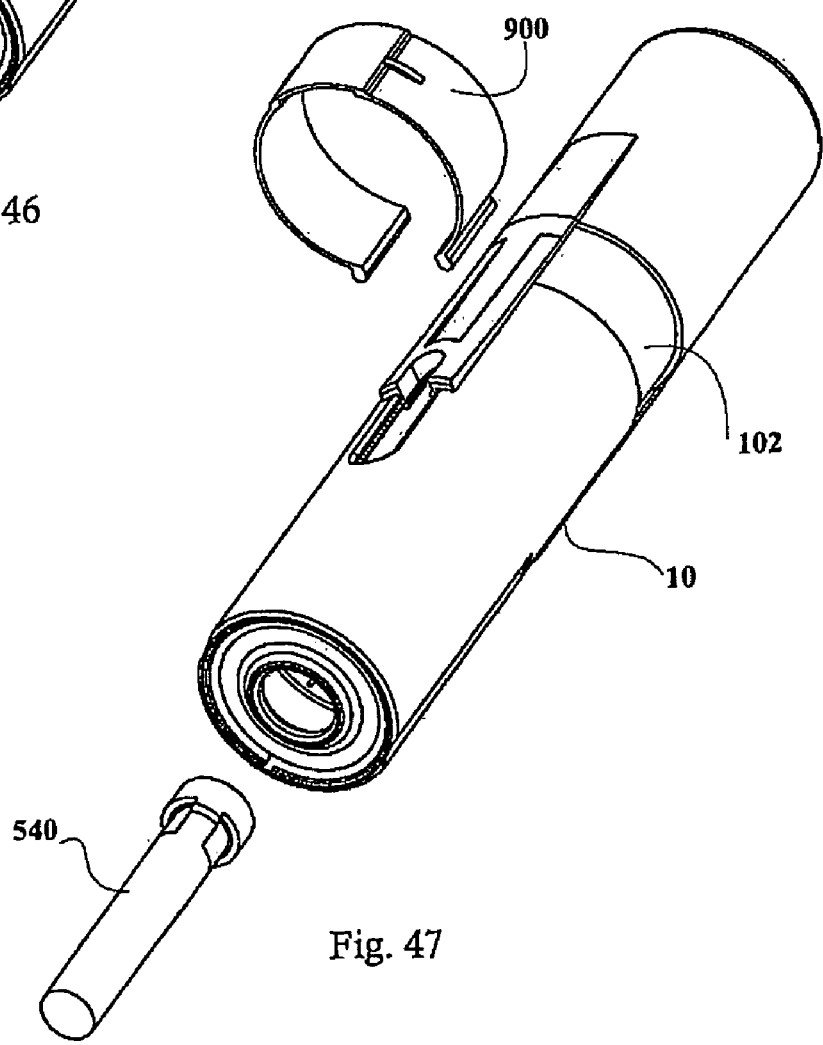
FIG. 47 is a view of the automatic injector of an exemplary embodiment of the invention with the shield sliding on the housing with the safety clip removed.

The injector provides various safety features for minimizing potential exposure of the needle. These features include false activation prevention mechanisms. In particular, a safety ring 900 is illustrated in FIG. 46 and FIG. 47 and provides this function. The ring 900 prevents activation of the automatic injector. Only after the ring is removed is the activation possible.

Alternatively, the high force for moving the shield at the beginning of use prevents premature displacement of the shield. Furthermore, the needle-locking mechanism locks the needle after use. The injector optionally includes damping material (e.g., the bushing, shock absorbing tab) for shock and noise reduction. The injector provides linear rate control using a low elasticity constant spring, preferably in the form of an expansion spring. The expansion spring can be made longer so that the cartridge stopper moves over a small longitudinal range compared to the length of the spring, thereby allowing the force of the spring to be consistent over the smaller range.

The delivery devices of the exemplary embodiments allow for accurate titration and measurement of the amount of compound to be injected. Moreover, since the end of delivery is clear, no eye contact is required for indication of the end of delivery, thus making the delivery easier when the user cannot see the observation window.

As a person skilled in the art would readily understand, delivery of the fluid drug is determined not only by the driving unit or spring. It also depends on fluid properties and the fluid's path geometry. Therefore, delivery curves will not be identical to spring reaction curves. The fluid acts as a hydraulic damper and its resistance to flow is related to the force applied to it.

The driving unit in the exemplary embodiments can be a spring. The compression spring is preferably used in the embodiments having a substantially symmetrical housing cross-section. The required motion range and the accumulated thickness of the coils limit this initial compression.

The driving spring is the most available element to control delivery. The main feature provided from the spring is a low elasticity constant. A low constant provides a more uniform delivery profile, more flexibility in controlling delivery duration, spring load reduction during shelf life, and it provides sufficient force at the end of the injection cycle. Using long springs provides the benefit of improving delivery time control and profile by changing the spring's constant of elasticity and by allowing preloads.

Moreover, this invention overcomes other problems associated with the prior art. For example, the driver and springs overcome the problems of needle phobia and needle injury. In addition, the injectors include a rod that provides the advantage of titration to allow a patient to measure and self-administer a dosage via an automatic injection system, with the rod automatically separating from the stopper before delivery.

The injectors with a rod also enable the user to minimize residual drug in the system and to eliminate air bubbles that may otherwise be trapped in the automatic system prior to use. Further, the window provides the user with the ability to see dosage formulation prior to use, and to see that the drug has been delivered after use.

It should be apparent from the aforementioned description and attached drawings that the concept of the present application may be readily applied to a variety of preferred embodiments, including the exemplary embodiments disclosed herein. For example, other driving and retraction units, such as elastomeric "O" rings or compressed gas may be used in place of the compression springs disclosed herein to bias the driver, as readily understood by a skilled artisan.

Figure 48:
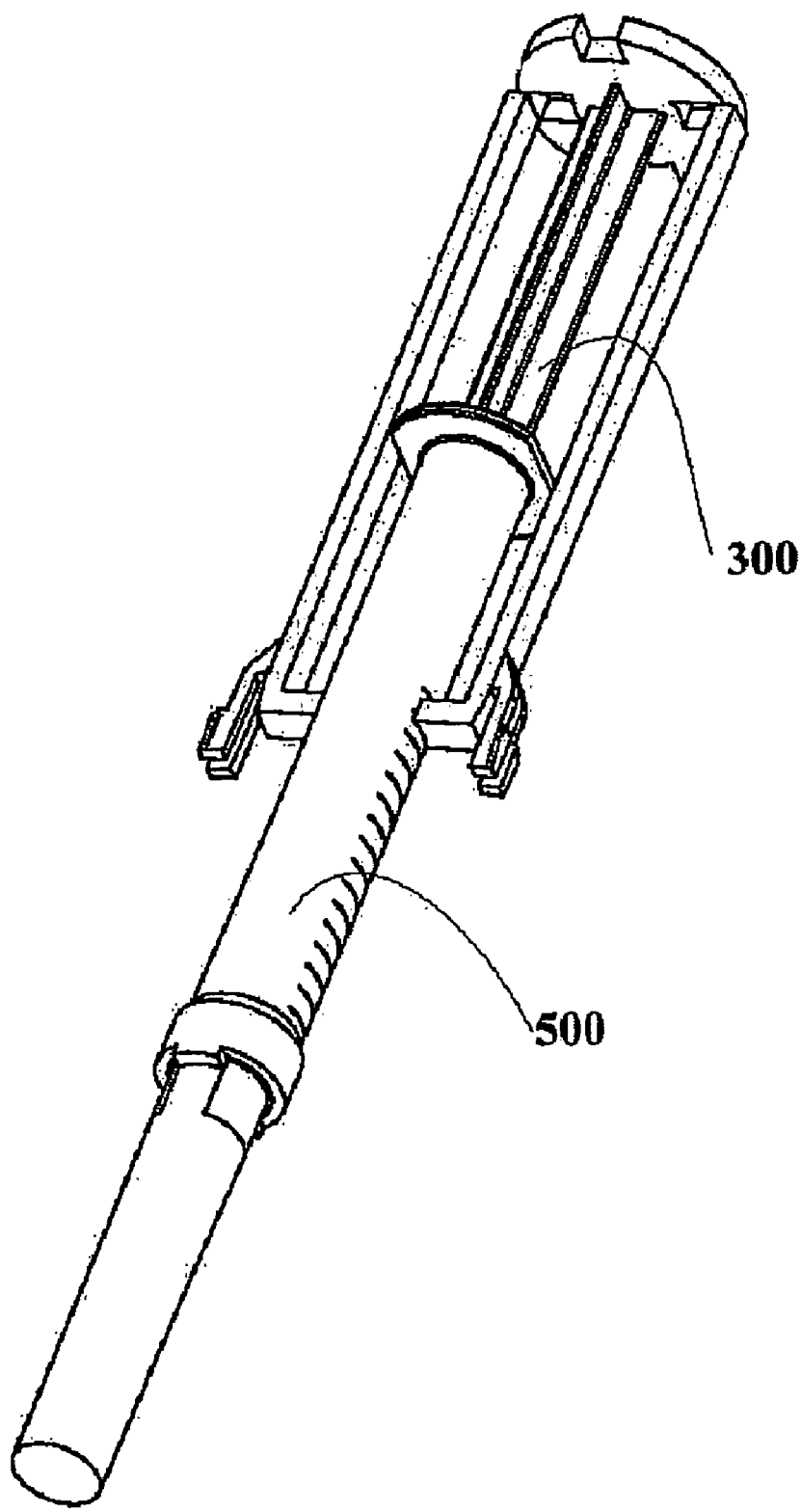
FIG. 48 is a view of the cartridge and driver sub-assembly.
Figure 49:
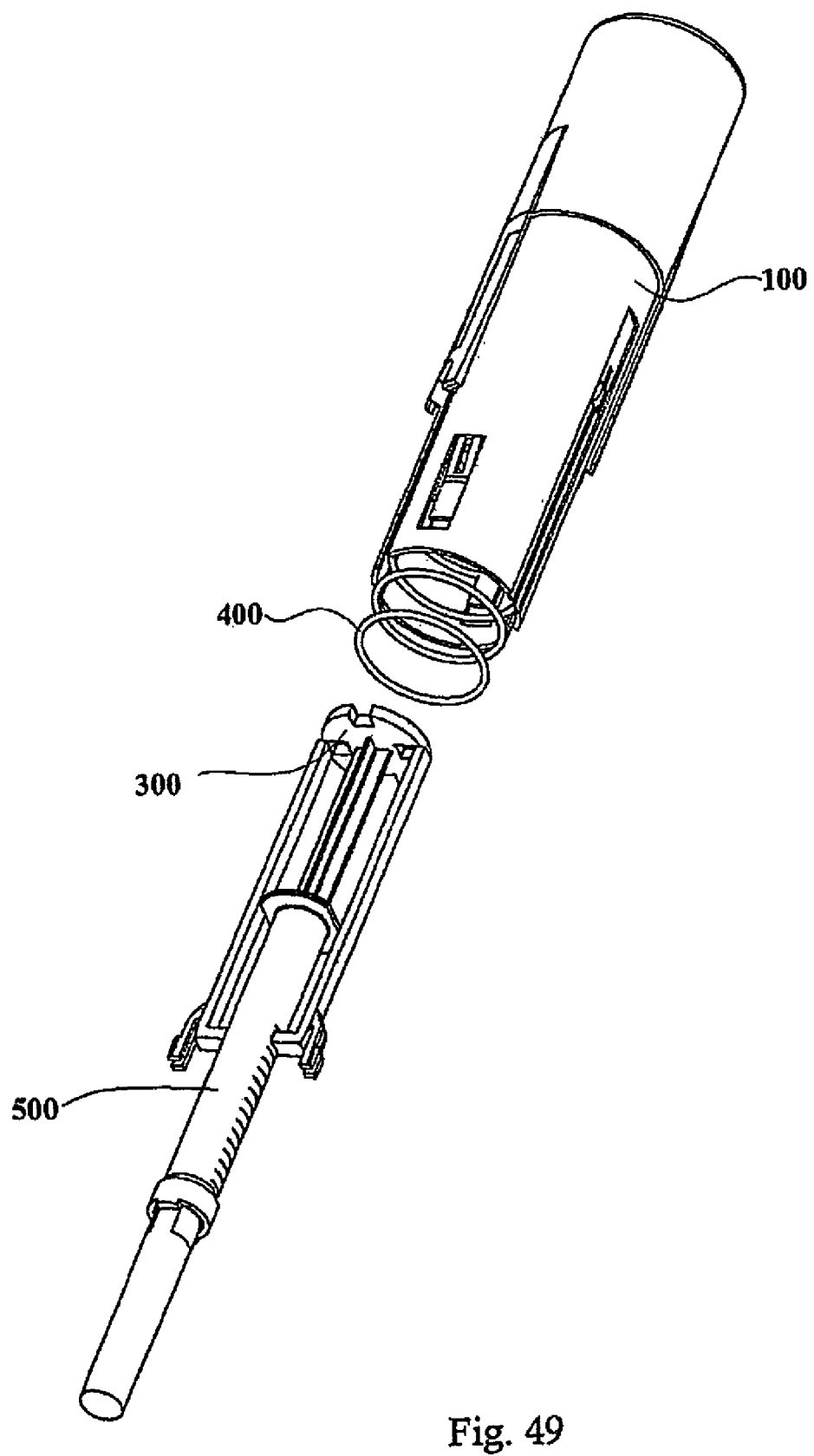
FIG. 49 is a view of the assembly process of the cartridge/driver and housing/spring sub-assemblies merger.
Figure 50:
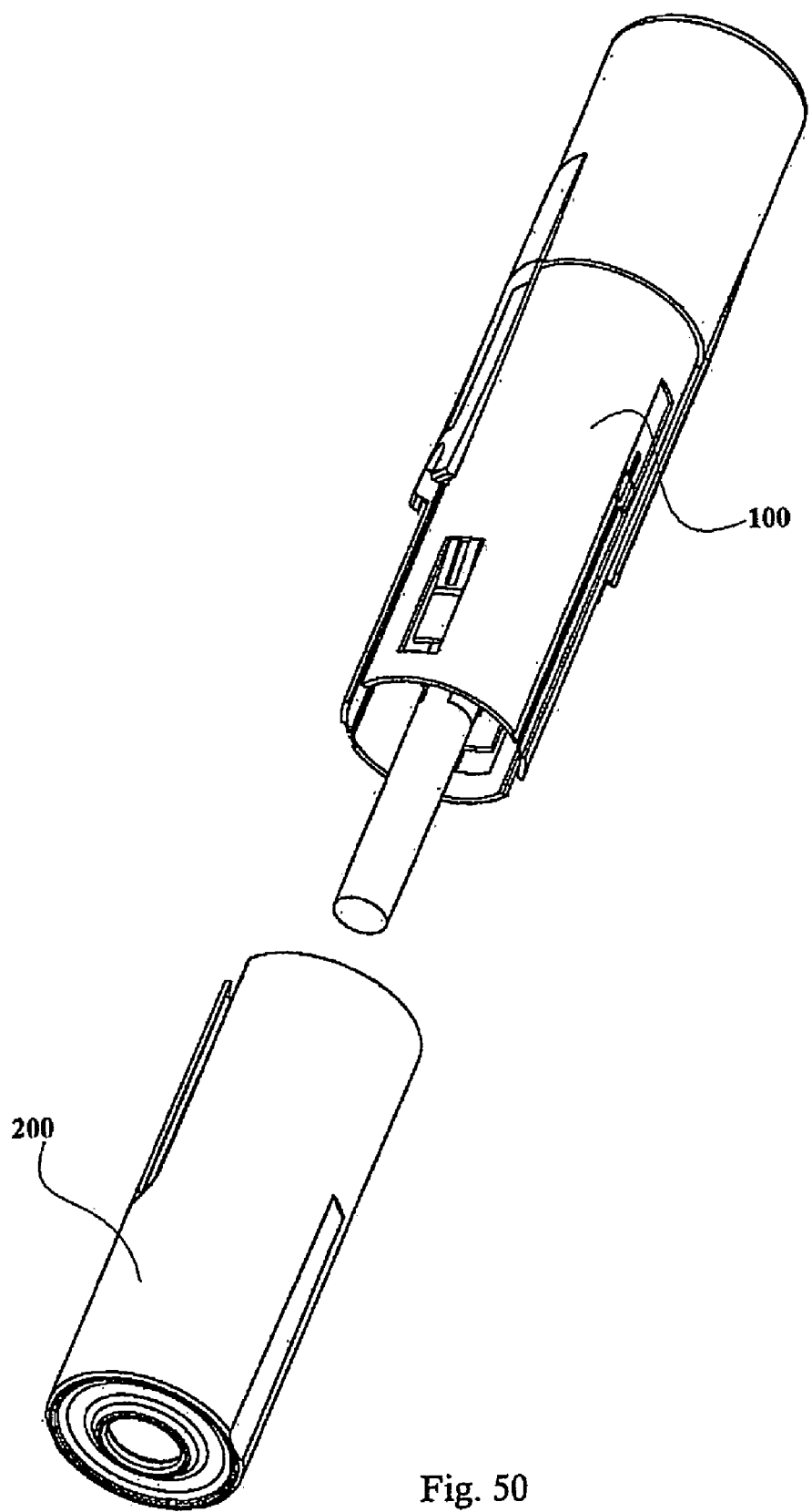
FIG. 50 is a view of the final assembly step of merging the shield with the sub-assembly from FIG. 49.

The assembly process for the exemplary embodiment is illustrated in FIG. 48 through FIG. 50. The initial step includes the assembly of the cartridge 500 with the driver 300. The spring 400 is assembled with the housing 100. The driver/cartridge subassembly is merged with housing/spring subassembly. Adding the shield completes the automatic injector. The assembly process is simple due to the small number of components.

Figure 51:
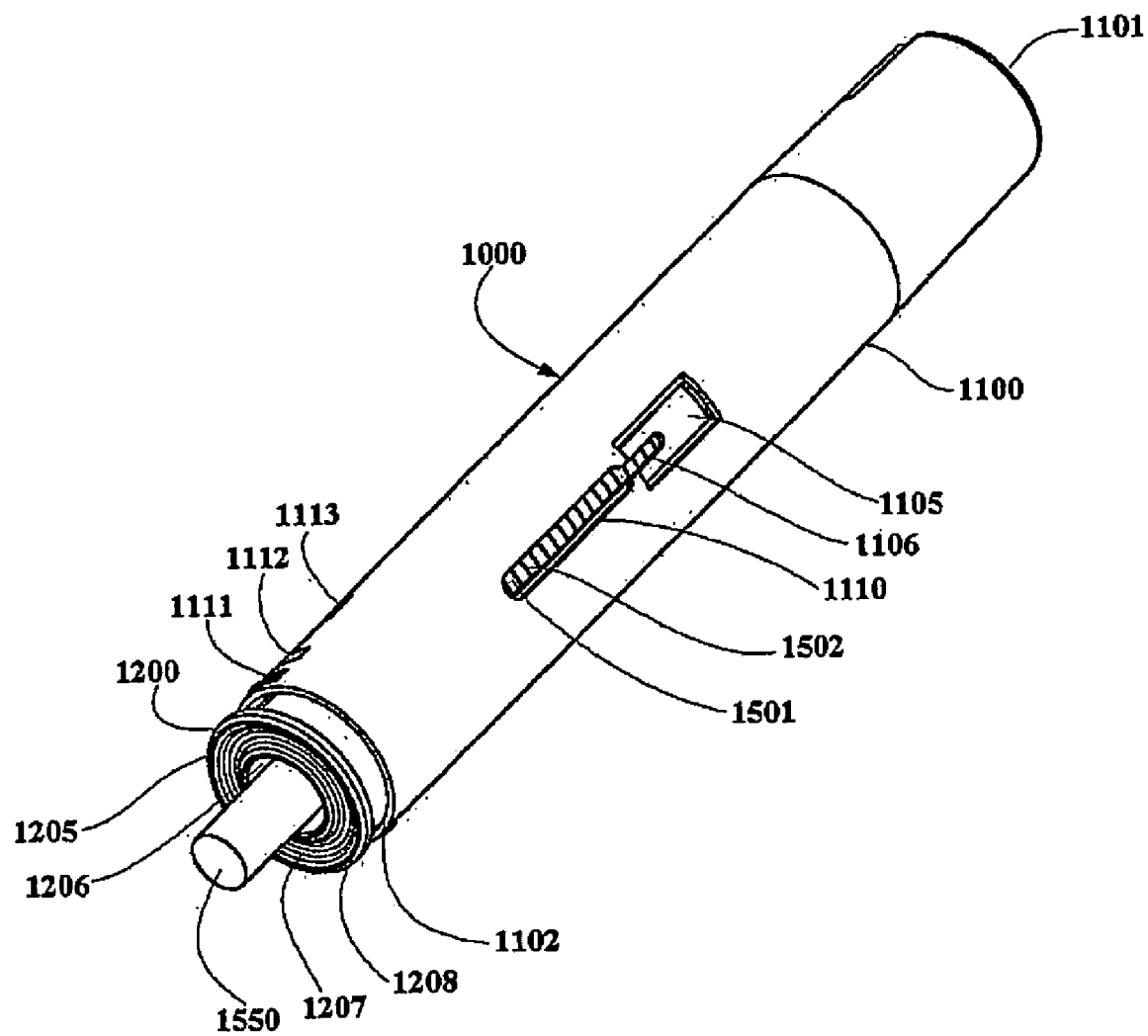
FIG. 51 is an external view showing an injector in accordance with an exemplary embodiment of the invention.
Figure 52:
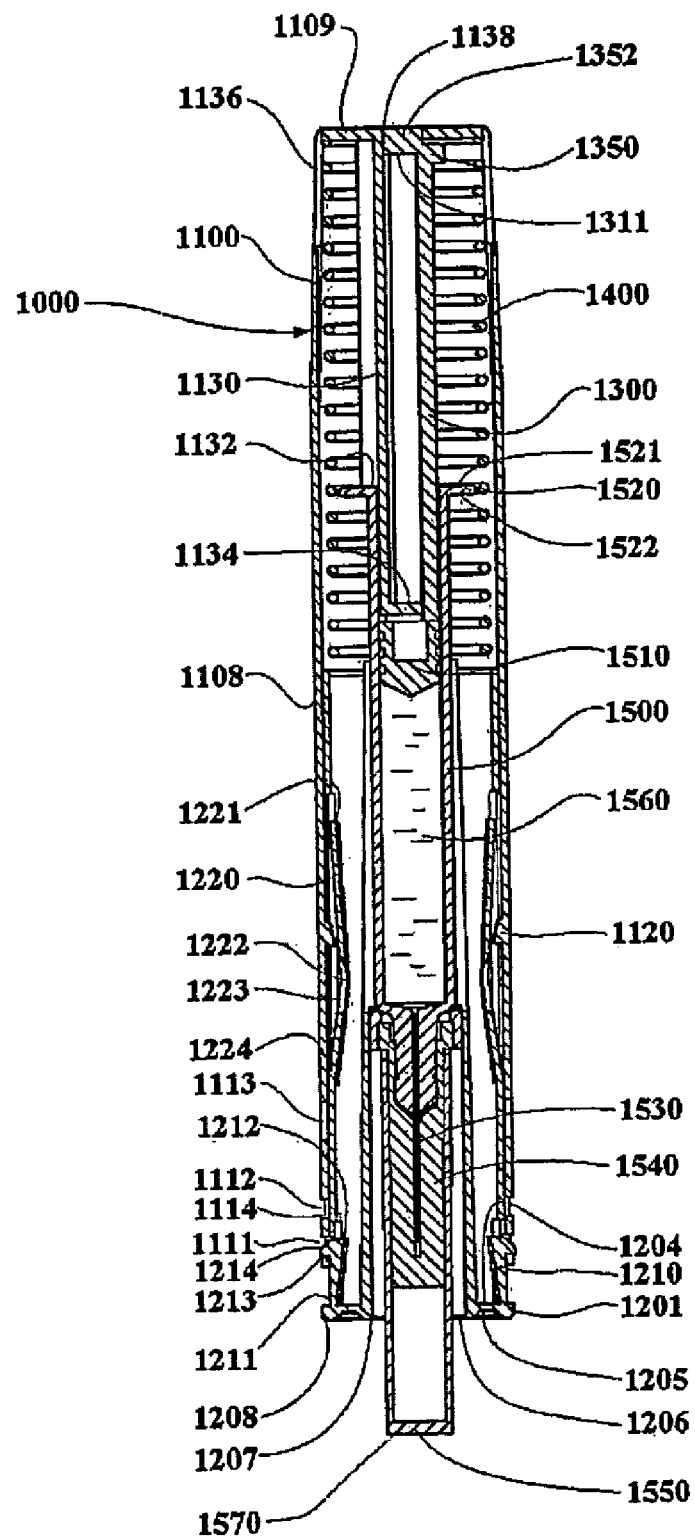
FIG. 52 is a longitudinal section view showing an injector in accordance with an exemplary embodiment of the invention in it's storage position illustrating the cartridge axial support by the housing, the delivery and discard locking elements.

Referring now to FIGS. 51-81, there is shown at 1001 an automatic injector constructed in accordance with a further exemplary embodiment of this invention. In particular, the injector 1001 includes a housing 1100, a shield 1200, a driver 1300, a cartridge 1500, and a driving unit 1400. The housing 1100 is interfaced with the shield 1200 forming a storage enclosure for the cartridge 1500 as is shown in FIG. 52. Externally the automatic injector represents a pen like cylindrical structure as is illustrated in FIG. 51. The injector 1001 has a distal end 1206 from which the needle is exposed for delivery, and a proximate end 1101 opposite the distal end 1206.

Figure 53:
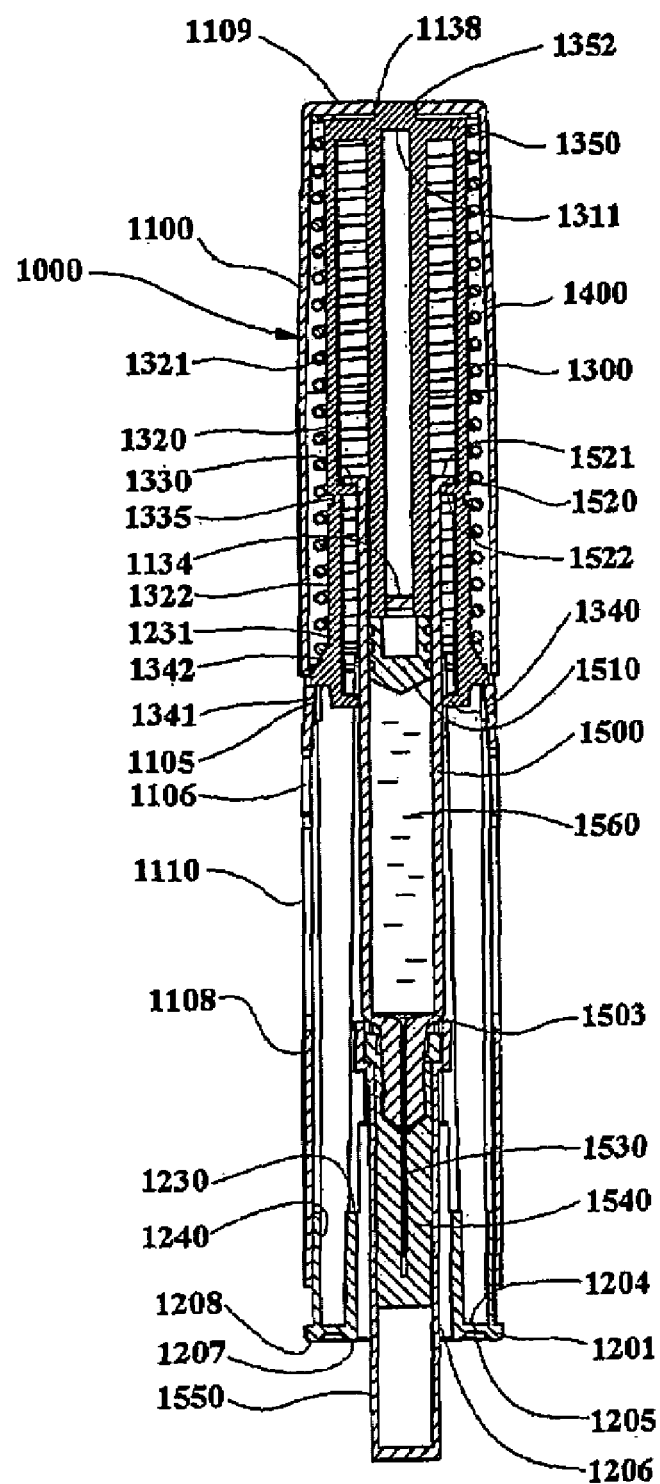
FIG. 53 is a longitudinal section view showing an injector construed in accordance with an exemplary embodiment of the invention in it's storage position illustrating the driver.

The assembly in a storage position is illustrated in FIG. 52 and FIG. 53. The housing 1100 and the shield 1200 form an enclosure housing the driver 1300 and the driving means 1400. The driving means is conventionally a spring 400 as illustrated in FIG. 52 and FIG. 53. The driver is maintained in its initial position through the interlock with the housing. The driver is preloaded by the compressed spring 1400.

Cartridge 1500 is positioned inside the housing. It is supported by the driver 1300 from moving in radial directions and in axial direction from moving toward the distal end of the injector. The edge 1132 of the internal housing arm 1130 prevents axial cartridge motion in the proximal direction. The cartridge is retained by the driver 1300 through the interface of the barrel flanges 1520 and cartridge followers 1330 contacting the outside of the barrel and the barrel flange 1520.

The first step in the use of the automatic injector is the removal of the needle cover assembly 1570 of the needle 1530 illustrated in the embodiment. The needle cover assembly 1570 could consist of one component, an elastomeric protective cup 1540. Alternatively the protective cover assembly could also include a second component, a rigid plastic protector 1550. The needle cover assembly 1570 of the needle 1530 protrudes through the distal end of the auto injector (see FIG. 51, FIG. 52 and FIG. 53). It is removed from the injector prior to use. Protective needle cover assembly 1570 also prevents the shield 1200 from accidental impact before use of the auto-injector to prevent false activation.

The driver 1300, housing 1100 and the shield 1200 have a set of features intended to facilitate the engagement during storage and disengagement of the driver from the housing during activation at a force defined below. The operation of the automatic injector will become clear from the following detailed description of the automatic injector components and component interactions.

The driver in the exemplary embodiment of the invention is initially engaged to the housing as illustrated in FIG. 53. The secure engagement prevents accidental release of the driving spring during storage or transportation.

Figure 54:
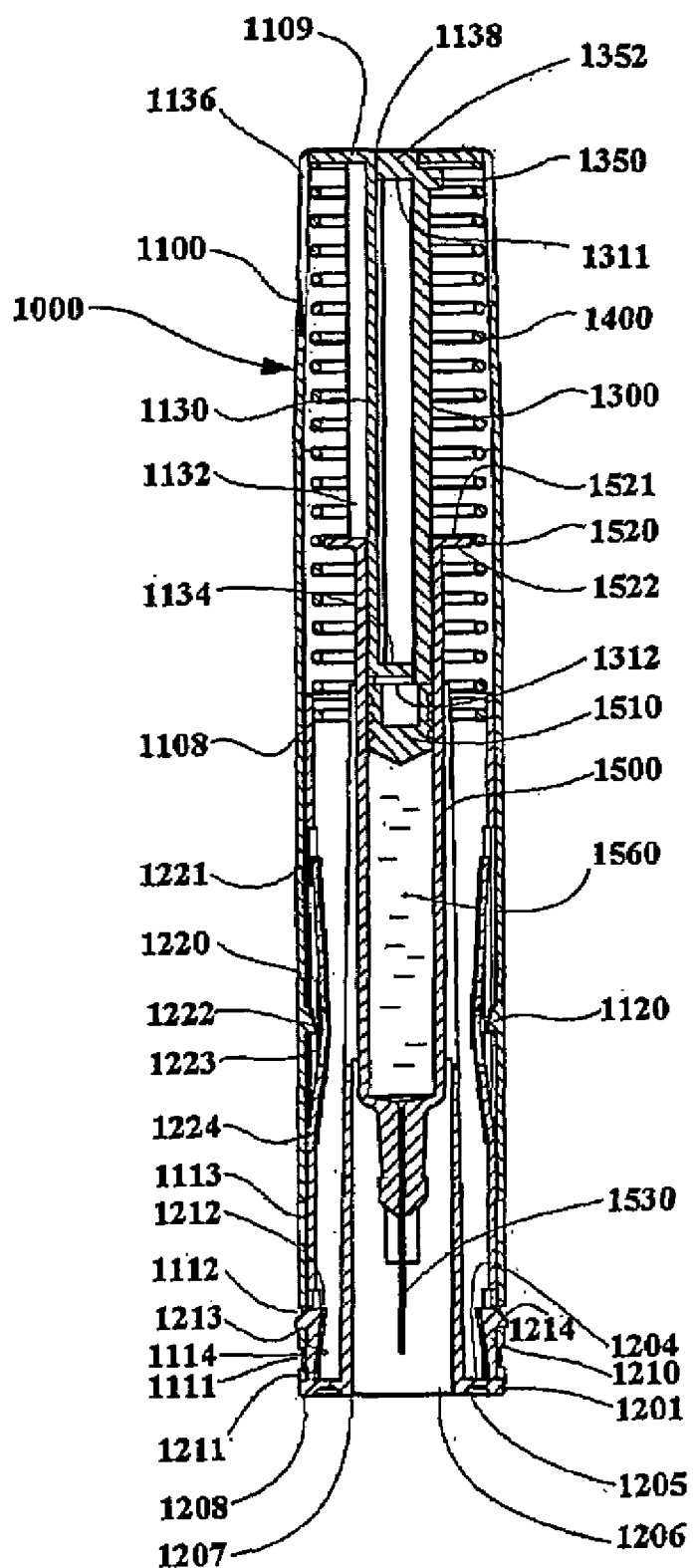
FIG. 54 is a view similar to that of FIG. 52, but showing the injector in a state wherein the protective needle cover assembly is removed, the distal end is pushed against an injection site, the shield is engaged to the housing in the second position, the device is activated.

The action of shield displacement by the user is performed in two stages. Initially the user applies a substantial force with minimal displacement. The threshold force is controlled by two areas of interaction between the shield 1200 and the housing 1100. The first interaction is shown in FIG. 52 and 54 and in more detail in FIG. 74 and FIG. 75. The shield 1200 has locking hooks 1210. Hooks 1210 could bend at its narrow cross-section 1211. When the base of the shield 1205 is pushed against the injection site the leading slope of the shield hook 1214 is held in place by the inner edge 1114 of the storage slit 1111. An axial force is created initially with minimal displacement. Only when shield hook 1210 starts bending at 1211 will surface 1214 slide on 1114.

Figure 55:
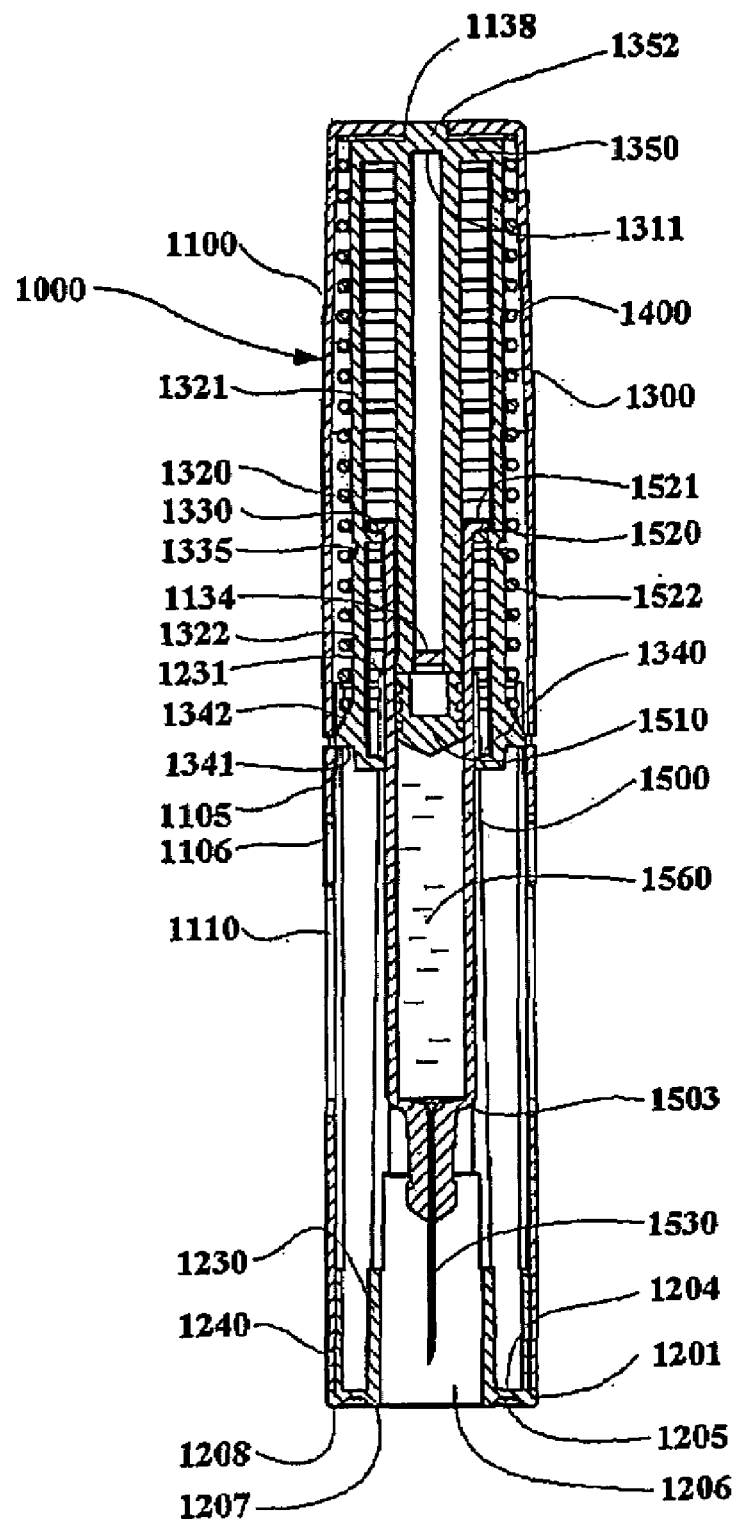
FIG. 55 is a view similar to that of FIG. 53, but showing the injector in a state wherein the protective cap is removed, the distal end is pushed against an injection site, the device is activated.

A further increase in the force applied by the user leads to the second stage. During the second stage the driver is disengaged from the housing by the shield as is shown in FIG. 53 and 55 and further detailed in FIG. 70, 71, 72 and 73. The increased force causes increased displacement of the shield with respect to the housing. During storage the leading edge 1341 rests on the edge of the housing latch 1107. The leading edge 1242 of the shield 1200 deflects the housing storage latch 1105 releasing the driver 1300. Storage latch 1105 also includes a slit 1106 providing continuation of the observation window 1110 function.

Shield 1200 further has a longitudinal slit 1241 to guide the driver cam 1340. The leading edge 1242 of the shield 1200 is positioned on both sides of the slit 1241. Therefore the radial deflection of the storage latch 1105 will release the driver feature 1342 without any interference to the distal motion of the driver protrusion 1343 and the driver 1300. After 1105 is deflected and the driver released no force is required to maintain the device in the delivery position since the holding hook 1210 will engage the delivery slot 1112.

FIG. 70 illustrates a partial cross-sectional view of the housing and driver interlock during storage. FIG. 72 shows a cross-section through the latch of FIG. 70. FIG. 71 and 73 correspond to FIG. 70 and FIG. 72 after the injector is triggered. Storage latch 1105 holds the axial spring forces during storage and yet is soft and flexible to allow the triggering. Latch 1105 will remain in its deflected position as illustrated in FIG. 55 and FIG. 73 until the device is removed from the injection site.

Once the protrusion 1343 of the driver 1300 is no longer supported by latches 1105, the driving mechanism 1400 will move the driver 1300 forward. The drive plate 1312 of the driver 1300 will push on the stopper 1510 of the cartridge 1500. The cartridge 1500 will move forward with no interference and will cause the needle 1530 to penetrate the tissue.

Figure 56:
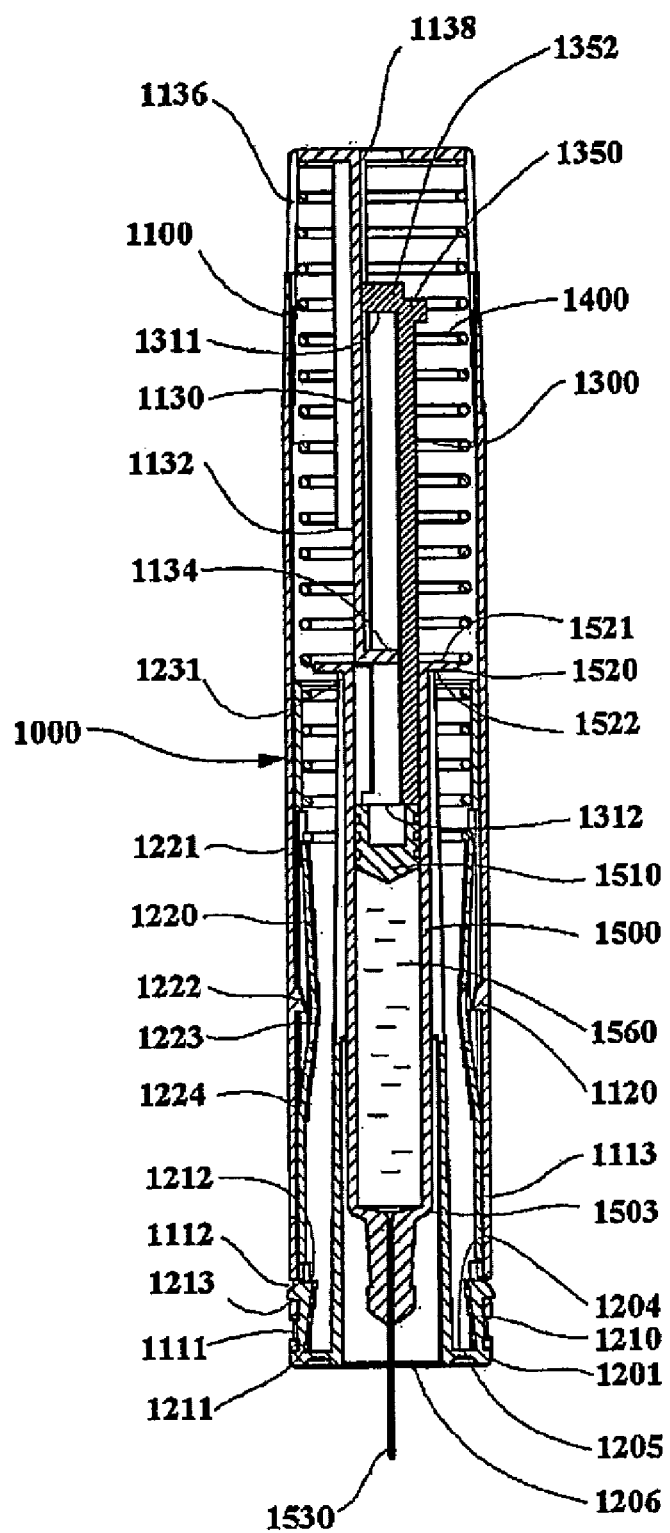
FIG. 56 is a view similar to that of FIG. 54, but showing the injector in a state wherein the cartridge is advanced toward the distal end, the needle is inserted into the tissue and the injection is initiated.
Figure 57:
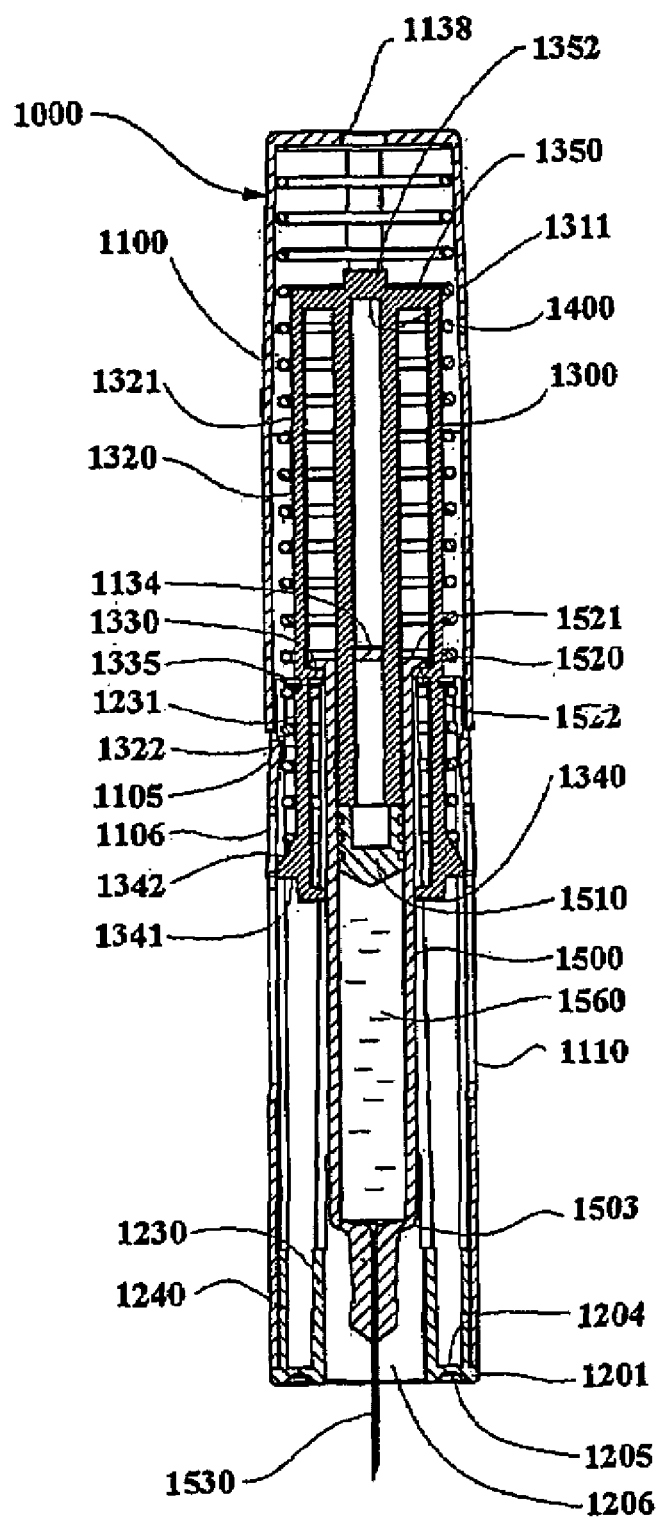
FIG. 57 is a view similar to that of FIG. 55, but showing the injector in a state wherein the cartridge is advanced toward the distal end, the needle is inserted into the tissue and the injection is initiated.

The cartridge 1500 is subjected to three force components: needle insertion into tissue, cartridge to housing friction and stopper to barrel friction. The insertion force of the injection cannula 1530 is low and is in the range of few tenths of grf (gram-force). The static friction between the stopper 1510 and the glass barrel 1501 is variable but in most cases is substantially higher than the resistance to the needle penetration. The cartridge to housing friction is low. Another factor is the hydraulic impedance of the drug path through the cannula 1530. The typical force applied by the driving mechanism 1400 for injection will be over 100 grf. The relatively low forces required for needle insertion and cartridge friction against housing force ensure full needle penetration before the drug delivery is initiated. FIGS. 56 and 57 show the needle at full penetration. The needle penetration into tissue stops when the distal flange side 1522 of the cartridge flange 1520 reaches the edge 1231 of the central shield protrusion 1230. The force applied by the driving mechanism is acting though the driver 1300 on the stopper 1510 pushing the drug into the tissue. The driver is moving together with the stopper with the drug delivered until the cartridge is empty.

Figure 58:
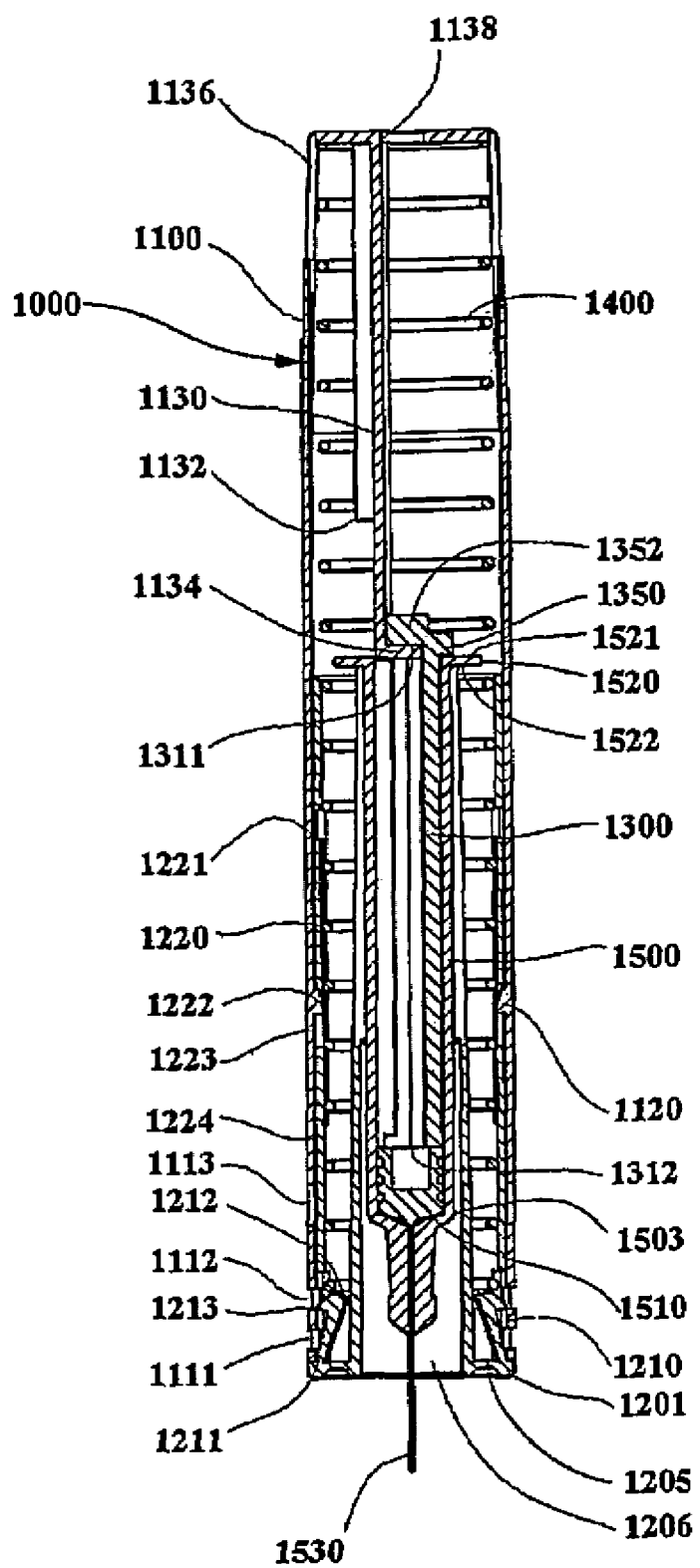
FIG. 58 is a view similar to that of FIG. 56, but showing the injector in a state wherein the delivery is completed, spring bypasses the driver and impacts the shield.
Figure 59:
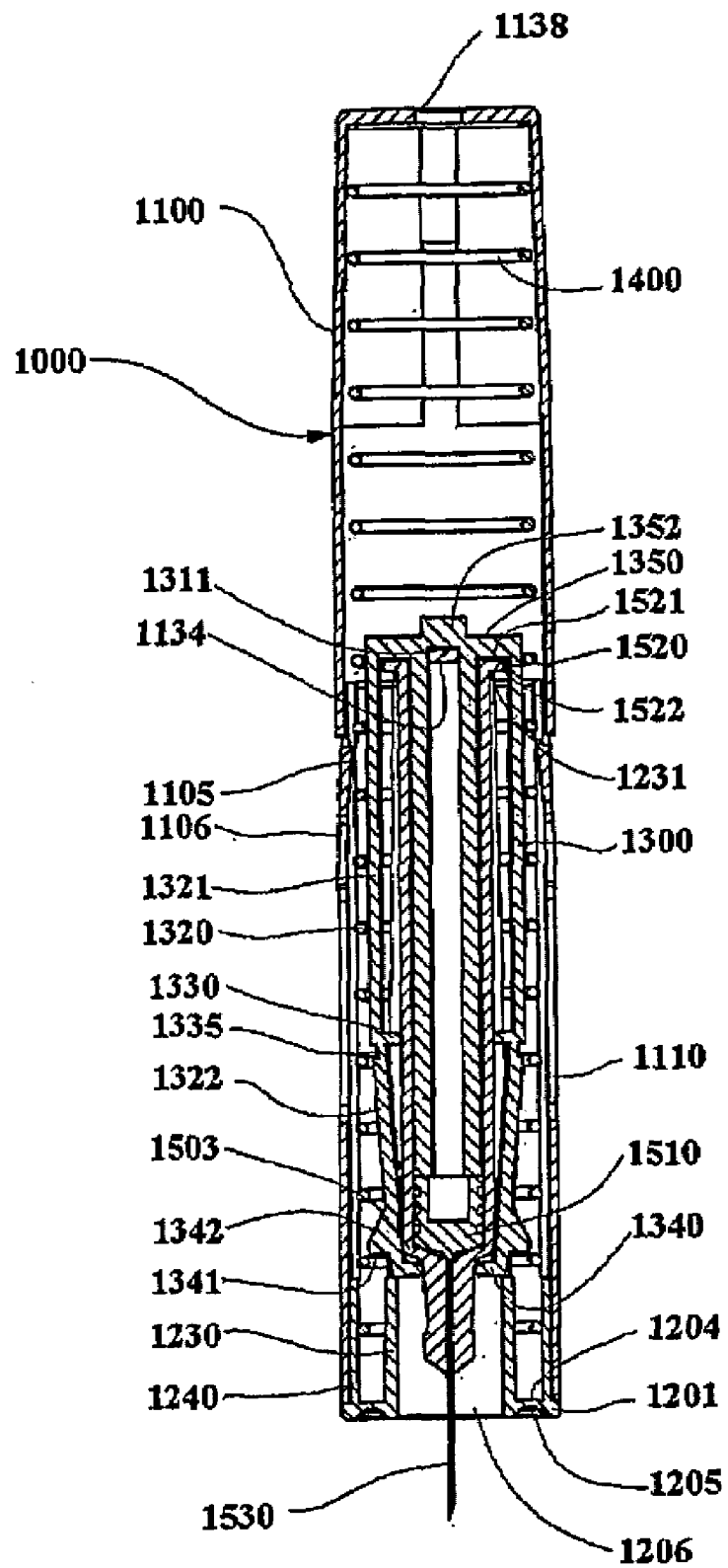
FIG. 59 is a view similar to that of FIG. 57, but showing the injector in a state wherein the delivery is completed, spring bypasses the driver and impacts the shield.

FIG. 58 and FIG. 59 show the device after the end of delivery. The cartridge follower 1340 slides off the end of the barrel 1503. The front section of the arm 1322 deflects inward releasing the spring 1400. Once spring 1400 is released it bypasses the driver 1300. At this position the driver is stopped by the delivery support 1134 of the housing arm 1130 blocking further driver travel. The driver retains the cartridge. The spring 1400 bypasses the driver and applies a radial outward force on a discard latch 1220 in knee point 1222. Once 1220 is pushed aside it is slightly expanded until edge 1221 touches the inner diameter of the housing 1100.

After bypassing the driver protrusions 1343 the driver spring 1400 impacts the outer surface 1212 of the shield locking hook 1210. The radial distance from the impact point of the spring 1400 on the hook 1212 to the rotational axis point 1211 of the hook latch creates a rotational moment that bends locking hook 1210 inward. Bending in of hook 1210 unlatches the hook 1210 from delivery slit 1112. The shield 1200 is free to slide in the distal direction under the force of the spring. The pressure of the spring on the hooks 1210 results in a sudden increase of force sensed by the user holding the injector at the injection site. The increased force acting on the shield provides a tactile indication to the user of the end of delivery, moves the shield to complete the shielding, and activates the locking mechanism of the shield.

Figure 60:
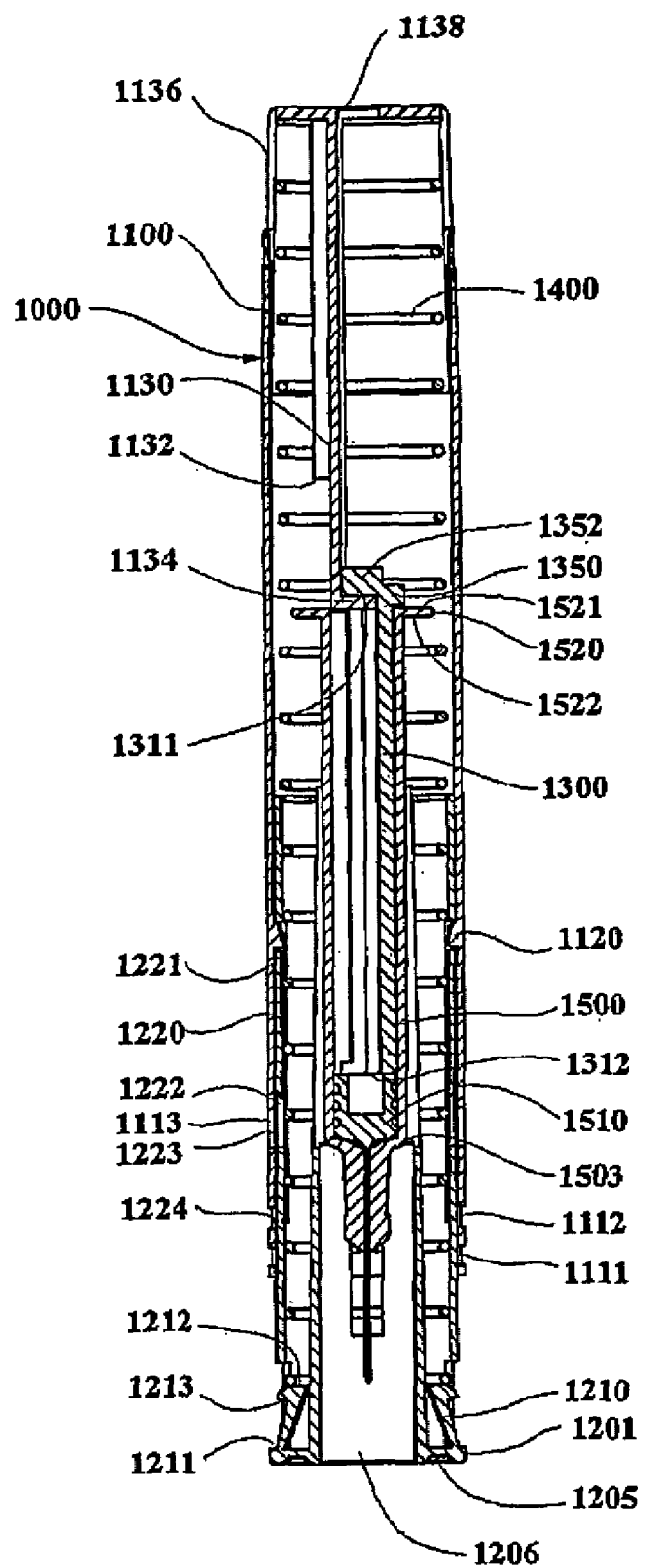
FIG. 60 is a view similar to that of FIG. 58, but showing the injector in a state wherein the shield is extended to cover the cartridge and the device is secured in it's discard position.
Figure 61:
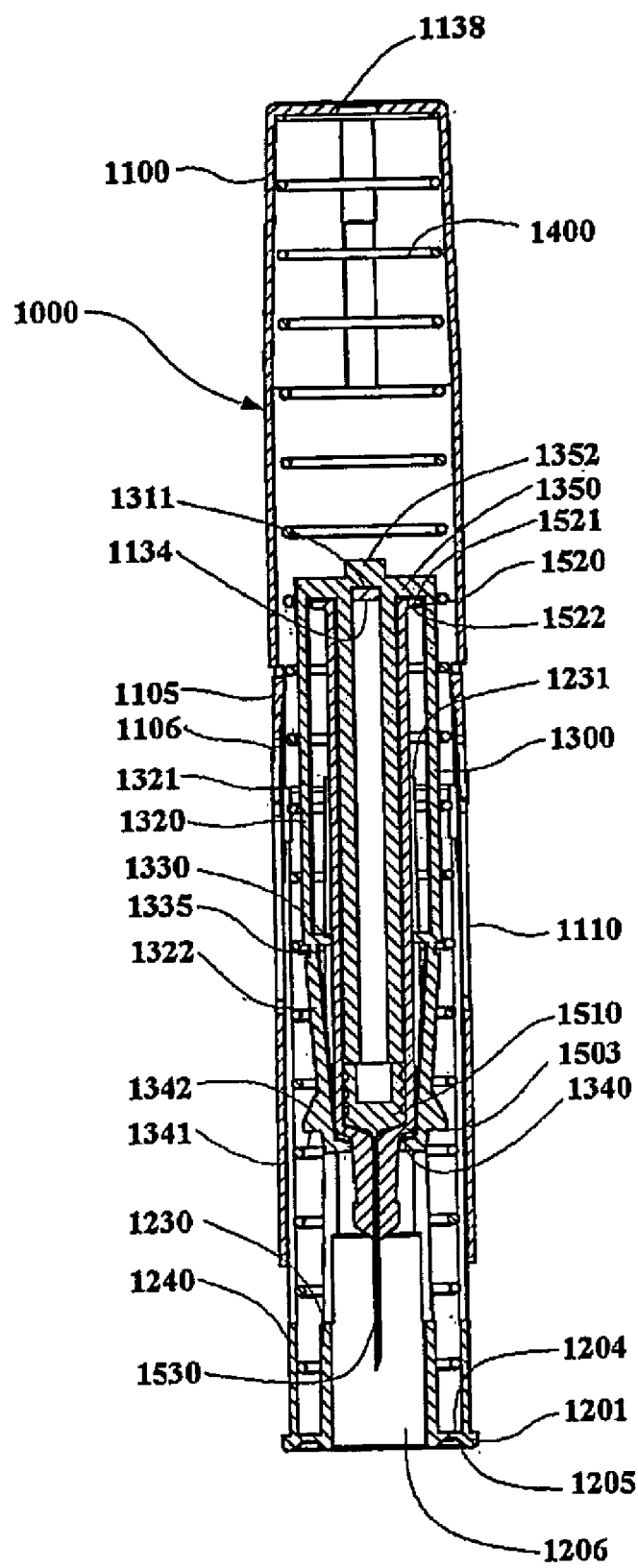
FIG. 61 is a view similar to that of FIG. 59, but showing the injector in a state where the shield is extended to cover the cartridge and the device is secured in it's discard position.
Figure 62:
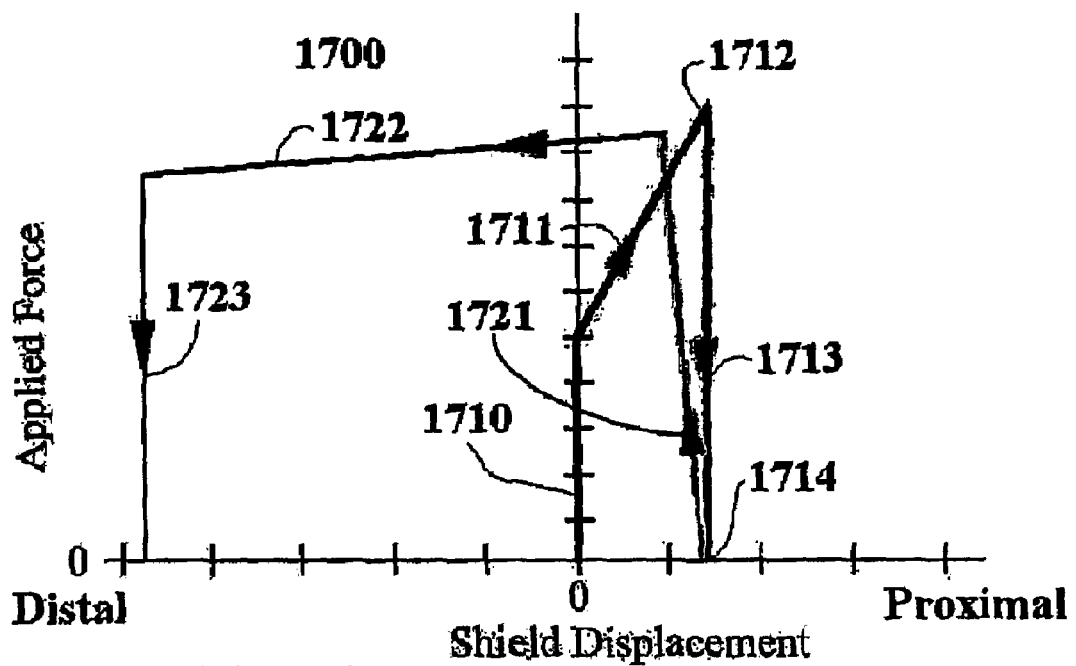
FIG. 62 is a view of a force profile in respect to the shield displacement for an injector in accordance with an exemplary embodiment of the invention.

FIGS. 60 and 61 show the device in a discard position. Discard position is reached after the device is removed from the injection site as assisted by the force of the spring applied to the shield. The removal from the injection site leads to the extraction of the needle from the tissue, and complete shielding of the needle by the shield 1200 as illustrated in FIG. 62. The discard lock is provided by the protrusion 1120 contacting the discard latch 1220. The re-exposure of the needle is prevented by the protrusions 1120. The spring 1400 applies a radial force on latch 1220 while allowing it to bend back to bypass the protrusion 1120. The latch profile makes it stiff and capable of holding an axial force while remaining flexible in radial direction.

Figure 63:
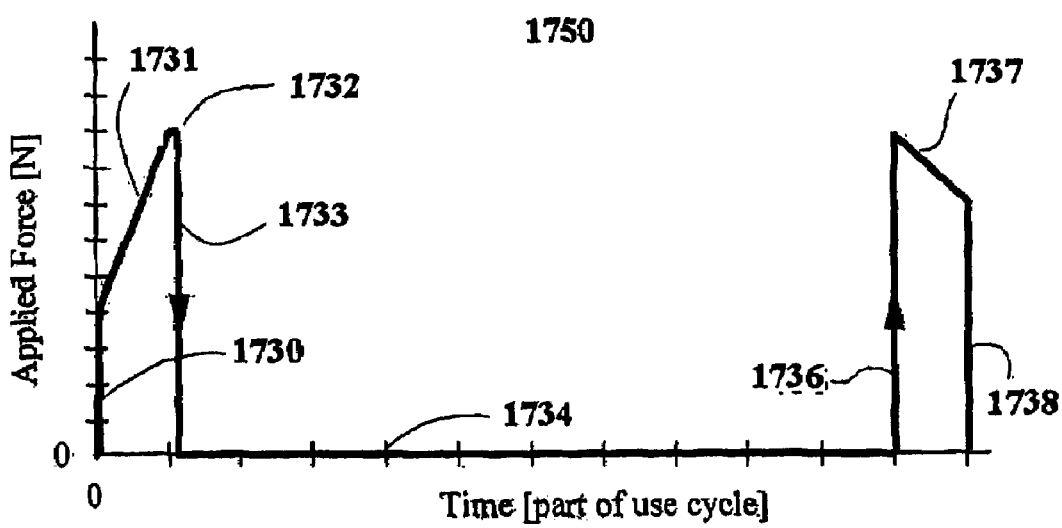
FIG. 63 is a view of a force profile in respect to the injector operation timing for an injector in accordance with an exemplary embodiment of the invention.
Figure 64:
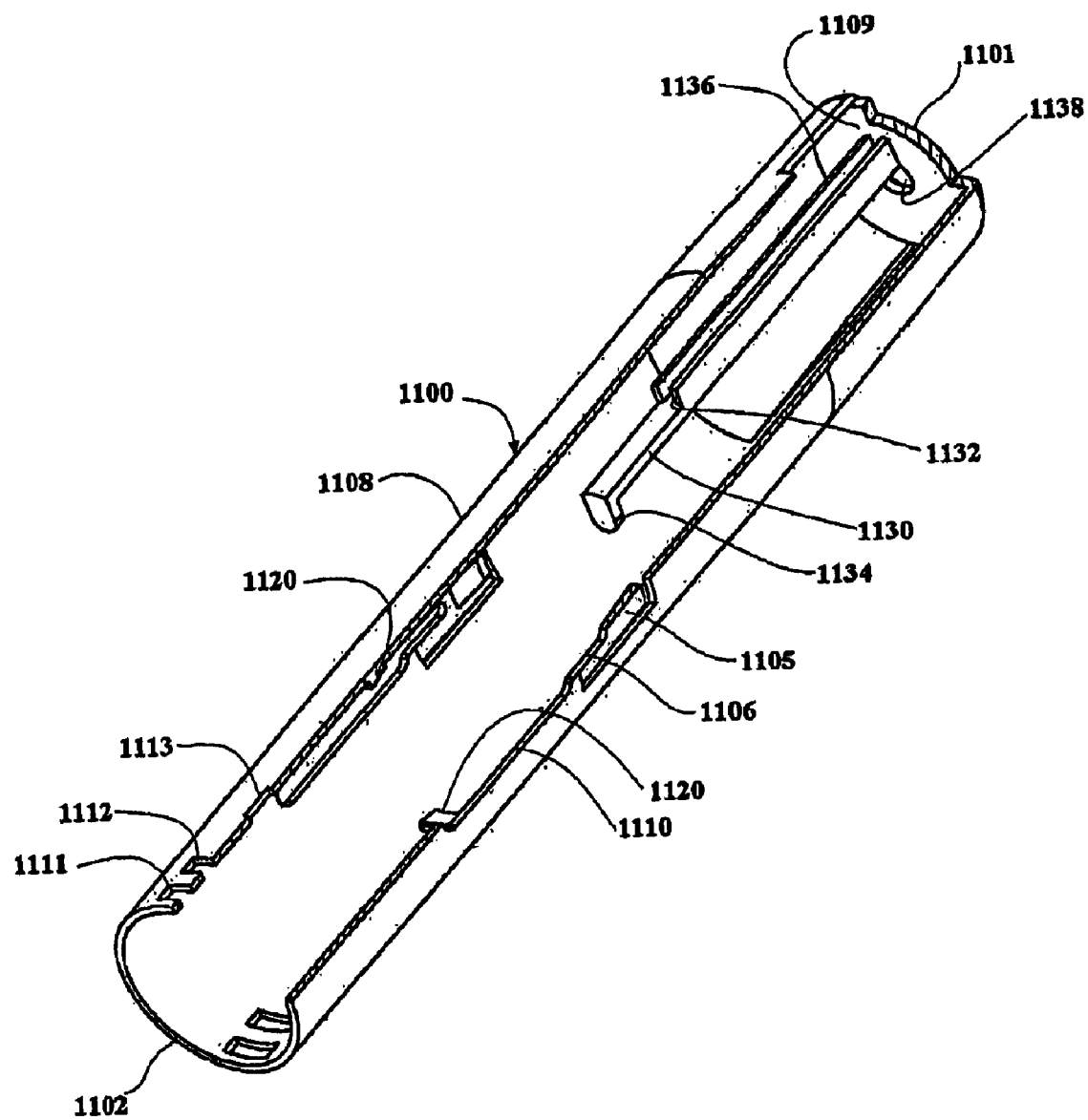
FIG. 64 is an isometric view of the exemplary embodiment of the housing with a removed section.

The forces acting on the system are detailed in FIG. 62 and FIG. 63. The displacement of the shield while pushing the automatic injector toward the injection site results in the disengagement of the driver from the housing. The displacement of the shield requires a substantial force over a short distance as shown in FIG. 62. The force required to initiate the displacement of the shield increases rapidly with practically no displacement as illustrated by 1710. Further increase in force leads to the initial displacement of the shield 1711. The maximal displacement of the shield in the proximal direction is reached at 1712. This position is illustrated in FIG. 54. At this point the driver disengages from the housing while the shield engages the housing at a new location with the hook 1210 engaging slit 1112. The force required to maintain the injector at the injection site drops to practically zero over a short travel distance 1713. The shield force remains close to zero during injection until end of delivery is achieved.

The high initial shield displacement force over a short distance assures that the shield is fully displaced and the device is effectively triggered due to the inertia of the human motion. The automatic injector requires from the user sufficient force for the shield displacement to prevent accidental triggering and to ensure effective device triggering.

After the end of delivery is achieved the user experience a sudden force increase 1721 that will cause the extraction and shielding of the needle due to the shield distal motion as illustrated by 1722. The total length of the device when discarded is longer than in storage. This is due to the distal shield extension beyond the trigger position. After the shield is extended and locked to the housing for discard the shield force drops to 0 as illustrated by 1723 in FIG. 62.

The profile of the shield displacement force as a function of time 1750 is illustrated in FIG. 63. The activation and shielding take only a relatively short time. The injection time is relatively long as illustrated by 1734. Elements 1730, 1731, 1732, 1733, 1734, 1736, 1737 and 1738 correspond respectively to 1711, 1712, 1713, 1714, 1721, 1722 and 1723 in FIG. 62.

The automatic injector of the exemplary embodiment has a minimal number of parts. Housing 1100 is the main structural part of the injector described in detail FIG. 64. Housing 1100 has a cylindrical section 1108 attached to a base 1109. Inner arm 1130 is attached to the housing base 1109. Cylindrical section 1108 includes storage latches 1105 and observation window 1110. The cylindrical section 1108 also includes locking slits 1111, 1112 used for interfacing with the shield 1200 and locking protrusion 1120 used for discard lock. The cylindrical housing section 1108 and the base 1109 have openings 1136 to assist in molding. Furthermore the base has a central opening 1138 to support the driver 1300 during storage.

Figure 65:
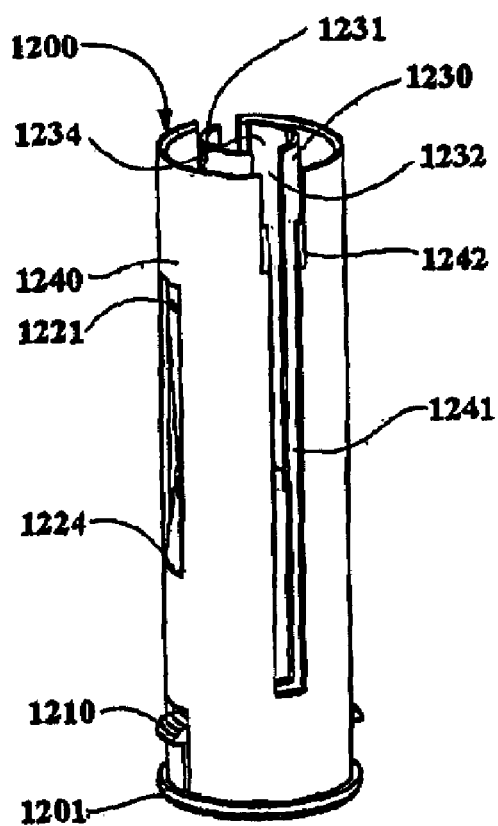
FIG. 65 is an isometric view of the shield of the exemplary embodiment.
Figure 66:
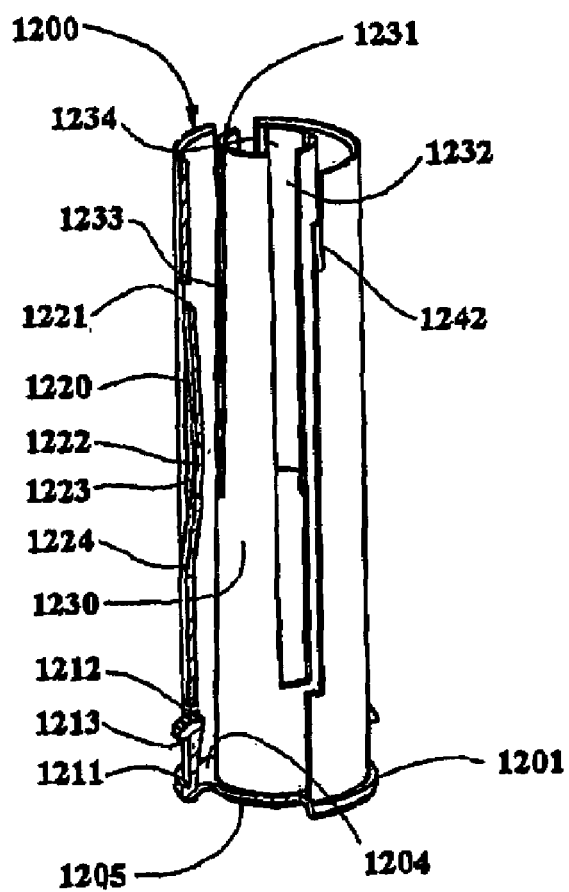
FIG. 66 is an isometric view of the shield of the exemplary embodiment with a removed section.

Shield 1200 consists of two concentric cylinder like structures 1240 and 1230 connected by base 1201 as illustrated in FIG. 65 and 66. The base 1201 has inner side 1204 and outer side 1205. The outside surface of the injector base 1205 is pressed against the injection site during use of the device. The base surface 1205 has two elevated ring like sections 1207 and 1208 to improve interface with the injection site.

The inner diameter 1234 of the inner cylinder 1230 is guiding the cartridge 1500 during operation. The edge 1231 of the inner cylinder 1230 is contacting the cartridge flange in its travel forward during the initiation of the injector operation while the needle 1530 is penetrating tissue. The external cylinder 1230 of the shield slides inside the housing 1100. The shield 1200 includes discard latches 1220 and locking hooks 1210. Slit 1241 of the outer cylinder 1202 acts as a guiding track for the driver 1300. The inner cylinder 1230 has a matching slit 1232. The slits 1241 and 1232 together with openings in the housing 1110 allow observation of the drug before use. Slits 1233 on the inner cylinder together with slits 1223 in the discard latch and slit 1113 in the housing allow observation of the status of the piston at the end of delivery when the device is in discard position.

Figure 67:
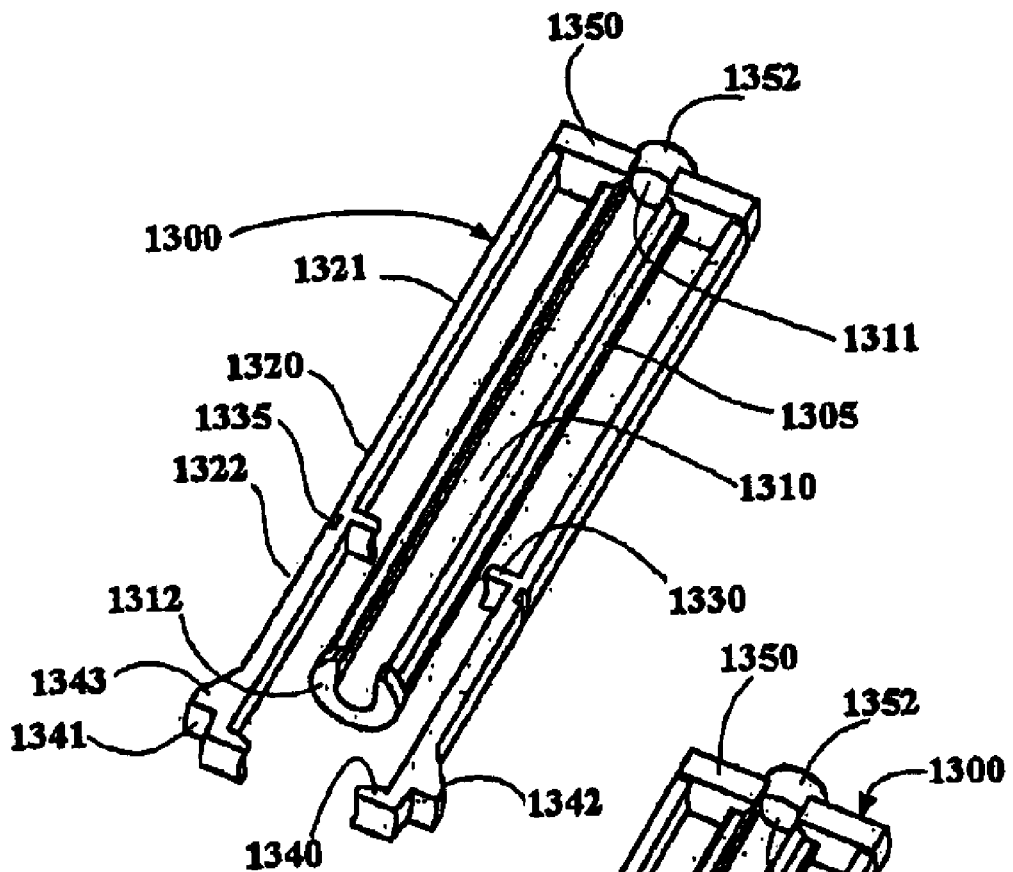
FIG. 67 is an isometric view of the driver of the exemplary embodiment as deformed when engaged to the housing.
Figure 68:
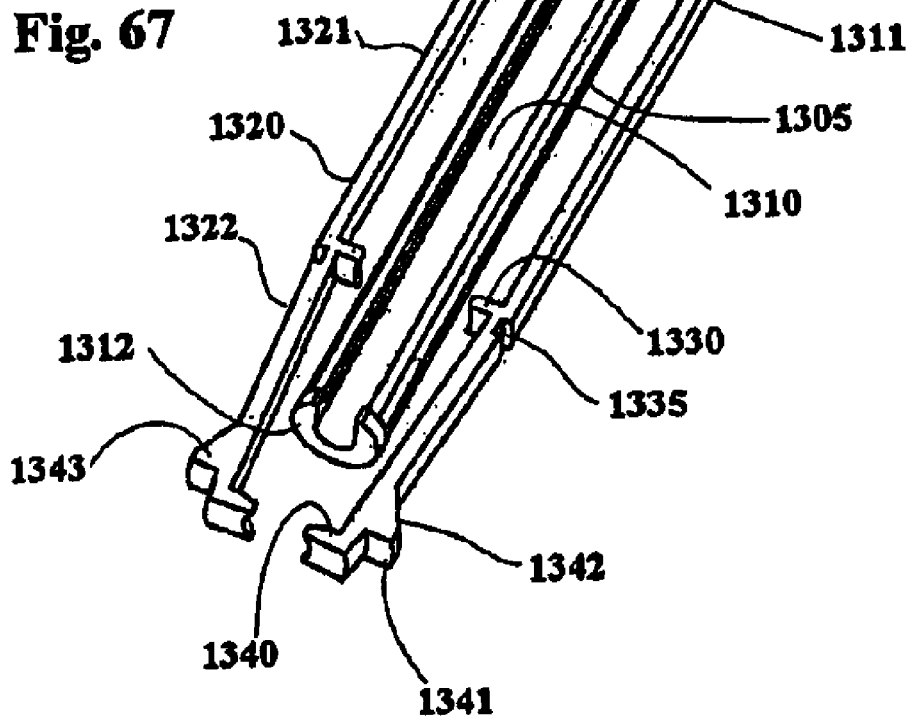
FIG. 68 is an isometric view of the driver of the exemplary embodiment as manufactured and after delivery completion.

Driver 1300 is detailed in FIG. 67 and FIG. 68. Driver 1300 has a driver rod 1305 with two side arms 1320 connected by a base 1350. Arms 1320 have a front section 1322 and a rear section 1321. Arms have protrusions 1343 and cartridge followers 1330 and 1340 leaning on the outer surface of the cartridge 1500. Furthermore protrusions 1343 have a slopped surface 1342 interacting with the driving means and a front surface 1341. The side arms also have an undercut 1335 to assist in bending of the arms. The driver rod 1305 has a channel like structure 1310 and a front plate 1312. Channel 1310 has a proximate end 1311. The outer surface of the protrusion 1352 interfaces with a housing opening. A rotational moment is created by the driving means due to the force applied on the sloped surface 1342 with reference to the support point 1330. Undercut 1335 provides a narrow section used as an axis to allow the bending in of front arm once cam 1340 is no longer supported by the cartridge. When stopper 1510 reaches the end of delivery, cam 1340 is able to bend in and allow the driving mechanism 1400 to bypass the driver.

Figure 69:
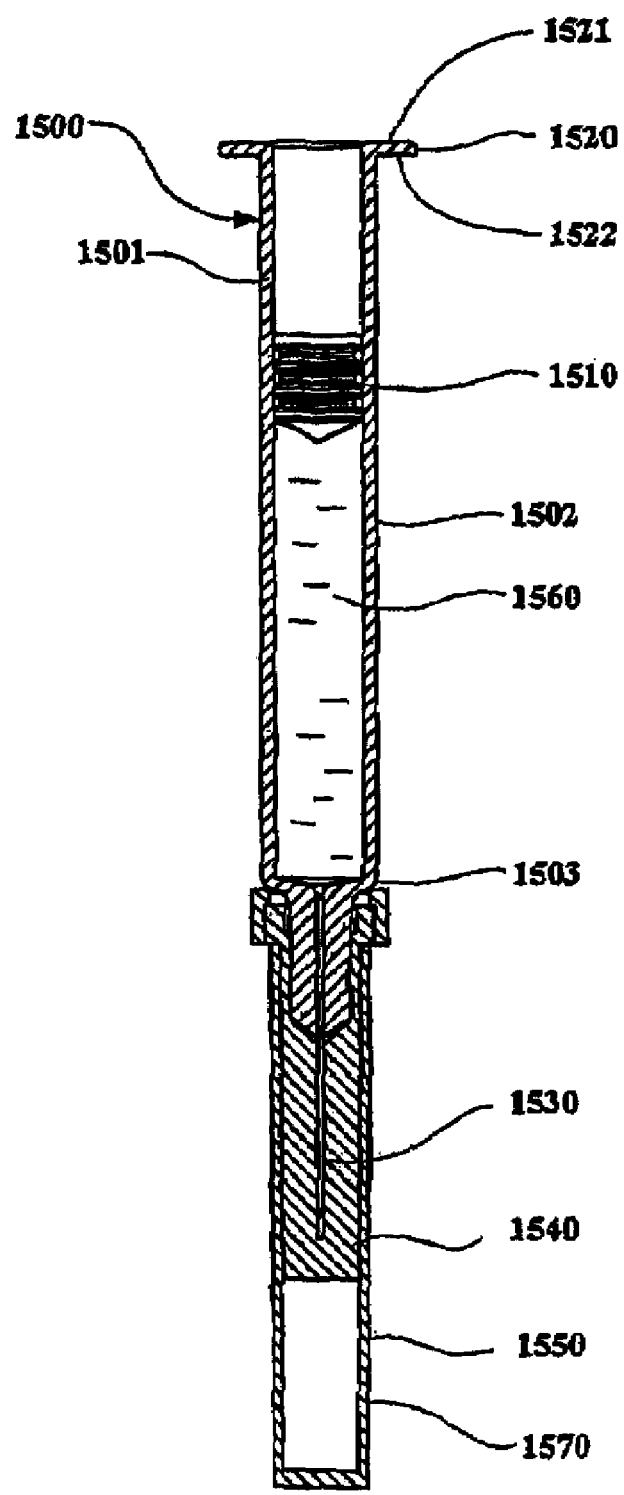
FIG. 69 is illustrating an exemplary embodiment of the filled cartridge of the present invention.
Figure 74:
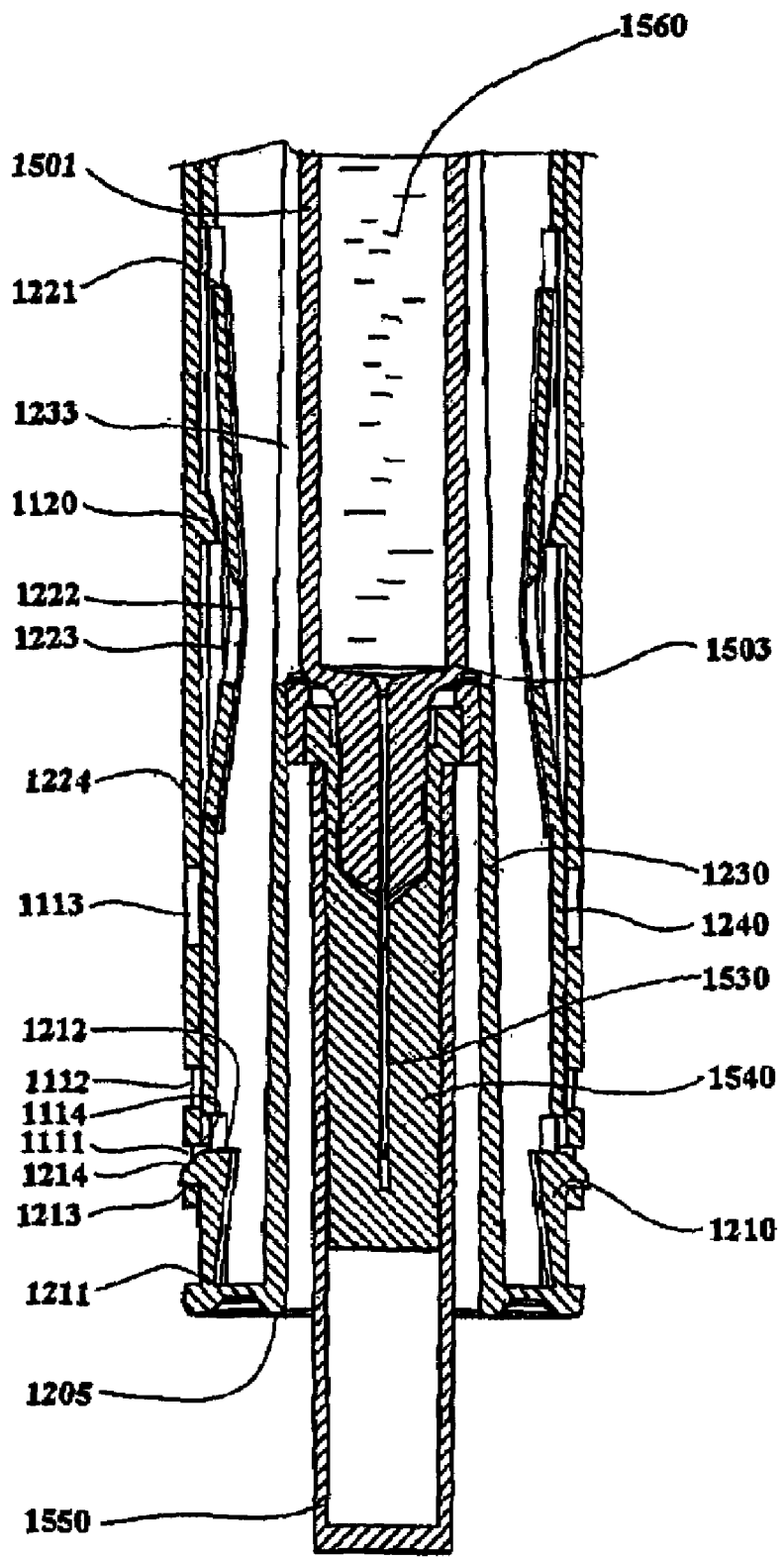
FIG. 74 is a detail of cross-section view similar to that of FIG. 52 showing the delivery and discard locking elements in storage position.
Figure 75:
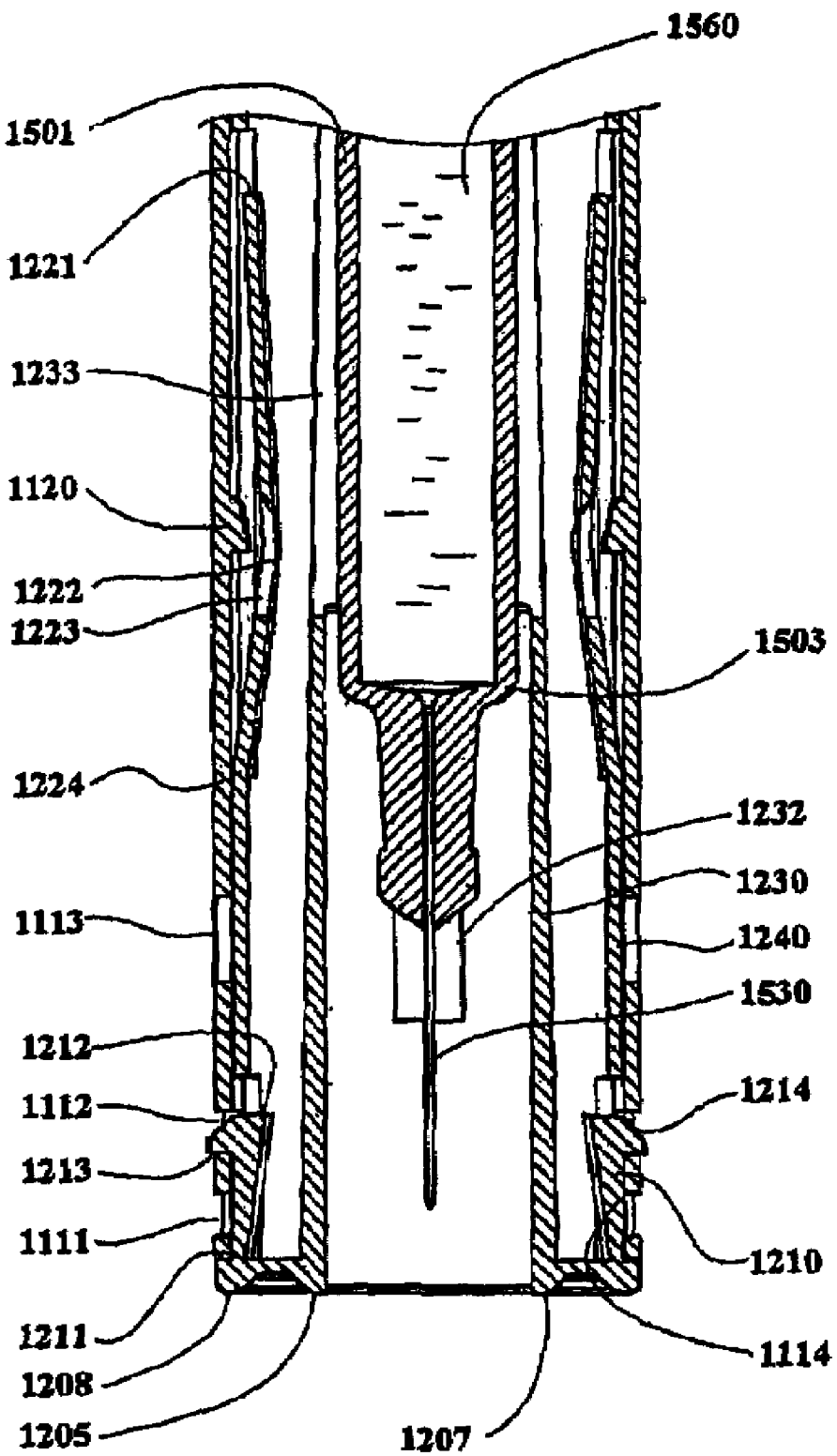
FIG. 75 is a detail of cross-section view similar to that of FIG. 54 showing the distal end as pushed against an injection site with the distal end of the shield engaged to the housing in the second position and the device activated.
Figure 76:
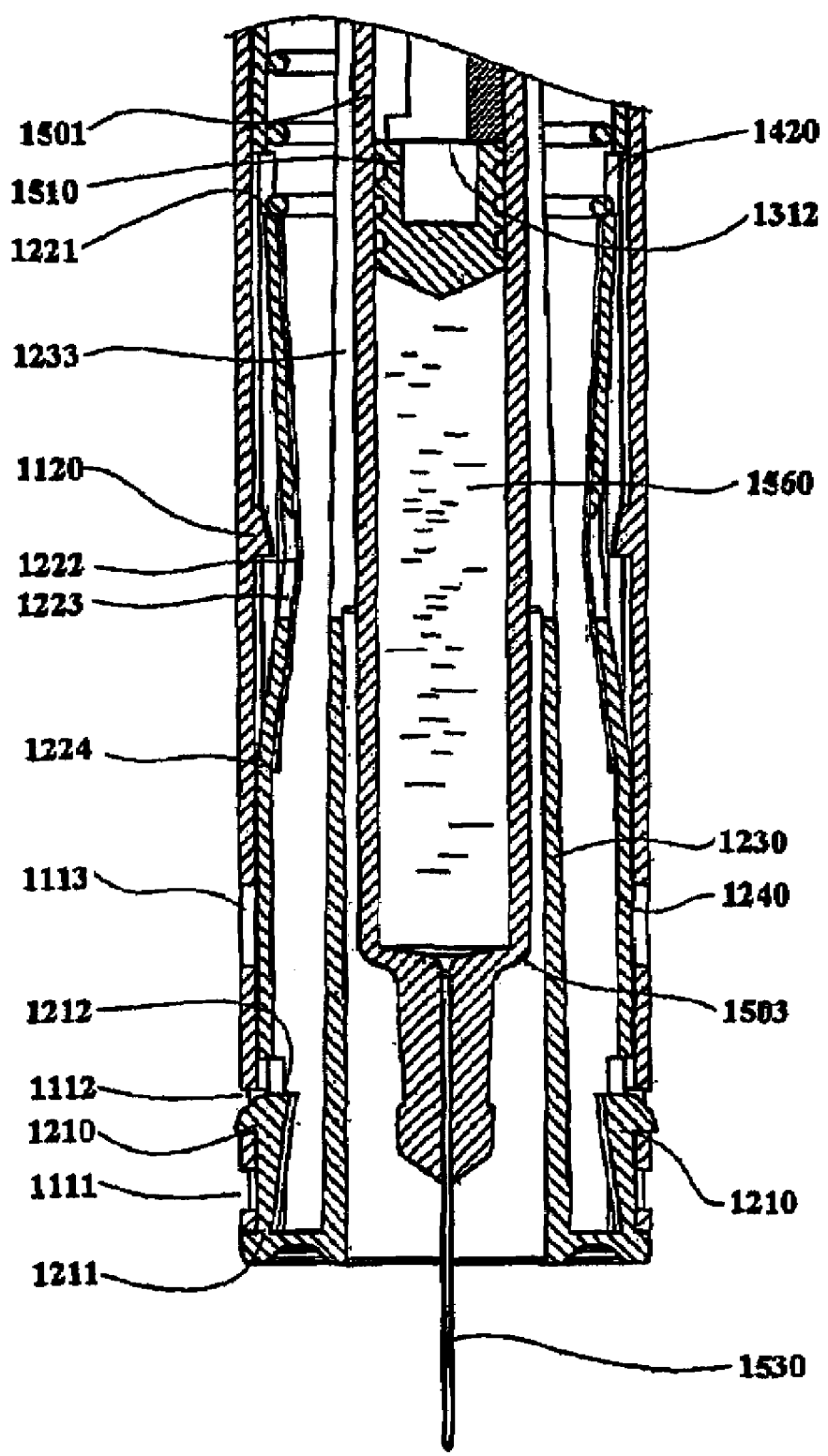
FIG. 76 is a detail of a cross-section view similar to that of FIG. 56 showing the injector in a state wherein the cartridge is advanced toward the distal end, the needle is inserted into the tissue and the injection is initiated.
Figure 77:
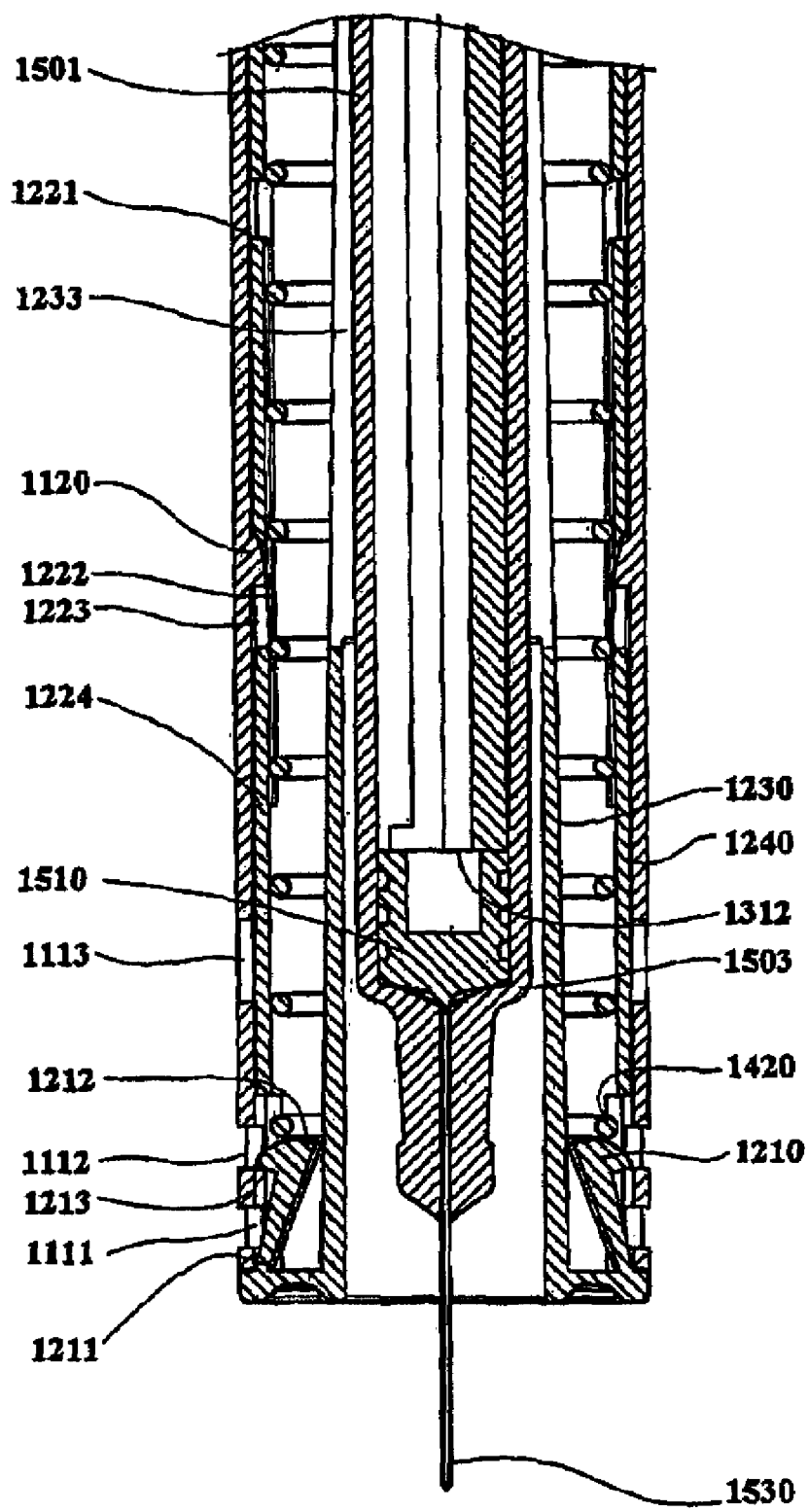
FIG. 77 is a detail of cross-section view similar to that of FIG. 58 but showing the injector in a state wherein the delivery is completed, spring has bypassed the driver and is impacting the shield.
Figure 78:
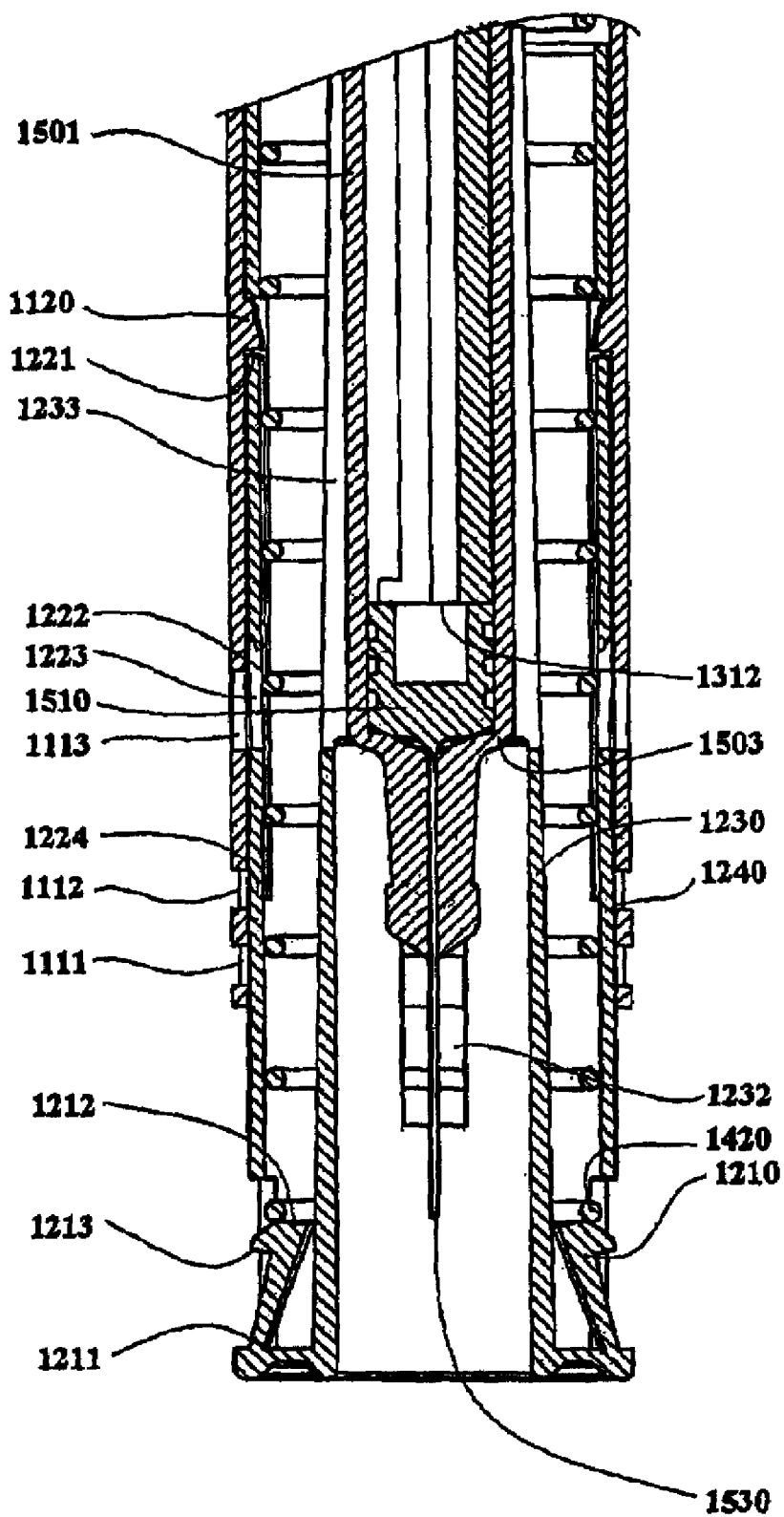
FIG. 78 is a detail of cross-section view similar to that of FIG. 60 but showing the injector in a state wherein the shield is extended and the device is secured in its discard position.

A typical cartridge 1500 is illustrated in FIG. 69. It has a glass barrel 1501 with a staked needle 1530. The glass barrel 1501 has flange 1520. The barrel is filled with drug 1560. The drug is sealed by a stopper 1510 which is in a sliding relationship with the barrel. The needle is shielded by a protective cover 1540 made from an elastomeric needle sterility cover abutting the needle. The needle protective cover 1540 frequently has a rigid plastic protector 1550 together with 1540 forming a needle cover assembly 1570 which could simplify the cover removal. Alternatively the cartridge could have a double sided needle (as in Carpuject™ cartridge). The needle would require an axial force at the beginning of operation to activate the cartridge and to cause the penetration of the proximate end of the needle through the rubber stopper for drug delivery.

Use of the Device Will Now be Described:

As shown in FIG. 52 of the preferred embodiment, the first step in the use of the injector is to remove the needle cover assembly 1570. Then the automatic injector is applied to the injection site with a pressure applied to the housing 1100. This action results in triggering the automatic insertion of the needle 1530 into the tissue and an automatic initiation of the injection. During the injection time the injector holding force is close to zero as illustrated by element 1734 in FIG. 63. Upon completion of the injection the spring 1400 moves forward to apply a force to the shield 1200. The force acting on the shield increases to the level of the spring force as illustrated by 1721 and 1736 respectively in FIG. 62 and FIG. 63. This force leads to the extraction of the needle from the tissue and shielding of the needle by the shield 1200. The spring force decays through the motion (see 1722 and 1737). At the end of the shielding process the shield is locked. The injector is ready for disposal.

Without being limited to a particular theory, as an example of the balances of forces working in the injector, it generally takes about 1.0 kgf to displace the shield 1200 by about 4 mm while releasing the driver. The initial injection force of the driving unit 400 is, for example, about 2 kgf, and the final pushing force during shielding is about 1 kgf. The dynamic friction force will take, for example, 0.2 kgf at maximum.

The exemplary embodiments show the injector having a distal end from which the needle is exposed, and a proximate end opposite the distal end. In the exemplary embodiment, the injector deploys its needle automatically, delivers the drug in the cartridge and shields the needle automatically. Preferably the injector provides a distinct end of delivery indication (e.g., a 'click-type' effect and associated tactile feedback). The injector can be assembled around a cartridge.

The high force for moving the shield at the beginning of use prevents premature displacement of the shield. Furthermore the discard and locking mechanism locks the shield after use. The injector optionally includes damping material (e.g., the bushing, shock absorbing tab) for shock and noise reduction. The injector provides linear rate control using a low elasticity constant spring, preferably in the form of an expansion spring. The expansion spring can be made longer so that the cartridge stopper displacement over a small longitudinal range is short compared to the length of the spring, thereby allowing the force of the spring to be consistent over the smaller range.

As a person skilled in the art would readily understand, delivery of the fluid drug is determined not only by the driving unit or spring. It also depends on fluid properties and the fluid's path geometry. Therefore, delivery curves will not be identical to spring reaction curves. The fluid acts as a hydraulic damper and its resistance to flow is related to the force applied to it.

The driving unit in the exemplary embodiments can be a spring. The compression spring is preferably used in the embodiments having a substantially symmetrical housing cross-section. The required motion range and the accumulated thickness of the coils limit this initial compression.

The driving spring is the most available element to control delivery. The main feature provided from the spring is a low elasticity constant. A low constant provides a more uniform delivery profile, more flexibility in controlling delivery duration, spring load reduction during shelf life, and it provides sufficient force at the end of the injection cycle. Using long springs provides the benefit of improving delivery time control and profile by changing the spring's constant of elasticity and by allowing preloads.

This invention overcomes other problems associated with the prior art. For example, the driver and springs overcome the problems of needle phobia and needle injury. Further, the window 1110 provides the user with the ability to see dosage formulation prior to use, and to confirm visually that the drug has been delivered by looking through slit 1113.

It should be apparent from the aforementioned description and attached drawings that the concept of the present application may be readily applied to a variety of preferred embodiments, including the exemplary embodiments disclosed herein. For example, other driving and retraction units falling within the definition of a "spring", such as elastomeric "O" rings or compressed gas, may be used in place of the coil springs disclosed herein to bias the driver, as readily understood by a skilled artisan.

Figure 79:
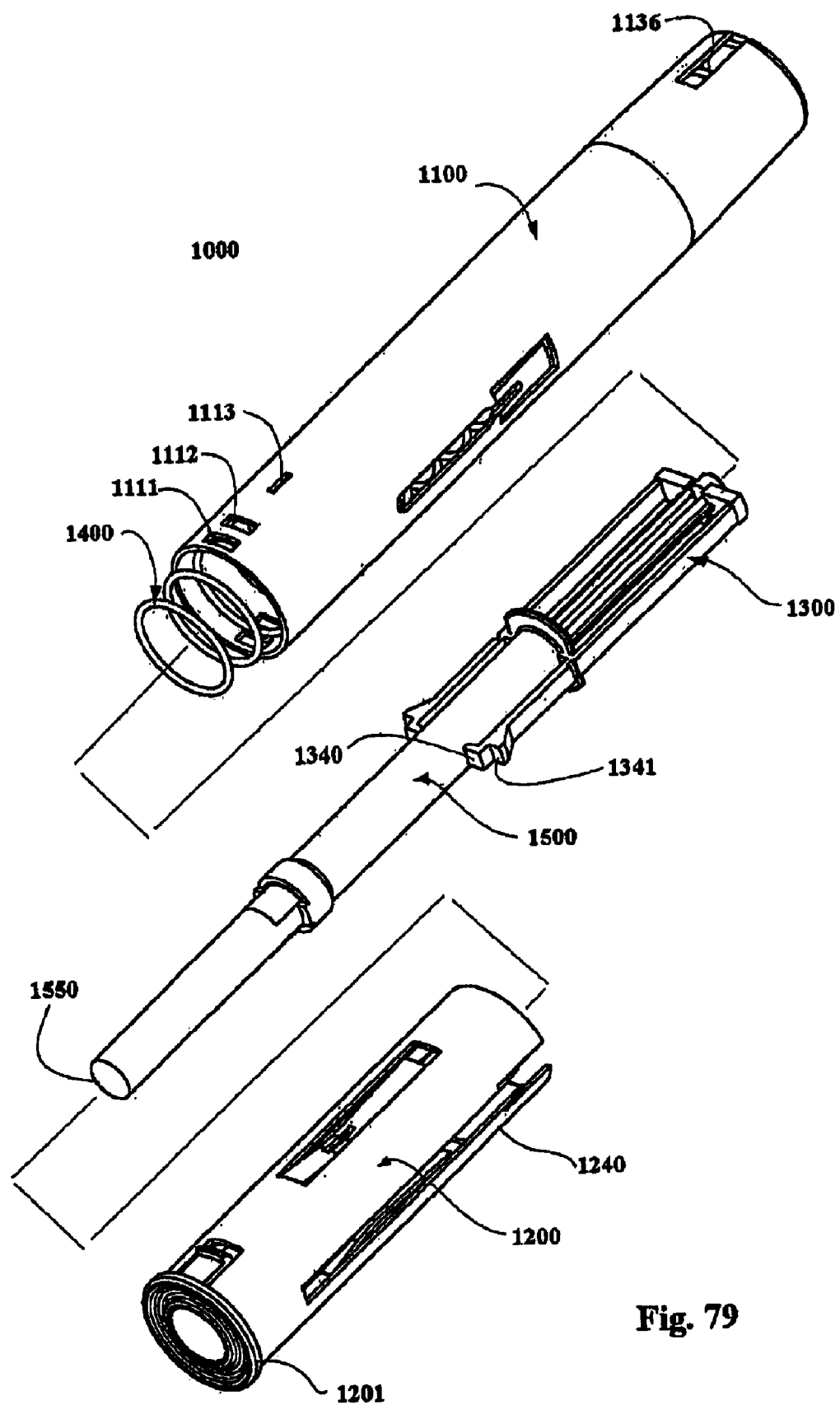
FIG. 79 is a view of the assembly process of the cartridge/driver and housing/spring and shield sub-assembly merger.

The assembly process for the exemplary embodiment is illustrated in FIG. 79. The first step includes the assembly of cartridge 1500 with the driver 1300. The spring 1400 is placed within the housing 1100. The driver/cartridge subassembly is merged with housing/spring subassembly. Adding the shield 1200 completes the automatic injector. The locking hook 1210 engages the storage slot 111 maintaining the engagement of shield 1200 to housing 1100. The assembly process is simple due to the small number of components and the "single axis" process.

The automatic injector could be equipped with a safety tab 1600 as illustrated in FIG. 80 and FIG. 81. The shield proximate displacement requires the removal of the safety tab providing an additional step in the safe operation of the injector. Alternatively the automatic injector could be equipped with a cup snapped to the needle cover assembly 1570 and engaged with the distal end of the injector 1001. The triggering of the injector through the shield proximate displacement, requires the removal of the cup together with the needle cover assembly.

It is further appreciated that the present invention may be used to deliver a number of drugs. The term "drug" used herein includes but is not limited to peptides or proteins (and mimetic thereof), antigens, vaccines, including DNA vaccines, hormones, analgesics, anti-migraine agents, anti-coagulant agents, medications directed to the treatment of diseases and conditions of the central nervous system, narcotic antagonists, immunosuppressants, agents used in the treatment of AIDS, chelating agents, anti-anginal agents, chemotherapy agents, sedatives, anti-neoplastics, prostaglandins, antidiuretic agents and DNA or DNA/RNA molecules to support gene therapy.

Typical drugs include peptides, proteins or hormones (or any memetic or analogues of any thereof) such as insulin, calcitonin, calcitonin gene regulating protein, atrial natriuretic protein, colony stimulating factor, betaseron, erythropoietin (EPO), interferons such as alpha., .beta., or gamma. interferon, somatropin, somatotropin, somastostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues or antagonists thereof, such as IL-1ra, thereof; analgesics such as fentanyl, sufentanil, butorphanol, bup renorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; antiemetic agents such as scopolamine, ondansetron, domperidone, metoclopramide, and analogues thereof; cardiovascular agents, anti-hypertensive agents and vasodilators such as diltiazem, clonidine, nifedipine, verapamnil, isosorbide-5-mononitrate, organic nitrates, agents used in treatment of heart disorders, and analogues thereof; sedatives such as benzodiazepines, phenothiozines, and analogues thereof; chelating agents such as deferoxamine, and analogues thereof; anti-diuretic agents such as desmopressin, vasopressin, and analogues thereof; anti-anginal agents such as nitroglycerine, and analogues thereof; anti-neoplastics such as fluorouracil, bleomycin, and analogues thereof; prostaglandins and analogues thereof; and chemotherapy agents such as vincristine, and analogues thereof, treatments for attention deficit disorder, methylphenidate, fluoxamine, Bisolperol, tactolimuls, sacrolimus and cyclosporin.

The invention claimed is:

1. An injection device comprising:
    a housing having a proximate end and a distal end, the distal end having an opening therein;
    a shield slideably coupled to the housing and having a shield base and aperture positioned at said distal end thereof;
    a cartridge barrel within the housing, the cartridge barrel having proximate and distal ends;
    a needle cannula fixed to the distal end of the cartridge barrel, or attachment means for fixing a needle cannula to the distal end, said needle cannula being disposed within said shield prior to activation of said device;
    a stopper within the cartridge barrel;
    a driver coupled to the stopper;
    a spring coupled between the housing and the driver;
    an automatic driver trigger for retaining the driver fixed to the housing and in which state the spring is in a compressed state, the trigger being actuable by displacing said shield towards said proximal end of housing, thereby permitting passage of said needle cannula through said aperture, said actuated trigger automatically releasing the driver from the housing thereby allowing the spring to urge the driver through the housing and with it the stopper through the cartridge barrel; and
    a release mechanism for releasing the spring from the driver at some point on its travel through the housing, whereupon the spring engages the shield base and automatically urges the shield away from the housing so as to cover the needle cannula.

2. An injection device according to claim 1 and comprising means for allowing the driver to drive the cartridge barrel through the housing following activation of said driver trigger and prior to movement of the stopper through the cartridge, thereby urging the needle cannula outward relative to the housing and shield.

3. An injection device according to claim 1, the driver trigger being coupled to said shield, wherein movement of the shield inwardly with respect to the housing activates the trigger.

4. An injection device according to claim 3, wherein said trigger is actuated prior to the emergence of the needle cannula from the shield.

5. An injection device according to claim 3, wherein said trigger is actuated subsequent to emergence of the needle cannula from the shield.

6. An injection device according to claim 1, wherein the driver trigger comprises a resilient member on one of the driver and the housing and a complimentary engaging member on the other of the driver and housing, and wherein said trigger is actuated by a force of sufficient magnitude applied between the driver and the housing.

7. An injection device according to claim 1, wherein said driver trigger comprises a resilient member on one of the driver and the housing and a complimentary engaging member on the other of the driver and housing, and wherein said trigger is arranged to receive a trigger release member of the shield following movement of the shield into the housing.

8. An injection device according to claim 1, wherein said housing is generally cylindrical in shape and the spring and cartridge barrel are located coaxially within the housing.

9. An automatic injector for delivering a fluid, comprising:
    a housing, said housing having a proximate end and a distal end;
    a shield interfaced with the housing at a housing distal end and wherein said housing and said shield are arranged in a sliding relationship forming an enclosure, said shield comprising a base having an aperture positioned at said distal end of said housing;
    a driver positioned within said enclosure and engaged to the housing and adapted to automatically disengage from the housing upon displacement of said shield towards said proximate end of said housing;
    a cartridge positioned within said enclosure, and wherein said cartridge comprises:
        a needle extending towards said shield base, said needle being disposed within said shield prior to displacement of said shield, said needle passing through said aperture when said shield is displaced; and
        a barrel, said barrel arranged to contain a stopper and the fluid therein and wherein the fluid is in communication with said needle;
    said driver slidingly located within said housing for forcing the fluid through said needle upon activation of said injector; and
    said driver further adapted to be biased by a driving unit, said driving unit causing said driver to slide towards said housing distal end and move a stopper through said barrel to push the fluid through said needle for delivery into an injection site; and
    wherein said shield is automatically deployed following fluid delivery so as to cover the needle.

10. The automatic injector of claim 9, wherein said shield displacement and driver disengagement require a substantial force over a short travel distance.

11. The automatic injector of claim 10, wherein said shield displacement and driver disengagement force required from the user is about 1 kgf.

12. The automatic injector of claim 10, wherein the driver disengagement from the housing takes place over the initial part of the shield travel.

13. The automatic injector of claim 9 wherein said force exerted by the automatic injector on the shield is minimal during delivery.

14. The automatic injector of claim 9, further comprising an automatic extension mechanism that automatically extends said shield after the completion of injection.

15. The automatic injector of claim 14, wherein said driver is arranged to allow the driving unit to force the extension of the shield and shielding the needle at the end of delivery.

16. The automatic injector of claim 9 wherein said housing includes a set of supports extending longitudinally from a proximate end of the housing, said supports adapted to abut said cartridge and prevent axial movement of said cartridge before, during and after operation of the automatic injector.

17. The automatic injector of claim 9, wherein said driver includes a set of cartridge supports extending longitudinally and which slide on the external surface of the barrel during injection.

18. The automatic injector of claim 17, wherein said cartridge supports are adapted to detect the end of barrel and release the driving unit.

19. The automatic injector of claim 9 wherein said driving unit is a spring arranged to bias said driver to push said stopper into said barrel and then move said shield into a needle shielding position.

20. The automatic injector of claim 19, wherein the released spring provides the user with a tactile and audible feedback of the end of delivery.

21. The automatic injector of claim 9 wherein said driver comprises protrusions that releasably engage said housing.

22. The automatic injector of claim 9 wherein said housing has an opening at said proximate end, said driver further comprising a rod extending through said opening and arranged to push said stopper into said barrel before activation of said injector.

23. The automatic injector of claim 22, wherein said rod has a smooth surface for axial movement in relation to said housing opening.

24. The automatic injector of claim 22, wherein said rod has a threaded section for rotational axial movement in relation to said housing opening.

25. The automatic injector of claim 23, wherein said rod has a serrated edge for incremental axial movement in relation to said housing opening.

26. The automatic injector of claim 9 further comprising a safety tab removably engaged with said enclosure, said tab arranged to prevent activation of said injector when said tab is engaged with said enclosure.

27. The automatic injector of claim 9 wherein said cartridge has a closed distal end and a proximate end, said needle having a distal end for exposure to the injection site and a proximate end arranged to penetrate said closed distal end of the cartridge and providing fluid communication between the distal end of the needle and the interior of the cartridge, said proximate end of said cartridge arranged to accept said driver.

28. The automatic injector of claim 9 wherein said shield has an inner circumferential wall and an outer circumferential wall, said housing having an inner circumferential wall and an outer circumferential wall, said housing and said shield arranged in a sliding relationship, said housing and said automatic injector having an arrangement for latching the shield in the needle shielding position.

29. The automatic injector of claim 28, wherein said enclosure further comprises a leaf spring at said distal end of the enclosure, said leaf spring arranged to abut said driving unit after retraction of said shield and prevent potential re-exposure of said needle.

30. The automatic injector of claim 28, wherein said enclosure further comprises pins and pattern arranged at said distal end of enclosure, said pins and pattern arranged to interact during the use of the automatic injector and prevent potential re-exposure of said needle.

31. The automatic injector of claim 21, wherein said activation of said injector occurs after application of the axial pressure on the housing of the injector; said shield moving to expose the needle and to separate said protrusions from said housing to allow axial movement of said driver and said stopper in said barrel, holding said injector at the injection site for the during of the injection.

32. The automatic injector of claim 28, wherein said housing and shield further include a window arranged to allow viewing of the barrel, a barrel scale and the fluid in the barrel.

33. The automatic injector of claim 32, wherein said housing and said shield further have two matching slots in conjunction forming the window.

34. The automatic injector of claim 32, wherein said housing and said shield further have two matching openings in conjunction forming the window.

35. The automatic injector of claim 28, wherein said shield outer circumferential wall are arranged in a sliding relationship with said housing inner circumferential wall.

36. The automatic injector of claim 28, wherein said shield inner circumferential wall are arranged in a sliding relationship with said housing outer circumferential wall.

37. The automatic injector of claim 33, wherein said housing further has an extended section enveloping said shield and providing improved holding ability for the user.

38. An automatic injector for delivering a fluid comprising:
a housing, said housing having a proximate end and a distal end;
a shield interfaced with the housing at a housing distal end, wherein said housing and said shield are arranged in a sliding relationship forming an enclosure, said shield comprising a base having an aperture positioned at said distal end of said housing;
a driver positioned within said enclosure and engaged to the housing and adapted to automatically disengage from the housing upon displacement of the shield towards said proximate end of said housing;
a cartridge positioned within said enclosure, said cartridge comprising:
a needle extending towards said shield base, said needle being disposed within said shield prior to displacement of said shield, said needle passing through said aperture when said shield is displaced; and
a barrel, said barrel arranged to contain a stopper and the fluid therein, the fluid in communication with said needle;
a rod, forming a portion of said driver, arranged to communicate with said stopper before the activation, said rod arranged to move said stopper for titration before the activation and to automatically separate from said stopper upon activation;

said driver being slidingly located within said housing for forcing the fluid through said needle upon activation of said injector;

said driver further adapted to be biased by a driving unit and said driving unit causing said driver to slide towards said distal end and move said stopper through said barrel to push the fluid through said needle for delivery into an injection site; and wherein said shield is automatically deployed following fluid delivery delivery so as to cover the needle.

39. The automatic injector of claim 38, wherein said housing has an aperture on the proximate end, said rod arranged to extend into said aperture during communication with said stopper and move said stopper during titration.

40. The automatic injector of claim 39, wherein said rod has a section for axial movement in relation to said housing opening.

41. The automatic injector of claim 39, wherein said rod has a threaded section for rotational axial movement in relation to said housing opening.

42. The automatic injector of claim 39, wherein said rod has a serrated edge for incremental axial movement in relation to said housing opening.

43. The automatic injector of claim 38, wherein said injector further includes a window arranged to allow viewing of the cartridge fluid.

44. An injector for automatically injecting and delivering fluids into a living being, said injector comprising:

a housing having a proximal end and a distal end that is open;

a cartridge having a barrel containing a fluid, said cartridge further comprising a displaceable stopper at a proximal end of said cartridge and a needle at a distal end of said cartridge, said cartridge being fixed within said housing;

a driver engaged within said housing for driving said stopper to dispense the fluid from said barrel and through said needle when disengaged from said housing;

a needle shield being in sliding engagement with said distal end of said housing and comprising an opening for permitting said needle to pass therethrough, said needle being disposed within said needle shield prior to activation of said injector; and a single spring, engaged with said driver, that is released by a user force, said single spring displacing said driver for automatically injecting and delivering the fluid into the living being and for automatically acting against the needle shield to remove the needle from the living being while automatically concealing the needle within said shield once the fluid delivery is complete.

45. An automatic injector for delivering a fluid, comprising:

a housing, said housing having a proximate end and a distal end;

a shield interfaced with the housing and comprising a shield base having an aperture;

said housing and said shield arranged in a sliding relationship forming an enclosure;

said driver positioned within said enclosure;

a cartridge positioned within said enclosure, said cartridge comprising:

a needle extending towards said shield base, said needle being disposed within said shield prior to displacement of said shield, said needle passing through said aperture when said shield is displaced; and a barrel, said barrel arranged to contain a stopper and the fluid therein, the fluid in communication with said needle, said driver slidingly located within said housing for moving the needle forward to insert it into tissue and for forcing the fluid through said needle upon activation of said shield;

a driver attached to the housing and adapted to automatically disengage from the housing upon activation of the injector;

said driver further adapted to be biased by a driving unit and said driving unit causing said driver to slide towards said distal end to forward the cartridge with the needle and move said stopper through said barrel to push the fluid through said needle and deliver fluid into an injection site; and wherein said shield is automatically deployed following fluid delivery so as to cover the needle.

46. The automatic injector of claim 45, wherein said shield displacement requires a substantial force over a short travel distance.

47. The automatic injector of claim 46, wherein the shield displacement force is sufficient to ensure rapid housing and shield disengagement.

48. The automatic injector of claim 45, wherein said the force exerted by the shield of the automatic injector on the tissue is minimal during delivery.

49. The automatic injector of claim 48, wherein the shield and the housing have latches maintaining the relative housing to shield position during delivery.

50. The automatic injector of claim 45, wherein the force exerted by the automatic injector moves the cartridge toward the distal end of the automatic injector to insert the needle into tissue and deliver the drug.

51. The automatic injector of claim 45, further comprising a mechanism that automatically extends said shield and shields the needle after the completion of injection 52. The automatic injector of claim 51, wherein said driver is arranged to allow the driving unit to force the shield in the distal direction and shield the needle at the end of delivery.

53. The automatic injector of claim 45, wherein said housing includes a support extending longitudinally from said proximate end of the housing, said support adapted to abut said cartridge and prevent axial movement of said cartridge before use.

54. The automatic injector of claim 45, wherein said shield includes protrusions extending longitudinally from the distal end and limiting cartridge motion toward the distal end of the injector after activation.

55. The automatic injector of claim 45, wherein said driver includes a set of barrel supports extending longitudinally and sliding on the external surface of the barrel during injection.

56. The automatic injector of claim 55, wherein said barrel supports are adapted to detect the end of barrel and release the shield.

57. The automatic injector of claim 55, wherein said driver has protrusions supporting the barrel from axial motion toward the distal end of the automatic injector after injection completion.

58. The automatic injector of claim 45, wherein said driving unit is a spring arranged to bias said driver to push said cartridge to insert the needle into tissue, to push said stopper into said barrel and then move said shield into needle shielding position.

59. The automatic injector of claim 58, wherein said released spring provides the user with a tactile and audible feedback of the end of delivery.

60. The automatic injector of claim 45, wherein said driver comprises protrusions, said driver protrusions releasably engaging said housing.

61. The automatic injector of claim 60, said activation of said injector occurs after application of an axial force on the shield of the injector; said shield moving to separate said driver protrusions from said housing to allow fluid delivery while holding said injector at the injection site for the duration of the injection.

62. The automatic injector of claim 45, wherein said cartridge comprises a closed distal end and a proximate end, said needle having a distal end for exposure to the injection site and a proximate end arranged to penetrate said closed distal end of the cartridge and provide fluid communication between the distal end of the needle and the interior of the cartridge, said proximate end of said cartridge arranged to accept said driver.

63. The automatic injector of claim 45, wherein said shield has an inner circumferential wall and an outer circumferential wall, said housing having an inner circumferential wall and an outer circumferential wall, said housing and said shield arranged in a sliding relationship, and said automatic injector having arrangements for latching the shield to the housing.

64. The automatic injector of claim 63, wherein said shield further comprises a hook at said distal end and the housing comprising matching windows at distal end of said housing for engaging the shield and housing in storage and delivery positions.

65. The automatic injector of claim 63, wherein said shield further comprises a leaf spring said leaf spring arranged to abut said driving unit after retraction of said shield and prevent potential re-exposure of said needle.

66. The automatic injector of claim 45, further comprising a safety tab removeably engaged with said enclosure, said tab arranged to prevent activation of said injector when said tab is engaged with said enclosure.

67. The automatic injector of claim 63, wherein said housing and shield further include a window arranged to allow viewing of the barrel, a barrel scale and the fluid in the barrel.

68. The automatic injector of claim 67, wherein said housing and said shield further include matching openings across diameter in conjunction forming the window.

69. The automatic injector of claim 45, wherein said injector is equipped with a safety tab said shield proximate displacement requires the removal of the safety tab.

70. The automatic injector of claim 45, wherein said injector is equipped with a needle cover assembly cup, said shield displacement requires the removal of the cup together with the needle cover assembly.

* * * * *